United States Patent
Brann

(10) Patent No.: US 7,425,420 B2
(45) Date of Patent: *Sep. 16, 2008

(54) IDENTIFICATION OF LIGANDS BY SELECTIVE AMPLIFICATION OF CELLS TRANSFECTED WITH A 5HT2A RECEPTOR

(75) Inventor: Mark R. Brann, Del Mar, CA (US)

(73) Assignee: Acadia Pharmaceuticals Inc., San Diego, CA (US)

(*) Notice: Subject to any disclaimer, the term of this patent is extended or adjusted under 35 U.S.C. 154(b) by 113 days.

This patent is subject to a terminal disclaimer.

(21) Appl. No.: 11/083,173

(22) Filed: Mar. 16, 2005

(65) Prior Publication Data

US 2005/0244862 A1    Nov. 3, 2005

Related U.S. Application Data

(63) Continuation of application No. 10/130,812, filed as application No. PCT/US99/21439 on Oct. 7, 1999, now abandoned.

(51) Int. Cl.
G01N 33/566 (2006.01)
C07K 14/705 (2006.01)

(52) U.S. Cl. .................. 435/7.1; 435/7.2; 435/7.21; 436/501

(58) Field of Classification Search .................. None
See application file for complete search history.

(56) References Cited

U.S. PATENT DOCUMENTS

| | | | |
|---|---|---|---|
| 5,071,858 A | 12/1991 | Hutchison | |
| 5,401,629 A | 3/1995 | Harpold et al. | |
| 5,573,908 A | 11/1996 | Allen et al. | |
| 5,635,528 A | 6/1997 | Audia et al. | |
| 5,661,024 A | 8/1997 | Kao et al. | |
| 5,707,798 A * | 1/1998 | Brann | 435/6 |
| 5,912,132 A | 6/1999 | Brann | |
| 5,955,281 A | 9/1999 | Brann | |
| 6,107,324 A * | 8/2000 | Behan et al. | 514/406 |

FOREIGN PATENT DOCUMENTS

| | | |
|---|---|---|
| EP | 0 244 221 | 11/1987 |
| EP | 0 371 820 | 6/1990 |
| WO | WO 92/01810 | 2/1990 |
| WO | WO 92/05244 | 4/1992 |
| WO | WO 93/23431 | 11/1993 |
| WO | WO 95/02823 | 1/1995 |
| WO | WO 95/06117 | 3/1995 |
| WO | WO 96/17081 | 6/1996 |
| WO | WO 97/21731 | 6/1997 |
| WO | WO 97/38991 | 10/1997 |
| WO | WO 97/39001 | 10/1997 |
| WO | WO 98/38217 | 9/1998 |
| WO | WO 99/52927 | 10/1999 |

OTHER PUBLICATIONS

Barker, et al., "Constitutively Active 5-Hydroxytryptamine$_{2C}$ Receptor Reveal Novel Inverse Agonist Activity of Receptor Ligands", *J. of Biological Chemistry*, (Apr. 22, 1994) 269(16):11687-11690.

Barr, et al, "Agonist-independent Activation of G$_z$ by the 5-Hydroxytryptamine$_{1A}$ Receptor Co-expressed in *Spodoptera frugiperda* Cells", *J. of Biological Chemistry*, (Dec. 26, 1997) 272(52):32979-32987.

Benes, et al, "Altered Neural Circuits in Schizophrenia", *The Harvard Mental Health Letter*, Nov. 1996, 13(5).

Buckland, et al., "The effects of antipsychotic drugs on the mRNA levels of serotonin 5HT$_{2A}$ and 5HT$_{2C}$ receptors", *Molecular Brain Research*, (1997) 48:45-52.

Burnet, et al., "The Effects of Clozapine and Haloperidol on Serotonin-1A, -2A and -2C Receptor Gene Expression and Serotonin Metabolism in the Rat Forebrain", *Neuroscience*, (1996) 73(2):531-540.

Casey, et al., "Constitutively active mutant 5HT$_{2A}$ receptors", *Society for Neuroscience Abstracts*, (1996) 22(3):699-710.

Charpentier, et al., "Silencing of the Constitutive Activity of the Dopamine D1B Receptor", *J. Biological Chemistry*, (Nov. 8, 1996) 271(45):28071-28076.

Chidiac, et al., "Inverse Agonist Activity of β-Adrenergic Antagonists", *Molecular Pharmacology*, 45:490-499. (Mar. 1994).

Costa, et al., "Antagonists with negative intrinsic activity at δ opioid receptors coupled to GTP-binding proteins", *Biochemistry*, (Oct. 1989) 86:7321-7325.

Costa, et al., "Drug Efficacy at Guanine Nucleotide-Binding Regulatory Protein-Linked Receptors: Thermodynamic Interpretation of Negative Antagonism and of Receptor Activity in the Absence of Ligand", *Molecular Pharmacology*, 41:549-560. (Mar. 1991).

Egan, et al., "Creation of a constitutively activated state of the 5HT$_{2A}$ receptor by site-directed mutagenesis: revelation of inverse agonist activity of antagonists", *Annals NY Acad. Sci.*, (1998) 861:136-139.

Egan, et al., "Creation of a constitutively activated state of the 5-hydroxytryptamine$_{2A}$ receptor by site-directed mutagenesis: inverse agonist activity of antipsychotic drugs," *JPET*, (1998) 286:85-90.

(Continued)

*Primary Examiner*—John D Ulm
(74) *Attorney, Agent, or Firm*—Knobbe, Martens, Olson & Bear LLP

(57) ABSTRACT

The invention is directed to a method for identifying substances acting as ligands for transfected receptors by using transfected markers to measure receptor/ligand interactions. The present invention also relates to a method of identifying compounds which act as inverse agonists of the 5-HT2A receptor, the method comprising contacting a constitutively active 5-HT2A receptor with at least one test compound and determining any decrease in the amount of basal activity of the receptor so as to identify a test compound which is an inverse agonist of the 5-HT2A receptor. Such inverse agonists may be used in the treatment of schizophrenia and related psychoses.

65 Claims, 25 Drawing Sheets

OTHER PUBLICATIONS

Eggericks, et al., "Molecular cloning of an orphan G-protein-coupled receptor that constitutively activates adenylate cyclase", *Biochemcial J.*, (1995) 309:837-843.

Ferry, et al., "Effects of Agonists, Partial Agonists, and Antagonists on the Regulation of 5-Hydroxytryptamine$_2$ Receptors in P11 Cells", *Molecular Pharmacology*, 43:726-733. (May 1993).

Frazier, et al., "The Brains of Schizophrenic Children", *The Harvard Mental Health Letter*, Feb. 1997.

Garver, David L., "Is Schizophrenia a Degenerative or a Developmental Disorder?", *The Harvard Mental Health Letter*, Aug. 1997.

Gethert, et al., "Structural Instability of a Constitutively Active G Protein-coupled Receptor", *J. Biological Chemistry*, (Jan. 31, 1997) 272(5):2587-2590.

Goldberg, et al., "Cognitive Loss in Schizophrenia", *The Harvard Mental Health Letter*, Apr. 1991.

Griffon, et al., "Antipsychotics with inverse agonist activity at the dopamine D$_3$ receptor", *J. Neural Transmission*, (1996) 103:1163-1175.

Groteweil, et al., "Receptors exhibit constitutive activity that is blocked by inverse agonist", *FASEB J.*, (1994) 8:A1319.

Gutkind, et al., "Muscarinic acetylcholine receptor subtypes as agonist-dependent oncongenes", *Proc. Natl. Acad. Sci. USA*, (Jun. 1991) 88:4703-4707.

Hanson, et al., "Comparison of Neurotensin Responses to MDL 100,907, a Selective 5HT$_{2A}$ Antagonist, with Clozapine and Haloperidol", *Brain Research Bulletin*, (1997) 42(3):211-219.

Hartman, et al., "Functional Reconstitution in Situ of 5-Hydroxytryptamine$_{2C}$ (5HT$_{2C}$) Receptors with α$_q$ and Inverse Agonism of 5HT$_{2C}$ Receptor Antagonists", *J. Biological Chemistry*, (Sep. 13, 1996) 371(37):22591-22597.

Himmler, et al., "Functional Testing of Human Dopamine D$_1$ and D$_5$ Receptors Expressed in Stable cAMP-Response Luciferase Reporter Cell Lines", *J. Receptor Research*, (1993) 13(1-4):79-94.

Hudson, et al., "Identification and characterization of a regulated promoter element in the epidermal growth factor receptor gene", *Proc. Natl. Acad. Sci. USA*, (Oct. 1990) 87:7536-7540.

International Search Report for application PCT/US99/21439, mailed on Mar. 17, 2000.

Julius, et al., "The 5HT2 Receptor Defines a Family of Structurally Distinct but Functionally Conserved Serotonin Receptors", *Proc. Natl. Acad. Sci. USA*, (Feb. 1990) 87:928-932.

Kehne, et al., "Preclinical characterization of the potential of the putative atypical antipsycholic MDL 100,907 as a potent 5HT$_{2A}$ antagonist with a favorable NCS safety profile", *JPET*, (1996) 277:968-981.

Labrecque, et al., "Serotonergic Antagonists Differentially Inhibit Spontaneous Activity and Decrease Ligand Binding Capacity of the Rat 5-Hydroxytryptamine Type 2C Receptor in Sf9 Cells", *Molecular Pharmacology*, (1995) 48:150-159.

Lefkowitz, et al., "Constitutive activity of receptors coupled to guanine nucleotide regulatory proteins", *Elsevier Science Publishers*, (Aug. 1993) 14:303-307.

Lefkowitz, Robert J., "Turned on to ill effect", *Nature*, (Oct. 14, 1993) 365:603.

Leysen, et al., Interaction of antipsychotic drugs with neurotransmitter receptor sites in vitro and in vivo in relation to pharmacological and clinical effects: role of 5HT$_2$ receptors, *Psychopharmacology*, (1993) 112:S40-S54.

Meltzer, et al, "VII. Effects of Antipsychotic Drugs on Serotonin Receptors", *Pharmacological Reviews*, (1991) 43(4):587-604.

Milligan, et al, "Inverse agonism: pharmacological curiosity or potential therapeutic strategy?", *TIPS*, (Jan. 1995) 16:10-13.

Newman-Tancredi, et al., "Agonist and Antagonist Actions of (-)Pindolol at Recombinant, Human Serotonin$_{1A}$ (5-HT$_{1A}$) Receptors", *Neuropsychopharmacology*, (1998) 18(5):396-398.

Newman-Tancredi, et al., "Agonist and Inverse Agonist Efficacy at Human Recombinant Serotonin 5-HT$_{1A}$ Receptors as a Function of Receptor:G-protein Stoichiometry", *Neuropharmacology*, (1997) 36(4-5):451-459.

Newman-Tancredi, et al., "Inhibition of the constitutive activity of human 5HT$_{1A}$ receptors by the inverse agonist, spiperone but not the neutral antagonist, WAY 100,635", *British J. Pharmacology*, (1997) 120:737-739.

Ni, et al., "Blockage of 5HT$_{2C}$ serotonin receptors by fluoxetine (Prozac)", *Pharmacology*, (Mar. 1997).

Nilsson, et al., "Inverse Agonism at Dopamine D$_2$ Receptors", *Neuropsychopharmacology*, (1996) 15(1):53-61.

Office Action in U.S. Appl. No. 11/073,313, sent via electronic notification on Apr. 24, 2007.

Office Action in U.S. Appl. No. 10/130,812, mailed on Jul. 12, 2004.

Office Action in U.S. Appl. No. 10/130,812, mailed on Jan. 7, 2005.

Office Action in U.S. Appl. No. 09/413,626, mailed on Feb. 28, 2001.

Office Action in U.S. Appl. No. 08/273,669, mailed on Mar. 6, 1996.

Office Action in U.S. Appl. No. 08/273,669, mailed on Nov. 22, 1996.

Office Action in U.S. Appl. No. 08/954,724, mailed on Mar. 27, 1998.

Office Action in U.S. Appl. No. 08/965,947, mailed on Mar. 27, 1998.

Office Action in U.S. Appl. No. 08/965,947, mailed on Sep. 14, 1998.

Pauwels, et al., "Differentiation Between Partial And Silent 5-HT$_{1Dβ}$ Receptor Antagonists Using Rat C6-glial and Chinese Hamster Ovary Cell Lines Permanently Transfected With A Cloned Human 5HT$_{1Dβ}$ Receptor Gene", *Biochemical Pharmacology*, (1995) 50(10):1651-1658.

Pauwels, et al., "Review: Amino Acid Domains Involved in Constitutive Activation of G-Protein-Coupled Receptors", *Neurobiology*, (1998) 17:109-135.

Samama, et al., "A Mutation-induced Activated State of the β$_2$-Adrenergic Receptor", *J. Biological Chemistry*, (Mar. 5, 1993) 268(7):4625-4636.

Saltzman, et al., "Cloning of the Human Serotonin 5HT2 and 5-HT1c Receptor Subtypes", *Biochemical and Biophysical Research Communications*, (Dec. 31, 1991) 181(3):1469-1478.

Schmidt, et al., "The Role of 5HT$_{2A}$ Receptors in Antipsychotic Activity", *Life Science*, (1995) 56(25)2209-2222.

Shenker, et al., "A constitutively activating mutation of the luteinzing hormone receptor in familial male precocious puberty", *Nature*, (1993) 365:652-654.

Thomas, et al., "Pharmacological Characterisation of [$^{35}$S]-GTPγS Binding to Chinese Hamster Ovary Cell Membranes Stably Expressing Cloned Human 5-HT$_{1D}$ Receptor Subtypes", *J. Receptor & Signal Transduction Research*, (1995) 15(1-4):199-211.

Tiberi, et al., "High Agonist-independent Activity is a Distinguishing Feature of the Dopamine D1B Receptor Subtype", *J. Biological Chemistry*, (Nov. 11, 1994) 269(45):27925-27931.

Wess, et al., "Structural Basis of the Subtype Selectivity of Muscarinic Antagonists: A Study with Chimeric m2/m5 Muscarinic Receptors", *Molecular Pharmacology*, 41:369-374. (Feb. 1992).

Westphal, et al., "Differences in Agonist-Independent and -Dependent 5-Hydroxytryptamine$_{2C}$ Receptor-Mediated Cell Division", *Molecular Pharmacology*, (1996) 49:474-480.

Westphal, et al., "Increased Basal Phosphorylation of the Constitutively Active Serotonin 2c Receptor Accompanies Agonist-Mediated Desensitization", *Molecular Pharmacology*, (1995) 48:200-205.

Westphal, et al., "Reciprocal Binding Properties of 5-Hydroxytryptamine Type 2c Receptor Agonists and Inverse Agonists", *Molecular Pharmacology*, (1994) 46:937-942.

Yamazaki, et al., "A Deletion Mutation within the Ligand Binding Domain is Responsible for Activation of Epidermal Growth Factor Receptor Gene in Human Brain Tumors", *Japanese J. Cancer Res.*, (Aug. 1990) 81:773-779.

Branchek, et al., "[$^3$H]-DOB(4-Bromo-2,5-Dimethoxyphenylisopropylamine) and [$^3$H] Ketanserin Label Two Affinity States of the Cloned Human 5-Hydroxytryptamine$_2$ Receptor", *Molecular Pharmacology*, (Nov. 1990) 38:604-609.

Office Action in U.S. Appl. No. 11/417,083, sent via electronic notification on Sep. 21, 2007.

Office Action in U.S. Appl. No. 11/073,313, sent via electronic notification on Oct. 19, 2007.

\* cited by examiner

DAY 0
- TRANSFECT NIH 3T3 CELLS IN A 10cm PLATE
  5 μg β-GALACTOSIDASE cDNA
  5 μg RECEPTOR cDNA (OR INCORPORATE INTO SAME PLASMID)

DAY 1
- WASH PLATE

DAY 2
- SPLIT INTO 96 WELLS OF A PLATE
- ADD LIGANDS

DAY 5-7
- ADD SUBSTRATE AND DETERGENT
- READ ABSORBANCE OF WELLS

```
      L   Y   C   R   I   Y   R   E   T   E   K   R   T   K   D   L   A   D   L   Q
m5  leu tyr cys arg ile tyr arg glu thr glu lys arg thr lys asp leu ala asp leu gln val --- --- --- --- --- --- --- --- ala --- --- --- --- --- --- tyr --- ---
    --- --- --- --- --- --- --- --- glu --- ala --- --- --- --- --- glu --- ---
    --- --- --- --- --- val ala --- --- --- -•- --- val met --- --- --- ---
    --- --- --- --- --- ala --•- --- --•- -•- --- --- --- --- --- --- ---
    --- --- --- --- --- --- --- --- --- --- --- --- --- --- --- --- --- --- leu
    --- --- gly --- --- --- --- --- val glu --- --- --- asn --- --- --- --- ---
    --- --- trp --- --- --- --•- --- --- --- --- --- --- --- --- --- ala --- ---
    --•- --- trp --- --- --- --- val --- --- --•- --- --- --- --- --- --- ---
```

FIG.8A

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
|   |   |   | x |   |   |   | 0 |   |   | x  |    |    |    | 0  |    | x  |    | 0  |    |    |
| m4 | leu | tyr | ile | his | ile | ser | leu | ala | ser | arg | ser | arg | val | his | lys | his | arg | pro | glu | gly |
| m2 | leu | tyr | trp | his | ile | ser | arg | ala | ser | lys | ser | arg | ile | lys | lys | asp | lys | lys | glu | pro |
| m1 | leu | tyr | trp | arg | ile | tyr | arg | glu | thr | glu | asn | arg | ala | arg | glu | leu | ala | ala | leu | gln |
| m3 | leu | tyr | trp | arg | ile | tyr | lys | glu | thr | glu | lys | arg | thr | lys | glu | leu | ala | gly | leu | gln |
| m5 | leu | tyr | cys | arg | ile | tyr | arg | glu | thr | glu | lys | arg | thr | lys | asp | leu | ala | asp | leu | gln |

FIG.8B

```
val  trp  met      gly val ala val thr      asn thr val met      tyr  leu
val  trp  met      gly val ala val thr      asn thr val          gly
     trp                val ala val glu      ala thr asn          gly
     arg                    ala     val glu                        ala
     arg                    ala     ala                            glu
     gly                    asp     asp                            glu
                            asp     asp
```

FIG.8C

```
his sto sto sto ser asp gln val lys gln asn sto arg sto gly sto val his
his sto ser gln ser asp asp val ile gln met his ser thr tyr pro gly cys
arg sto gly leu asn asn leu val     gly gly his ser arg val pro pro val
phe ser leu     val his     lys     arg     gly ala     gln     thr glu
pro cys ile     met         asp     val             ala
    phe                     asp     asp
    phe                     asp     asp
                                    asp
```

FIG.8D

STRUCTURES OF COMPOUNDS DISCOVERED BY
5HT2A RECEPTOR INVERSE AGONIST SCREENING
"HALOPERIDOL LIKE"
AC121394
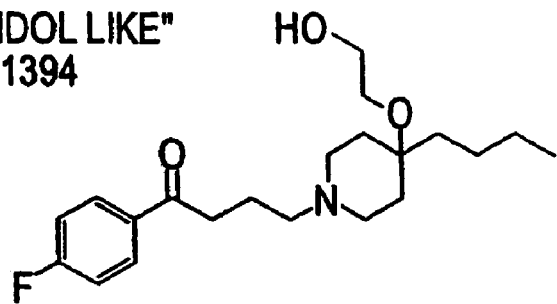
"TRICYCLIC LIKE"
AC116399
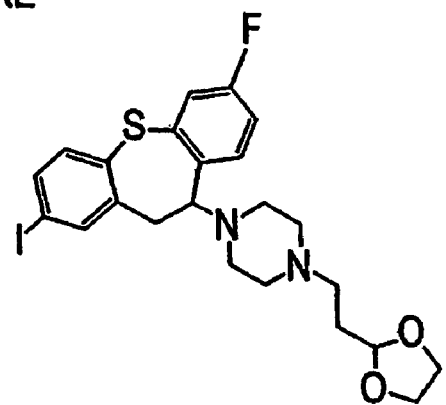
FIG. 21

IDENTIFICATION OF LIGANDS BY SELECTIVE AMPLIFICATION OF CELLS TRANSFECTED WITH A 5HT2A RECEPTOR

RELATED APPLICATIONS

This application is a continuation of U.S. application Ser. No. 10/130,812, by Weiner et al., filed on Nov. 6, 2002, now abandoned, and entitled "METHOD OF IDENTIFYING INVERSE AGONISTS OF THE SEROTONIN 2A RECEPTOR," which in turn claims priority under 35 U.S.C. §371 to the International Application No. PCT/US99/21439, by Weiner et al., filed on Oct. 7, 1999, and entitled "METHOD OF IDENTIFYING INVERSE AGONISTS OF THE SEROTONIN 2A RECEPTOR," which in turn claims priority under 35 U.S.C. § 119/365 to U.S. application Ser. No. 09/413,626, by Weiner et al., filed on Oct. 6, 1999, and entitled "METHOD OF IDENTIFYING INVERSE AGONISTS OF THE SEROTONIN 2A RECEPTOR," now U.S. Pat. No. 6,358,698, issued Mar. 19, 2002, and the U.S. Provisional Application Ser. No. 60/103,317, by Weiner et al., filed on Oct. 7, 1998, and entitled "METHOD OF IDENTIFYING INVERSE AGONISTS OF THE SEROTONIN 2A RECEPTOR," all of which are hereby incorporated by reference herein in their entirety, including any drawings.

FIELD OF INVENTION

The present invention relates to methods for identifying substances that act as ligands for cloned receptors, as well as a test kit for use in the methods. The present invention also relates to methods of identifying compounds which act as inverse agonists of the serotonin 5-HT2A receptor, methods of screening individuals having disorders putatively associated with constitutively active 5-HT2A receptors, diagnostic test kits and methods of treatment for such individuals, methods of decreasing basal activity levels of the 5-HT2A receptor, and uses of inverse agonists as therapeutic agents for schizophrenia and psychosis.

BACKGROUND OF THE INVENTION

Many of the targets for pharmaceutical drug discovery are ligands for receptor proteins, many of which have recently been cloned and pharmacologically characterized. Now that a large number of receptors have been cloned, a major goal of the pharmaceutical industry is to identify ligands for these receptors by screening vast libraries of substances. Unfortunately, with available methods and technology, a major limitation in the drug discovery process is the time and expense required to screen these libraries against so many targets.

The first step in the characterization of ligand interaction with a cloned receptor is to express the receptor in a ligand sensitive form. While a few receptors can be expressed in easily manipulated model systems such as yeast and E. coli, the interactions of ligands with most receptors are influenced by postranslational modifications that are only present in mammalian cells, and many of these receptors require mammalian proteins to accurately transduce their biological effects. Thus for wide applicability, an assay system must be based on expression of cloned receptors in mammalian cells.

The ability of ligands to interact with receptors can be evaluated by competition with a labeled ligand (e.g. radionucleotide) for a binding site on the receptor. Such assays are popular because they involve relatively few steps. Also, since binding often does not require interaction with other cellular proteins, these assays are less sensitive to factors such as levels of expression of the receptor and the cellular environment. Recently, technology such as the Proximity Assay (Amersham Co.) has further simplified these assays making automation and mass screening possible. Binding assays have many limitations: (i) For many technical reasons, binding assays are almost always performed in nonphysiological buffers. These buffers often markedly influence receptor pharmacology. (ii) Agonists and antagonists are not reliably discriminated in binding assays. (iii) Only binding sites for which labeled ligands are available can be studied. (iv) Since only modest levels of receptor (binding site) expression have been achieved in mammalian cells, propagation of receptors is a major expense in these assays. (v) The vast majority of labeled ligands are radioisotopes, the purchase, handling and disposal of which are major expenses.

To reliably discriminate between agonist and antagonist ligands, a response of the receptor must be measured. Responses to agonist activation of receptors are commonly measured as altered activity of various endogenous cellular proteins. Examples include measurement of second messengers such as cAMP (adenylyl cyclase), phosphoinositol metabolism (phospholipase c), tyrosine phosphorylation, and ion channels. All of these assays require the use of cells and/or cellular preparations that have a high degree of biological integrity, and these assays include many complex and expensive steps (Schlessinger and Ullrich, Neuron 9, 383 (1992); chapters in Molecular Biology of G-protein-coupled receptors, M. Brann, ed., Birkhauser (1992)).

A strategy that has been used to avoid the time and expense of measurement of endogenous proteins is to express conveniently assayed marker proteins that can be controlled by activation of the receptor. For example, receptors that control levels of transcription factors can be assayed using markers whose expression is under the transcriptional control of these factors. While this approach has led to convenient assays of receptors that are known to function as controllers of transcription (e.g. steroid/thyroid hormone receptors, Evans (WO 91/07488); Spanjaard et al. Mol. Endocrinology 7:12-16 (1993)), these assays have proven to have limited utility when applied to cell surface receptors, presumably because of the more modest transcriptional control that these receptors exert. Other than the assays that are based on transcriptional control, no approach has been described to assay receptors via recombinant markers that can be conveniently measured.

Another approach is to express the receptors in specialized cells that have endogenous response mechanisms that allow convenient assay of ligand activation of the receptor. Two examples include the RBL cells and melanophores. In RBL cells, muscarinic receptors that stimulate phospholipase c enhance the release of the enzyme hexosamimidase (Jones et al., FEBS Lett. 289, 47 (1991)), a conveniently measured response. In melanophores (cultured pigment cells) cloned receptors that change cAMP levels alter cellular color, a response that is similarly easily measured (Potenza et al., Anal. Biochem. 206, 315 (1992)). The limitations of these assays are that only certain functional types of receptors can be measured. Also, while the assays are relatively convenient, there are limitations inherent in the endogenous responses and cells that are used.

When exposed to ligands, a wide diversity of receptors are able to alter the pH of the media that is used for cell culture. These pH changes are small in magnitude and require expensive instrumentation for measurement (Cytosensor, Molecular Dynamics Co.). This device is not compatible with other instruments that are used in mass screening (e.g. use of a 96 well plate format) and because samples must be incubated within the instrument for several minutes, there is limited sample throughput.

A theoretical limitation inherent in all of the above assays is the inability to assay a given ligand against more than a few receptors at the same time. For example, radioligand binding assays can only be multiplexed to the extent that different and distinguishable radioisotopes are available (e.g. $^3$H versus $^{125}$I). Because of their limited dynamic range, incompatible assay conditions, and the fact that many receptors cannot be distinguished from one another based on their functional responses, second messenger responses, and most other biochemical effects of receptors, are not at all amenable to multiplexed assay. Similarly, the RBL assay, melanophore assay, and Cytosenor pH assays, are only applicable to assay of a single receptor at a time.

Another cellular response that is shared by many receptors is the ability to alter cellular growth. NIH 3T3 cells are a fibroblast cell line that has been extensively used to evaluate the activity of large diversity of gene products that control cell growth, and a number of receptors are able to control the activity of these cells when stimulated by individual ligands. Examples include nerve growth factor (NGF) which stimulates growth only when these cells have been transfected with trk A receptors (NGF receptor) (Cordon-Cardo et al., Cell 66:173-183 (1992); Chao, Neuron 9:583-593 (1992)), carbachol (a muscarinic agonist) stimulates cells transfected with certain muscarinic receptors (Gutkind et al., Proc. Natl. Acad. Sci. USA 88, 4703 (1991); Stephens et al., Oncogene 8, 19-26 (1993)), and nonpinephrine stimulates cells transfected with certain a adrenergic receptors (Allen et al., Proc. Natl. Acad. Sci. USA 88, 11354 (1991)). After long-term stimulation with agonist ligands, the cells change a number of characteristics including cellular growth, loss of contact inhibition, and formation of macroscopic colonies called foci. The ability to induce foci in NIH 3T3 cells is a common characteristic of cancer-associated genes (oncogenes).

The ability of receptors and other gene products to stimulate growth and induce foci in NIH 3T3 cells correlates with the stimulation of individual second messenger systems. Trk A receptors stimulate tyrosine phosphorylation (tyrosine kinase receptor), and many other genes that stimulate tyrosine phosphorylation stimulate growth and focus production in NIH 3T3 cells (Schlessinger and Ullrich, Neuron 9, 383 (1992)). Certain muscarinic (Gutkind et al., Proc. Natl. Acad. Sci. USA 88, 4703 (1991)), adrenergic (Allen et al., Proc. Natl. Acad. Sci. USA 88, 11354 (1991)) and serotonergic (Julius et al., Science 244, 1057 (1989)) receptors that stimulate phospholipase c, also stimulate growth and focus formation in NIH 3T3 cells. In the case of the muscarinic receptors, the ability to stimulate foci and phospholipase c have exactly the same dose/response characteristics, suggesting that these responses may be used as assays for ligand interactions. Unfortunately, these assays offer few advantages to the approaches described above. Focus assays involve a response that requires at least two weeks of cell culture, and are confounded by qualitative changes in patterns of growth. Direct measurement of cellular growth has also been used to measure effects of ligands. The most commonly used assay is $^3$H-thymidine incorporation (Stephens et al., Oncogene 8, 1993, pp. 19-26). These assays are neither convenient nor inexpensive to perform.

Schizophrenia is a devastating neuropsychiatric disorder that affects approximately 1% of the human population. It is characterized by a constellation of symptoms: "positive" symptoms such as hallucinations and delusions; and "negative" symptoms such as social and emotional withdrawal, apathy, and poverty of speech. The disorder usually develops early in life and is characterized by a chronic, often relapsing remitting course. Although the pathophysiology of this clinically heterogeneous disorder is unknown, genetic factors play a significant role. It has been estimated that the total financial cost for the diagnosis, treatment, and lost societal productivity of individuals affected by this disease exceeds 2% of the gross national product (GNP) of the United States. To date, there exist no definitive diagnostic tests for this disorder. Current treatment options available to psychiatrists primarily involve pharmacotherapy with a class of drugs known as antipsychotics. Antipsychotics are effective in ameliorating positive symptomotology, yet they frequently do not improve negative symptoms, and significant, treatment-limiting side effects are common.

Drugs that possess antipsychotic properties have been in clinical use since the early 1950's. The first compound shown to possess this property was chlorpromazine, and many of the subsequent compounds were derived from this phenothiazine antipsychotic. Currently, nine major classes of antipsychotics have been developed and are widely prescribed to treat psychotic symptoms irrespective of their etiology. Clinical use of these compounds are limited, however, by their side effect profiles. Nearly all of the "typical" or older generation compounds have significant adverse effects on human motor function. These "extrapyramidal" side effects, so termed due to their effects on modulatory human motor systems, can be both acute and chronic in nature. Acute effects include dystonic reactions, and a potentially life threatening but rare symptom constellation, neuroleptic malignant syndrome. Chronic side effects include akathisias, tremors, and tardive dyskinesia, a movement disorder characterized by involuntary writhing movements of the tongue and oral musculature seen with long-term administration of these agents. Due in large part to these disabling side effects, drug development in this class of compounds has been focused on newer "atypical" agents free of these adverse effects.

Various hypotheses have been proposed concerning the pathophysiology of schizophrenia, including genetic, environmental, and developmentally based theories. Current neuropharmacological theories are based, in large part, on the observation that antipsychotic drugs can improve the symptoms of schizophrenia, coupled with our current knowledge as to the mechanism of action of this class of drugs. Antipsychotic drugs have been shown, by both in vitro and in vivo methods, to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes.

The prevailing theory as to the mechanism of action of antipsychotic drugs involves antagonism of dopamine D2 receptors. This is based on the observation that these drugs have high affinity for this receptor in vitro, and that a correlation exists between their potency to block D2 receptors and their clinical efficacy. Unfortunately, it is likely that antagonism of dopamine D2 receptors also mediates the disabling extrapyramidal side effects. Interestingly, some antipsychotic drugs have been shown not to possess high affinity for D2 receptors, and therefore an alternate mechanism must be responsible for their clinical effects. The only other consistent receptor interaction that these drugs as a class display is antagonism of 5-HT2A receptors, suggesting that antagonism of these receptors is an alternate molecular mechanism that confers antipsychotic efficacy.

The observation that many of these drugs are antagonists of 5-HT2A receptors has led investigators to postulate that schizophrenia might be caused by heightened or exagerrated signal transduction through serotonergic systems. This theory is bolstered by a number of basic scientific and clinical observations regarding serotonergic systems and the 5-HT2A receptor in particular. Firstly, in addition to the known antipsychotics in widespread clinical usage, research compounds (e.g. ritanserin) that selectively block 5-HT2A receptors (with respect to D2 receptors) have also been shown to possess antipsychotic activity. Secondly, the 5-HT2A receptor mRNA and protein have been shown to be expressed in neural systems that mediate higher cognitive and affective functions, including the cerebral cortex, hippocampus, and amygdala. Thirdly, some of the positive symptoms that characterize the disease can be mimicked in normal individuals by the ingestion of the hallucinogenic indolamine lysergic acid diethylamide (LSD). It is known that LSD and similar hallucinogens exert their psychogenic effects, in part, through the activation of 5-HT2A receptors. G-protein coupled neurotransmitter receptors (GPCR's), including the 5HT2A receptor, function as transducers of intercellular communication. Traditionally, these receptors have been assumed to exist in a quiescent state unless activated by the binding of an agonist (a drug that activates a receptor). When activated, receptors interact with G-proteins, resulting in the generation, or inhibition of, second messenger molecules such as cyclic AMP, inositol phosphates, and diacylglycerol. These second messengers then modulate the function of a variety of intracellular enzymes, including kinases and ion channels, which ultimately determine neuronal excitability and neurotransmitter release.

Over the last few years some fundamental observations have been made relating to ways in which these receptor molecules function. One of the most important of these has been the identification and characterization of constitutively active receptors. It is now appreciated that many, if not most, of the GPCR monoamine receptors can exist in a partially activated state in the absence of their agonists. This increased basal activity can be inhibited by a class of drugs aptly named inverse agonists, in that they function as the inverse of agonists. Inverse agonists differ mechanistically from classic (or neutral) antagonists. Antagonists compete against agonists and inverse agonists for access to the receptor, but do not possess the intrinsic ability to inhibit elevated basal or constitutive receptor responses.

Multiple lines of experimental evidence support the hypothesis that constitutively active neurotransmitter receptors may exist in the central nervous system and be causative for human neuropsychiatric disease. Constitutive activity has been observed with neurotransmitter receptors mutated in vitro. For instance, S. Cottechia et al. (Proc. Natl. Acad. Sci. USA 87, 1990, pp. 2896-2900) made constitutively active chimeric α-1 adrenergic receptor by replacing the third intracytoplasmic loop of the receptor with that of the β-2 adrenergic receptor. Also, P. Samama et al. (J. Biol. Chem. 268, 1993, pp. 4625-4636) generated a constitutively active $O_2$ receptor by replacing four amino acid residues in the C-terminal region of the third intracytoplasmic loop with analogous residues from the α-1B receptor. Point mutations have been introduced into the muscarinic m5 receptor by random saturation mutagenesis (E. S. Burstein et al., Biochem. Pharmacol. 51, 1996, pp. 539-544; T. A. Spalding et al., J. Pharm. Exp. Ther. 275, 1995, pp. 1274-1279), resulting in more than 40 mutants that exhibit varying degrees of constitutive activity. The relative ease with which these receptors may be mutated to a constitutively active form suggests that constitutively active receptors may occur spontaneously in nature with a high frequency.

A strong argument for the potential contribution of constitutively active receptors to human neuropsychiatric disease would be the finding that similar mutations are causative in other human diseases. Mutations in the G-protein coupled receptor gene family are common and are increasingly recognized to cause a number of human diseases. Most of these mutations are single nucleotide or point mutations that alter the structure and function of the receptor molecules. For instance, point mutations in the receptors rhodopsin and vasopressin (J. Nathans, Cell 78, 1994, pp. 357-360; W. Rosenthal et al., Nature 359, 1992, pp. 233-235) cause reading frame shifts, prematurely terminating translation of these proteins, resulting in non-functioning receptors that subsequently cause color blindness and nephrogenic diabetes insipidus, respectively. Robinson and colleagues (P. R. Robinson et al., Neuron 9, 1992, pp. 719-725) characterized the first mutation in a human G-protein coupled receptor that resulted in constitutive activation of the receptor and caused human disease. They found that when the amino acid Lys296 was mutated to Glu in the visual pigment rhodopsin, it was able to activate the G-protein transducin in the absence of light (its natural "agonist"). This particular mutation causes a particularly severe phenotype of retinitis pigmentosa (T. J. Keen et al., Genomics 11, 1991, pp. 199-205).

The number of constitutively active receptors that cause human disease is expanding. Multiple endocrinological and oncological disorders are caused by mutations that give rise to constitutively active receptors. These mutations have been shown to occur as a result of both spontaneous somatic events and as inherited germ line defects. A single point mutation in the luteinizing hormone receptor (Asp578-Gly), which causes male-linked precocious puberty, has been shown to be familial in caucasian populations (A. Shenker et al., Nature 365, 1993, pp. 652-654) and sporadic in Japanese populations (K. Yano et al., J. Clin. Endocrin. Metab. 79, 1994, pp. 1818-1823). Two different point mutations in the parathyroid hormone receptor confer constitutive activity and cause Jansen's metaphyseal chondroplasia (E. Schipani et al., New Eng. J. Med. 335, 1996, pp. 708-714; E. Schipani et al., Science 268, 1995, pp. 98-100). Furthermore, two activating mutations were found in the thyrotropin receptor, both of which were found to cause many sporadic thyroid adenomas (J. Parma et al., Nature 365, 1993, pp. 649-651). Taken together, these data attest to the widespread biological significance of constitutively active receptors and their role in human disease. It is, therefore, highly likely that constitutively active G-protein coupled receptors exist in the human nervous system and mutations in these neurotransmitter receptors, including the 5-HT2A receptor, may cause human neuropsychiatric disease.

Constitutive activity has been described for a growing number of G-protein coupled neurotransmitter receptors. The dopamine D2 receptor has been reported to be constitutively active, and some antipsychotic compounds have been described as inverse agonists, although many of these compounds appear to be classical antagonists (Nilsson, C. L., et al., Neuropsychopharmacology 15, 1996, pp. 53-61; Hall, D. A. and Strange, P. G., Brit. J. Pharm., 121, 1997, pp. 731-736) Similarly, of the thirteen known serotonin receptor subtypes, only three have been shown to possess constitutive activity, the 5-HT1A, 5-HT1D and 5-HT2C receptors. For example, E. L. Barker et al. (J. Biol. Chem. 269, 1994, pp. 11687-11690) describe an in vitro assay in which the wild-type 5-HT2C receptor displays constitutive activity. They further report that certain classically defined antagonists of the receptor, actually act as inverse agonists.

The creation of an activated 5-HT2A receptor by mutagenesis was recently described (Egan, C., T., et., al., J. Pharm Exp. Ther. 286(1), 1998, pp. 85-90). Altering amino acid 322 from the wild type cysteine to lysine, glutamate, or arginine created activated 5-HT2A receptor mutants. This amino acid was chosen because it is analogous to the activating mutation produced in the a1b receptor (Kjelsberg, M. A., et al., J. Biol. Chem. 267(3), 1992, pp. 1430-1433). The activated 5-HT2A receptor displayed measurable constitutive activity, and six antipsychotics were shown to be inverse agonists (Egan, C. T., ibid.; and Egan, C. T., et al., Annals N.Y. Acad. Sci., 1999, pp. 136-139). These authors were unable to measure the constitutive activity of the wild type receptor in their assay, and an insufficient number of clinically relevant compounds comprising the various chemical classes of antipsychotics were tested. This precluded the authors from recognizing the significance of 5-HT2A receptor inverse agonism and efficacy as an antipsychotic.

SUMMARY OF THE INVENTION

It is an object of the present invention to provide an improved method for identifying ligands for cloned receptors.

It is another object of the present invention to provide a method for identifying ligands by simultaneous screening of compounds for activity at multiple cloned receptors.

It is a further object of the present invention to provide a method for measuring ligand concentrations by activity at cloned receptors.

It is still further object of the present invention to provide a method for employing recombinant signaling molecules to facilitate assay of ligands for additional cloned receptors.

It is a still further object of the present invention to provide a method to identify DNAs encoding receptors for ligands.

It is a still further object of the present invention to provide a method to identify mutant forms of receptors that have altered ligand dependence.

Accordingly, the present invention relates to a method of detecting a substance capable of acting as a ligand, the method comprising, (a) incubating, under conditions permitting cell amplification, cells transfected with DNA coding for a receptor capable of influencing cell amplification in response to a ligand, the cells comprising a marker of cell amplification, with a test substance which is a potential agonist or antagonist of the receptor, and (b) after a period of time sufficient to permit cell amplification, determining the presence or absence of amplification of cells containing the marker relative to cells not containing the marker.

In the method of the invention, a mixture of transfected and nontransfected cells will typically be present in step (a). When a test substance is added to the mixture, its ability to act as a ligand for the receptor of interest is determined in terms of its ability to confer a competitive advantage on the cells in the mixture which are expressing that receptor, relative to the cells which do not express the receptor. For example, as a rule, whether in vivo or in vitro, a cell population expressing a receptor will respond positively to a ligand by an overall enhancement of cell function, one aspect of which may be increase in growth rate, or loss of contact inhibition. Applying this observation to the practice of the present method, in vitro, all cells in a culture are essentially in competition with each other; when cells expressing the receptor of interest (transfected cells) are stimulated by a ligand, the enhanced function of the stimulated cells will permit them to flourish at the expense of the nonstimulated (nontransfected) cells. Thus, if the ligand being tested is an agonist of the receptor, the transfected cells in the mixture will be preferentially amplified in response to the agonist, in comparison with nontransfected cells. In other words, the transfected cell population will expand at a greater rate than will the nontransfected cells. In the present method, the transfected cells are distinguishable from the nontransfected cells in the mixed population by the presence of a marker in the transfected cells. Only when the transfected cells have been stimulated by the test ligand will the amplification signal (the marker) accumulate.

When the ligand is an antagonist, the action can be determined similarly, but in reverse, i.e., the cells containing the marker will be at a competitive disadvantage relative to the untransfected cells, the population of which will expand at a greater rate than the transfected cells. However, it is preferred that the assay for antagonists be conducted in the presence of an agonist, and the observed effect is a decrease in the amplification response brought about by the presence of the stimulatory ligand alone.

In another aspect, the present invention relates to a test kit for detecting a substance capable of acting as a ligand, the kit comprising, (a) frozen cells transfected with DNA coding for a receptor capable of influencing cell amplification in response to a ligand, the cells comprising a marker of cell amplification, (b) a medium for growing the cells, (c) a reagent for detecting the presence and quantity of the marker.

This test kit is useful for an embodiment of the present method in which the ligand activity of the test substance (or potentially a large number of test substances) is determined by means of a single receptor (the embodiment of method of the invention termed the Single Receptor Format below).

In a further aspect, the present invention relates to a test kit for detecting a substance capable of acting as a ligand, the kit comprising, (a) frozen cells transfected with DNA coding for a first receptor capable of influencing cell amplification in response to a ligand, the cells comprising a marker of cell amplification, (b) frozen cells transfected with DNA coding for a second receptor capable of influencing cell amplification in response to a ligand, the second receptor being distinct from the first receptor, the cells comprising a marker of cell amplification, (c) a medium for growing the cells, (d) a reagent for detecting the presence and quantity of the marker.

This test kit is useful for an embodiment of the present method in which the ability of the test substance (or potentially a large number of test substances) to act as a ligand to a specific receptor is determined by incubation of the test substance with at least two receptors, and potentially a large number of receptors simultaneously (the embodiment of method of the invention termed the Multiple Receptor Format below).

The present method represents a significant improvement over the screening assays of the prior art. Typically, the known "growth" assays require direct observation of increase of receptor expression, and are generally quantitiative, e.g., results are quantitatively determined by the incorporation of a radiolabeled reagent over a period of time as an indicator of cell growth. In many cases, such as focus assays, the indicator of cell growth, i.e., focus formation, sought in the assay may take several weeks to develop. In addition, it is common that distinct test cell and control cell lines have to be established before screening ligands can begin; consistency of results is difficult to achieve when working with separately cultured cell lines. Such assays are thus not only time consuming, but also quite costly. In contrast, the present assay is essentially qualitative: ligand-induced enchanced cell function of those cells expressing the receptor is determined by observation of amplification of the transfected cell polulation relative to the untransfected cell population from the same culture. The amplification is readily confirmed by the observation of the enhanced expression of a marker gene (e.g., an enzyme which produces a visually detectable product when reacting with its substrate) in the transfected cells. Separate control cell lines are not necessary, and the results are observable within a matter of a few days.

Since 5-HT2A receptors may be critical mediators of antipsychotic drug activity, and as the exact nature of this interaction (antagonism vs. inverse agonism) is poorly understood, many antipsychotic compounds have been tested for their functional activity at this receptor. It has surprisingly been found that the 5-HT2A receptor is constitutively active in the assay described in the present specification, and that nearly all antipsychotic drugs are inverse agonists of this receptor. The striking correlation between antipsychotic efficacy and inverse agonism of the 5-HT2A receptor argues that inverse agonism of this receptor is a fundamental molecular mechanism of action of this class of drugs. This observation has practical applications in the development of novel antipsychotic agents with more favorable side effect profiles as well as potentially broader efficacy against the negative symptomotology of psychotic disorders. This finding also has important implications for the pathophysiology, diagnosis and management of schizophrenia and related psychoses.

Accordingly, the present invention relates in one aspect to a method of identifying a compound which acts as an inverse agonist of the 5-HT2A receptor, the method comprising contacting a constitutively active 5-HT2A receptor with at least one test compound and determining any decrease in the level of basal activity of the 5-HT2A receptor so as to identify a test compound which is an inverse agonist of the 5-HT2A receptor. In a related aspect, this method is used to identify compounds useful in the treatment of schizophrenia or psychosis.

In another aspect, the invention relates to a method of identifying a mutation in the 5-HT2A receptor gene, the mutation being suspected of conferring constitutive activity on the receptor, the method comprising:

(a) extracting nucleic acid from a biological sample obtained from an individual having a disorder or condition putatively associated with constitutive activity of the 5-HT2A receptor;

(b) preparing cDNA from the extracted nucleic acid;

(c) selecting from the cDNA in step (b) cDNA encoding the 5-HT2A receptor;

(d) transfecting a cell with an expression vector comprising said selected cDNA;

(e) selecting a cell expressing constitutively active 5-HT2A receptor; and (f) sequencing the cDNA in said selected cell to detect the mutation(s).

In a further aspect, the invention relates to a method of diagnosing a disorder or condition, or a susceptibility to a disorder or condition, associated with constitutive activity of the 5-HT2A receptor, the method comprising:

(a) obtaining a biological sample from an individual putatively affected by or susceptible to a disorder or condition associated with constitutive activity of the 5-HT2A receptor;

(b) isolating from said biological sample a nucleic acid sequence encoding said receptor, or a portion of said nucleic acid sequence corresponding to the portion of the gene identified to include mutation(s) by the mutation identification method described above; and (c) detecting the presence or absence of the mutation(s) in said nucleic acid sequence or said portion thereof.

The presence of one or more mutations in the nucleic acid sequence may, for example, be detected by sequencing the nucleic acid sequence and comparing it with a sequence known or previously identified to contain mutation(s).

In another aspect, the present invention relates to a test kit for detecting mutation(s) in the gene encoding the 5-HT2A receptor, said mutations giving rise to constitutive activity of the 5-HT2A receptor, the test kit comprising a nucleic acid sequence corresponding to a portion of the gene identified by the mutation identification method described above to include at least one mutation.

Furthermore, the present invention relates to a method of decreasing the basal activity level of the 5-HT2A receptor in a subject in need thereof, the method comprising contacting a 5-HT2A receptor in said subject with an inverse agonist of the 5-HT2A receptor in an amount effective to substantially decrease the level of basal activity of said receptor. In a preferred embodiment, the inverse agonist is selective for the 5-HT2A receptor (i.e., has at least about ten times greater affinity for the 5-HT2A receptor than for at least one other neurotransmitter receptor). In another preferred embodiment, the inverse agonist of the 5-HT2A receptor has little or substantially no anti-dopaminergic activity. In a related aspect, the invention relates to a method of decreasing serotonergic neurotransmission through the 5-HT2A receptor, the method comprising contacting a 5-HT2A receptor with an inverse agonist of the 5-HT2A receptor in an amount effective to substantially decrease the level of basal activity of said receptor.

In another aspect, the present invention relates to a method of ameliorating symptoms of schizophrenia or psychosis in a subject in need thereof, the method comprising administering to the subject a therapeutically effective amount of an inverse agonist of the 5-HT2A receptor.

In yet other aspects, the invention relates to use of an inverse agonist of the 5-HT2A receptor for the preparation of a medicament for substantially decreasing the basal activity level of a constitutively active 5-HT2A receptor. Preferably, in this use, the inverse 5-HT2A agonist is selective for the 5-HT2A receptor. In another embodiment relating to such use, the inverse agonist of the 5-HT2A receptor has little or substantially no anti-dopaminergic activity. The invention also relates in certain aspects to use of a 5-HT2A receptor to identify compounds acting as inverse agonists at said receptor, as well as use of a 5-HT2A receptor to identify a compound acting as an inverse agonist at said receptor and useful in the treatment of schizophrenia or psychosis.

The present disclosure represents the first reported measurement of the constitutive activity of the wild type (non-mutated) human 5-HT2A receptor and correlation of the molecular property of inverse agonism at this receptor with antipsychotic efficacy. Since most mutations in GPCR's have been shown to alter their binding and coupling characteristics, the ability to measure intrinsic activity at the wild type receptor, and to use this receptor in assay for drug discovery is critical.

Inverse agonists of the 5-HT2A receptor, as identified by the present methods, may be used to alleviate or treat disorders or conditions associated with constitutive activity of the 5-HT2A receptor. It is anticipated that compounds that are inverse agonists of the 5-HT2A receptor will be less likely to cause extrapyramidal side effects than many of the typical antipsychotics in current use. In particular, compounds that are selective for the 5-HT2A receptor, in that they exhibit little or no anti-dopaminergic activity, are expected to have fewer extrapyramidal side effects. Furthermore, inverse agonists may be useful in the alleviation or treatment of the negative symptoms of schizophrenia. This is supported by the fact that some of the "atypical" antipsychotics, which are described herein to act as inverse agonists at the 5-HT2A receptor, have been reported to have beneficial effects on negative symptoms.

Definitions

In the present description and claims, the following terms shall be defined as indicated below.

A "test substance" or "test compound" is intended to include any drug, compound or molecule with potential biological activity.

A "ligand" is intended to include any substance that either inhibits or stimulates the activity of a receptor. An "agonist" is defined as a ligand increasing the functional activity of a receptor (i.e. signal transduction through the receptor). An "antagonist" is defined as a ligand decreasing the functional activity of a receptor either by inhibiting the action of an agonist or by its own activity.

A "receptor" is intended to include any molecule present inside or on the surface of a cell, which molecule may effect cellular physiology when either inhibited or stimulated by a ligand. Typically, receptors which may be used for the present purpose comprise an extracellular domain with ligand-binding properties, a transmembrane domain which anchors the receptor in the cell membrane and a cytoplasmic domain which generates a cellular signal in response to ligand binding ("signal transduction"). In some cases, e.g. with adrenergic receptors, the transmembrane domain is in the form of up to several helical, predominantly hydrophobic structures spanning the cell membrane and part of the transmembrane domain has ligand-binding properties.

"Constitutive activity" is defined as the elevated basal activity of a receptor which is independent of the presence of an agonist. Constitutive activity of a receptor may be measured using a number of different methods, including cellular (e.g., membrane) preparations (see, e.g., A. J. Barr and D. R. Manning, J. Biol. Chem. 272, 1997, pp. 32979-32987), purified reconstituted receptors with or without the associated G-protein in phospholipid vesicles (R. A. Cerione et al., Biochemistry 23, 1984, pp. 4519-4525), and functional cellular assays (described herein).

An "inverse agonist" is defined as a compound which decreases the basal activity of a receptor (i.e., signal transduction mediated by the receptor). Such compounds are also known as negative antagonists.

An "antagonist" is defined as a compound which competes with an agonist or inverse agonist for binding to a receptor, thereby blocking the action of an agonist or inverse agonist on the receptor. However, an antagonist (also known as a "neutral" antagonist) has no effect on constitutive receptor activity.

The "5-HT2A receptor" is defined as the human serotonin receptor subtype characterized through molecular cloning and pharmacology as detailed in Saltzman, A G., et al., Biochem. Biophys. Res. Comm. 181(3), pp. 1469-1478; and Julius, D., et al., Proc. Natl. Acad. Sci. 87, pp. 928-932.

A "tyrosine kinase receptor" is intended to include any receptor that has intrinsic tyrosine kinase enzymatic activity.

A "tyrosine phosphatase receptor" is intended to include any receptor that has intrinsic tyrosine phosphatase enzymatic activity.

A "chimeric receptor" is intended to include any combination of two or more receptors where the functional "signal transducing" component of one receptor is fused to the ligand binding component of another receptor.

A "chimeric G-protein" is intended to include any combination of two G-proteins where the effector binding component of one G-protein is fused with the receptor binding component of another G-protein.

"Gq-i5" is defined as chimeric G-protein consisting of the G-protein Gq in which the five amino acids of the C-terminus are replaced with the C-terminal five amino acids of Gi.

"Gi" is intended to include any G-protein which when activated inhibits the enzyme adenylyl cyclase.

"Gq" is intended to include any G-protein which when activated stimulates the enzyme phospholipase c.

"Gs" is intended to include any G-protein which when activated stimulates the enzyme adenylyl cyclase.

A "G-protein-coupled receptor" is intended to include any receptor that mediates signal transduction by coupling with a guanine nucleotide binding protein.

A "G-protein" is defined as any member of the family of heterotrimeric, signal transducing guanine nucleotide binding proteins.

"Signal transduction" is defined as the process by which information from ligand binding to a receptor is translated into physiological change.

An "oncogene" is defined as any gene that is able to stimulate focus formation in NIH 3T3 cells in the absence of any ligand. These genes are often associated with cancerous tumors.

A "transcription factor" is defined as any substance that is able to alter the transcription of a given gene. These factors are often proteins that bind to regions of DNA which modify the activity of a promoter.

"Transfection" is defined as any method by which a foreign gene is inserted into a cultured cell.

A "biological sample" indicates a sample of tissue or body fluid obtained from a subject. Biological samples relevant to obtaining 5-HT2A receptors include, but are not limited to, blood, serum (5-HT2A receptors being present in platelets) and/or brain tissue, within which the receptor genes are known to be expressed in identical forms.

A "marker" is defined as any substance that can be readily measured and distinguished from other cellular components. The marker may be the transfected receptor DNA, the transcribed receptor mRNA, an enzyme, a binding protein or an antigen.

A "cell" useful for the present purpose is one which has the ability to respond to signal transduction through a given receptor by cellular amplification.

An "aliquot" is defined as a portion of transfected cells provided on a solid support, e.g. a microtiter plate, test tube or microbead.

"Amplification" is intended to indicate the growth of receptor-transfected cells, in particular relative to the growth of non-receptor-transfected cells.

"Altered growth characteristics" is intended to indicate enhanced or decreased growth of receptor-transfected cells relative to non-receptor-transfected cells (background) cultured together with transfected cells. Cells incubated with an agonist will typically respond by enhanced growth or, in some cases, formation of foci on the culture plate. Cells incubated with an antagonist will typically respond by decreased growth.

The term "subject" refers to an animal, preferably a mammal, most preferably a human, who is the object of treatment, observation or experiment.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated.

The terms "selectivity" or "selective," when used in the context of inverse agonists of 5-HT2A, are used to indicate compounds having at least approximately 10-fold higher affinity for the 5-HT2A receptor subtype than towards at least one, and preferably more than one, other neurotransmitter receptor.

$EC_{50}$ for an agonist is intended to denote the concentration of a compound needed to achieve 50% of a maximal response seen in R-SAT. For inverse agonists, $EC_{50}$ is intended to denote the concentration of a compound needed to achieve 50% inhibition of an R-SAT response from basal, no compound, levels.

Utility

The present invention is based on the ability of certain receptors to modulate cellular growth in a ligand-dependent fashion. The present method may be employed in two formats. In the Single Receptor Format which is particularly applicable to the detailed pharmacology of a single receptor, the ability of ligands to selectively induce the growth of receptor-transfected cells has been linked to induction of convenient markers. The Multiple Receptor Format which is applied to the assay of potential ligands against a large number of receptors simultaneously, utilises the ability of ligands to selectively induce markers that are unique to individual receptors in cultures which are mixtures of cells transfected with several receptors.

The Single Receptor Format allows the convenient assay of the interaction of agonist and antagonist ligands with individual receptors. The Multiple Receptor Format allows the convenient assay of the interaction of agonist and antagonist ligands with several receptors at the same time.

The Single Receptor Format involves very few steps; no expensive reagents; ability to quantitatively discriminate partial agonists, full agonists, and antagonists. Because the assay relies on transfections of recombinant receptor and marker DNA, the assay can be performed with a wide variety of receptors, markers and cell types. In addition to these properties, the Multiple Receptor Format represents the only method known to the inventor which can be applied to screening for ligand activity against large numbers of receptors simultaneously. Thus, the Multiple Receptor Format is particularly suitable for use in a drug screening programme wherein "hits" (that is, substances with ligand activity) may be identified quickly from among a large number of test substances.

Receptor-based assays can be used to evaluate the concentrations of known ligands. The ligand to be measured may be incubated with transfected cells according to the present method. The major difference between chemical or immunologically based assays, and receptor-based assays is the fact that receptor-based assays measure the functional effect of the ligand. One application of this feature is in pharmacokinetic analysis of compounds. In these assays, receptor-based assays would detect active metabolites that may be missed by chemical or immunological techniques. Receptor-based assays would ignore inactive metabolites. Such data would be very useful in evaluating the role of occupancy of a given receptor in the therapeutic effect of test compounds. Another application of this approach is to identify the pharmacological properties of bodily fluids where drug history is unknown. One such application would be in illicit drug testing. In this case blood could be tested for ability to activate opiate receptors to determine if an individual had consumed one of many opioids.

Another use of the present method could be to newly clone receptors to given ligands from cDNA libraries. Pools of cDNAs from a cDNA library may be screened for activation by a given ligand. Which cDNA in a given pool that encoded a responsive receptor would be identified by transfecting each cDNA in the library until the responsible receptor was identified. The strategy would be analogous to that illustrated in appended FIG. 11, except that unknown cDNAs are used for the transfections.

In a further use of the present method, libraries of a given receptor may be prepared by amplifying a specific gene from several individuals, tumors, tissues, or randomly mutated pools. These libraries of cDNAs can then be screened by transfecting pools of DNAs into cells, and growing the cells in the presence or absence of ligand. This strategy is likely to be particularly powerful when applied to identification of constitutively active versions of receptors (e.g. certain oncogenes).

BRIEF DESCRIPTION OF THE DRAWINGS

FIG. 8A illustrates the sequences within the mutated region of eight functional muscarinic receptors that were each isolated and sequenced from at least two different foci. The sequence of the wild-type m5 receptor (SEQ ID NO:1) is indicated at the top (single and three letter codes) followed by the mutant sequences (SEQ ID NOS:2-9). Base changes that did not alter the encoded amino acid are indicated by an (*), and predicted amino acid changes are indicated with conservative substitutions in plain type and nonconservative substitutions in bold type. Twenty additional unique sequences were isolated from independent foci. For the 28 mutant receptor sequences, an average of 2.4 amino acid changes were observed/receptor. FIG. 8B illustrates a comparison of the sequences of the five wild-type muscarinic receptor subtypes (SEQ ID NOS:10-13). Shading indicates identity or conservative substitutions with respect to the sequence of the m5 receptor (SEQ ID NO:1). Positions where only identical or conservative substitutions are tolerated for all five of the receptor subtypes are indicated by an (°). Positions where nonconservative substitutions that are not related to the functional classification of the receptors (m2/m4 versus m1/m3/m5) are indicated by an (x). Positions where at least the PI-linked muscarinic receptors (m1/m3/m5) are conserved are indicated by an (0). Positions where the substitutions are predictive of functional classification are indicated by an (*, m1/m3/m5 conserved, nonconserved versus m2/m4, and m2/m4 conserved). Boxed residues are conserved with respect to positions where no nonconservative substitutions were identified in the mutated receptors (indicated below the positions indicated in part C). FIG. 8C illustrates a compilation of all amino acid substitutions that were identified in at least two independent foci. Amino acid substitutions are listed below the corresponding amino acid substitution listed in B. Amino acid substitutions are listed once for each independent receptor. Positions of amino acid changes that were observed in at least two foci are indicated below the position of the corresponding wild-type amino acid. These amino acid changes are compiled from the 28 independent mutant receptors isolated from the 675 recombinant library. Positions where no nonconservative substitutions were isolated are boxed. Amino acids where the other muscarinic receptors are conserved with respect to m5 are also included in these boxes. FIG. 8D illustrates a compilation of amino acid substitutions observed in 17 clones selected at random from the mutant receptor library expressed in E. coli. (prior to transfection and selection by transformation of NIH 3T3 cells). An average of 4.2 amino acid substitutions were observed per mutant receptor. The presence of stop codons is indicated (Sto). Conservative substitutions are defined as members of the following groups: S (Set), T(Thr), P(Pro), A(Ala), and G(Gly); N(Asn), D(Asp), E(Glu), and Q(Gln); H(His), K(Lys), and R(Arg); M(Met), I(Ile), L(Leu) and V(Val); F(Phe), Y(Tyr) and W(Trp); or C(Cys).

FIG. 21 shows the chemical structures of two representative compounds identified as inverse agonists of the 5-HT2A receptor using the screening methods of the present invention. Compound AC121394, which is haloperidol-like, and compound AC116399, which is tricyclic-like, were identified out of a library comprising 135,000 structurally diverse organic compounds.

DETAILED DESCRIPTION OF THE INVENTION

Single Receptor Format

Figure 1A:
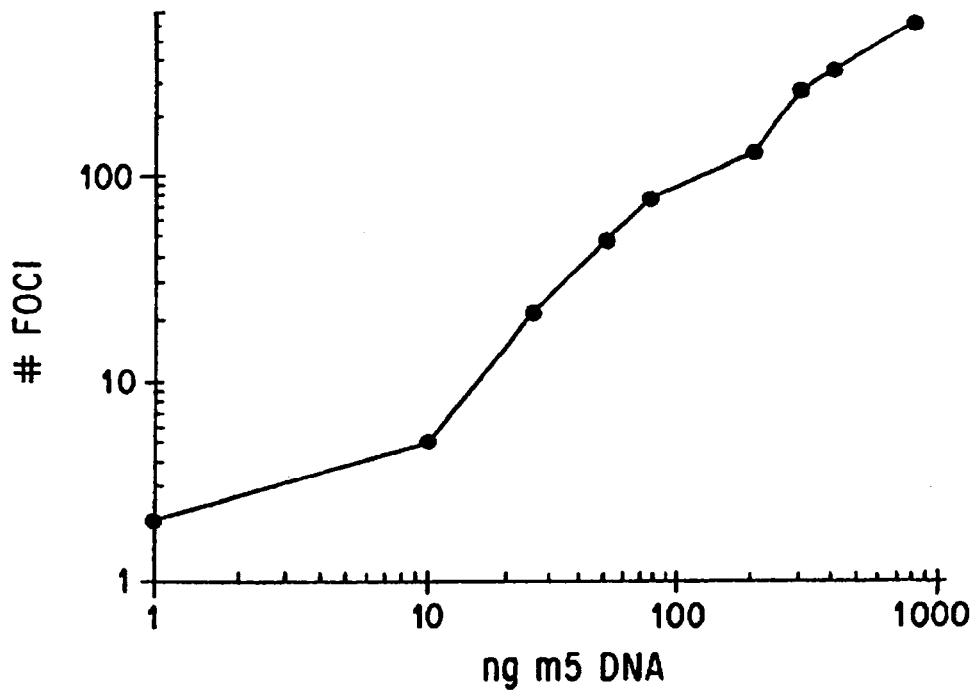
FIG. 1A is a plot of the number of foci vs. concentration of m5 DNA.

In one embodiment of the present method, cells are transfected with DNA encoding a single receptor.

Transfection may be performed according to known methods. In general, a DNA sequence encoding a receptor may be inserted into a suitable cloning vector which may conveniently be subjected to recombinant DNA procedures. The vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the receptor should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the receptor in mammalian cells are the SV40 promoter (Subramani et al., Mol. Cell Biol. 1 (1981), 854-864), the MT-1 (metallothionein gene) promoter (Palmiter et al., Science 222 (1983), 809-814) or the adeno-virus 2 major late promoter.

The DNA sequence encoding the receptor may also be operably connected to a suitable terminator, such as the human growth hormone terminator (Palmiter et al., op. cit.). The vector may further comprise elements such as polyadenylation signals (e.g. from SV40 or the adenovirus 5 E1b region), transcriptional enhancer sequences (e.g. the SV40 enhancer) and translational enhancer sequences (e.g. the ones encoding adenovirus VA RNAs).

The vector may further comprise a DNA sequence enabling the vector to replicate in the host cell in question. An example of such a sequence (when the host cell is a mammalian cell) is the SV40 origin of replication.

The procedures used to ligate the DNA sequences coding for the receptor, the promoter and the terminator, respectively, and to insert them into suitable vectors containing the information necessary for replication, are well known to persons skilled in the art (cf., for instance, Sambrook et al., Molecular Cloning: A Laboratory Manual, Cold Spring Harbor Laboratory, Cold Spring Harbor, N.Y., 1989).

Cells which may be used in the present method are cells which are able to respond to signal transduction through a given receptor by cellular growth. Such cells are typically mammalian cells (or other eukaryotic cells) as cells of lower life forms generally lack appropriate signal transduction pathways for the present purpose. Examples of suitable cells are cells of the mouse fibroblast cell line NIH 3T3 (ATCC CRL 1658) which respond by growth to Gq and tyrosine kinase receptors as well as oncogenes (e.g. ras (cf. Barbacid, Ann. Rev. Biochem. 56, 1987, pp. 779-827) or p53), mutant G proteins (cf. Kalinec et al., Mol. Cell. Biol. 12, 1992, p. 4687); RAT 1 cells (Pace et al., Proc. Natl. Acad. Sci. USA 88, 1991, pp. 7031-7035) which respond to changes in cyclic AMP mediated by Gi and Gs receptors; and pituitary cells (Vallar et al., Nature 330, 1987, pp. 556-558) which also respond to changes in cyclic AMP mediated By Gi and Gs receptors.

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; Neumann et al., EMBO J. 1 (1982), 841-845; and Wigler et al., Cell 11, 1977, pp. 223-232.

The DNA sequence encoding the receptor may encode a tyrosine kinase receptor, such as a colony stimulating factor 1 (CSF-1), platelet-derived growth factor (PDGF), epidermal growth factor (EGF), transforming growth factor (TGF), nerve growth factor (NGF), insulin, insulin-like growth factor 1 (IGF-1) receptor, etc.; a G-protein coupled receptor, such as a Gi-coupled, Gq-coupled or Gs-coupled receptor, e.g. a muscarinic receptor (e.g. the subtypes m1, m2, m3, m4, m5), dopamine receptor (e.g. the subtypes D1, D2, D4, D5), opiate receptor (e.g. the subtypes µ or δ), adrenergic receptor (e.g. the subtypes α1A, α1B, α1C, α2C10, α2C2, α2C4), serotonin receptor, tachykinin receptor, luteinising hormone receptor or thyroid-stimulating hormone receptor (for further information on G-protein coupled receptors, vide M. Brann (ed.), Molecular Biology of G-Protein Coupled Receptors, Birhauser, Boston, 1992).

Receptors that couple to the G-protein Gs may be able to induce β-gal when expressed with a chimera between Gs and Gq (eg. Gq-s5). Alternatively, cells that respond to changes in Gs activity or cAMP could be used instead of the NIH 3T3 cells. Likely candidates are RAT 1 cells where cAMP is known to have significant effects on cellular growth (Pace et al. Proc. Natl. Acad. Sci., 88:7031-7035 (1991)), and certain pituitary cell lines where growth is sensitive to changes in the Gs pathway (Vallar et al. Nature 330:556-558 (1987)). A third possibility is to prepare chimeric receptors such that the ligand binding domain of a given Gs-coupled receptor is fused with the G-protein coupling domain of a Gq coupled receptor. Such chimeras have been reported for m1 muscarinic (Gq) and β-adrenergic receptors (Wong et al. J. Biol. Chem. 265:6219-6224 (1990)).

Several receptors have recently been identified that do not have intrinsic tyrosine kinase activity, but are able to stimulate the activity of tyrosine kinases endogenous to various cells including NIH 3T3 cells. One example is the GM-CSF receptor which induces foci in NIH 3T3 cells when activated by ligand (Areces et al. Proc. Natl. Acad. Sci. USA 90:3963-3967 (1993)). Like the tyrosine kinase receptors, these receptors may be assayed by the present method.

Recently, several receptors have been identified which have intrinsic tyrosine phosphatase activity. For use in the present method, tyrosine phosphatase receptors may be co-expressed together with a tyrosine kinase receptor. It is likely that these receptors could reverse tyrosine phosphorylation by tyrosine kinase receptors, and thus inhibit signals mediated by these receptors.

Transcription factors may be assayed by constructing vectors where the DNA binding target of a transcription factor is engineered to control the expression of a gene that stimulates cellular growth. Thus, if a ligand were to suppress the function of the transcription factor (or compete for the DNA binding site), expression to the growth controlling gene would be suppressed (Spanjaard et al. Mol. Endocrinology 7:12-16 (1993)).

Receptors of the retinoic acid/steroid super family of receptors could be assayed by preparing chimeras between the ligand binding portions of these receptors, with proteins that stimulate cellular growth by acting as transcription factors. Chimeras between the glucocorticoid receptors and the oncogene c-fos allow glucocorticoids to stimulate foci in NIH 3T3 cells (Superti-Furga et al., Proc. Natl. Acad. Sci. USA 88:5114-5118 (1991)).

Many gene products that can induce ligand-independent growth may also be conveniently assayed by the present method. Many proteins that induce ligand-independent growth are mutant forms of receptors. Examples include forms of the trk A receptor, mutant forms of EGF receptors, the neu oncogene (Wong et al. Proc. Natl. Acad. Sci. USA 89:2965-2969 (1992); Schlessinger et al. Neuron 9:383-391 (1992)). Also, many of these proteins are mutant forms of signal transducing proteins such as G-proteins (Barbacid Ann. Rev. Biochem. 56:779-827 (1987)). In principle, the advantage of the present method in this application is that general effects of compounds on growth can be distinguished from specific effects on the activity of the oncogene. This may be achieved by measuring overall cell growth and viability of the culture in parallel with the specific marker present in the transfected cells. Since the majority of cells are not transfected, general effects on cell growth must be nonspecific.

It is further envisaged that the receptor may be a ligand- or voltage-gated ion channel. Ligand-gated channels include subtypes of nicotinic acetylcholine receptors, GABA receptors, glutamate receptors (NMDA or other subtypes), subtype 3 of the serotonin receptor or the cAMP-regulated channel that causes cystic fibrosis. Voltage-gated ion channels include subtypes of potassium, sodium, chloride or calcium channels (cf. Lester, Science 241, 1988, p. 1057; Nicoll, Science 241, 1988, p. 545). To assay these channels, cells may be incubated under ionic conditions where activation (or inactivation) of the channel will yield a net change in ion flow. The cells could be genetically modified to increase the effect of changing intercellular ion channel concentration on cell amplification. For example, calcium channels may be assayed by co-transfecting the desired channel with an oncogene which is sensitive to calcium levels.

According to the present method, any agonist activity of the test substance may be determined by an enhanced effect of the receptor on growth of the receptor-transfected cells relative to a background of cells which have not been transfected with the receptor. Although an enhanced effect may be measured as either an increase or decrease in growth, the enhanced effect of the receptor in the presence of an agonist is most usually detected as enhanced amplification of the receptor-transfected cells.

According to the present method, any antagonist activity of the test substance may be determined by inhibition of the effect of the receptor on growth of the transfected cells relative to a background of cells which have not been transfected with the receptor. Although an inhibition of the effect may be measured as either an increase or decrease in growth, the inhibition of the effect of the receptor is typically detected as an inhibition of amplification of the receptor-transfected cells. In a particular embodiment, the test substance is incubated with the transfected cells in the presence of an agonist of receptor stimulation of cell amplification. Inhibition of cellular amplification by the agonist shows the presence of an antagonist.

In the transfected cells, the marker may be the transfected receptor DNA or the transcribed receptor mRNA. The presence of receptor DNA or mRNA may be determined by DNA amplification and/or hybridisation techniques.

For hybridisation purposes, DNA may be isolated from the cells and digested with a suitable restriction endonuclease. After digestion, the resulting DNA fragments may be subjected to electrophoresis on an agarose gel. DNA from the gel may then be blotted onto a nitrocellulose filter and hybridised with a radiolabelled oligonucleotide probe. The probe may conveniently contain a DNA fragment of the receptor gene (substantially according to the method of E. M. Southern, J. Mol. Biol. 98, 1975, pp. 503).

For amplification purposes, total mRNA isolated from the cells may be reverse transcribed to prepare a cDNA library. cDNA encoding the receptor may then be amplified by polymerase chain reaction (PCR) using oligonucleotide primers corresponding to segments of the gene coding for receptor in question and detected by size on an agarose gel. Amplified receptor cDNA may also be detected by hybridisation to a radiolabelled oligonucleotide probe comprising a DNA sequence corresponding to at least part of the gene encoding the receptor. This method is described by, e.g., Sambrook et al., supra.

The marker may also be an enzyme, a binding protein or an antigen. In this case, the cells are transfected with a DNA sequence encoding the marker in question.

Examples of enzymes useful as markers are phosphatases (such as acid or alkaline phosphatase), β-galactosidase, urease, glucose oxidase, carbonic anhydrase, acetylcholinesterase, glucoamylase, malate dehydrogenase, glucose-6-phosphate dehydrogenase, β-glucosidase, proteases, pyruvate decarboxylase, esterases, luciferase, alcohol dehydrogenase, or peroxidases (such as horseradish peroxidase).

To visualize enzyme activity in the present method, a substrate must be added to catalyse a reaction the end product of which is detectable. Examples of substrates which may be employed in the method according to the invention include o-nitrophenyl-β-D-galactopyranoside, 5-bromo-4-chloro-3-indolyl-β-D-galactopyranoside, chloronaphthole, o-phenylenediamine, 3-(p-hydroxyphenyl) propionic acid, luminol, indoxyl phosphate, p-nitrophenylphosphate, nitrophenyl galactose, 4-methyl umbelliferyl-D-galactopyranoside, $H_2O_2$/tetramethylbenzidine or luciferin.

Examples of binding proteins which may be used in the present method are avidin or streptavidin which may be detected with labelled biotin. Suitable sustances for labelling biotin may be fluorescent tags (e.g. fluorescein, phycoerythrin, phycocyanin) or marker enzymes (for instance one of the enzymes mentioned above). Other possible binding proteins are lectins, in particular plant lectins such as lentil lectin or wheat lectin. Lectins may be visualised by means of carbohydrates capable of binding to the respective lectins. Such carbohydrates may be labelled with the same substances as described above for biotin.

Examples of antigens which may be used in the present method are HLA or c-myc. Antigens may be visualised by means of labelled antibodies reactive with the respective antigens. The antibodies may be labelled with the same substances as those described above for biotin.

The marker is preferably an enzyme, in particular β-galactosidase encoded by the *E. coli* lacZ gene, or firefly luciferase. The DNA encoding the marker enzyme may be present on the vector which carries the receptor DNA, or it may be present on a separate vector which is then co-transfected with the vector carrying the receptor DNA.

In a particularly preferred embodiment of the single receptor format, the present method comprises (a) transfecting cells with DNA encoding the receptor and with DNA encoding a marker enzyme, (b) dividing the transfected cells into several identical aliquots, (c) incubating each aliquot with one or more test substances for a period of time sufficient to distinguish between stimulated and non-stimulated receptors, and (d) determining any change in cell growth by measuring marker enzyme activity in each aliquot.

To control for non-specific effects on cell growth in step (d), the amount of marker enzyme expressed by stimulated cells may be compared to the amount of a second and easily distinguishable marker enzyme expressed by non-transfected cells mixed into the culture before addition of the test substance. The advantage of using two different enzymes as markers according to the method of the invention is that the time needed to distinguish between stimulated and non-stimulated cells is relatively brief. There is no need to wait for several days until foci have formed on a culture plate and, in practical terms, the distinction can be made before it is necessary to change the medium in the plates. Furthermore, if the enzyme reaction is chromogenic or luminescent, no separation of substrate is required before detection.

Figure 2A:
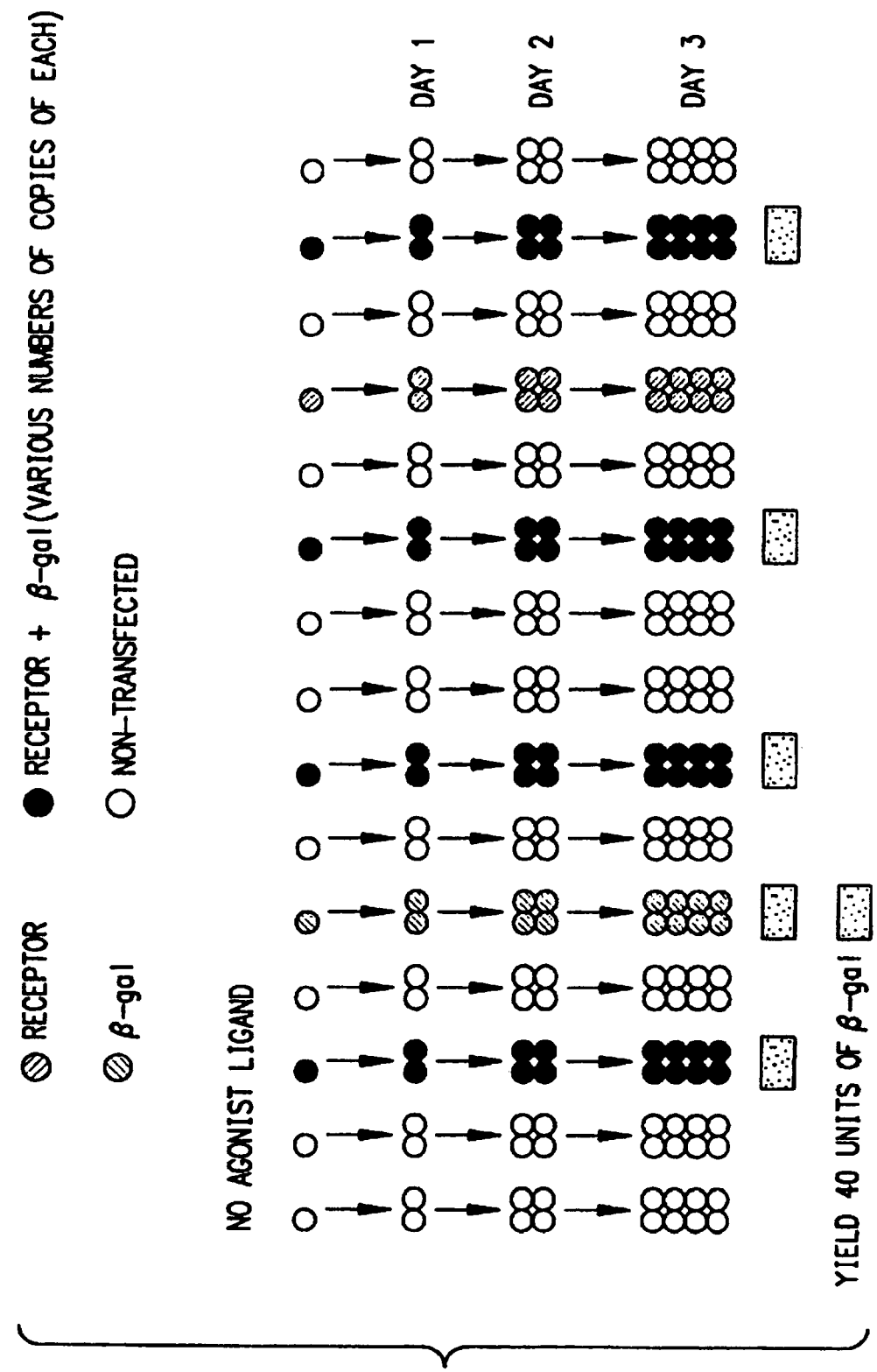
FIG. 2 is a schematic drawing of the Single Receptor Format, where agonist induction of receptor is detected as β-galactosidase activity. Receptor DNA and β-galactosidase DNA are co-transfected using a high concentration of both DNA's, conditions where the majority of cells that are successfully transfected will be transfected with both DNA's. Using the calcium phosphate precipitation procedure described below, only a minority of cells in the culture will be transfected. In the illustrated example, cells divide once a day, and the presence of an agonist ligand doubles the rate of division (*) of cells transfected with the receptor.
Figure 2B:
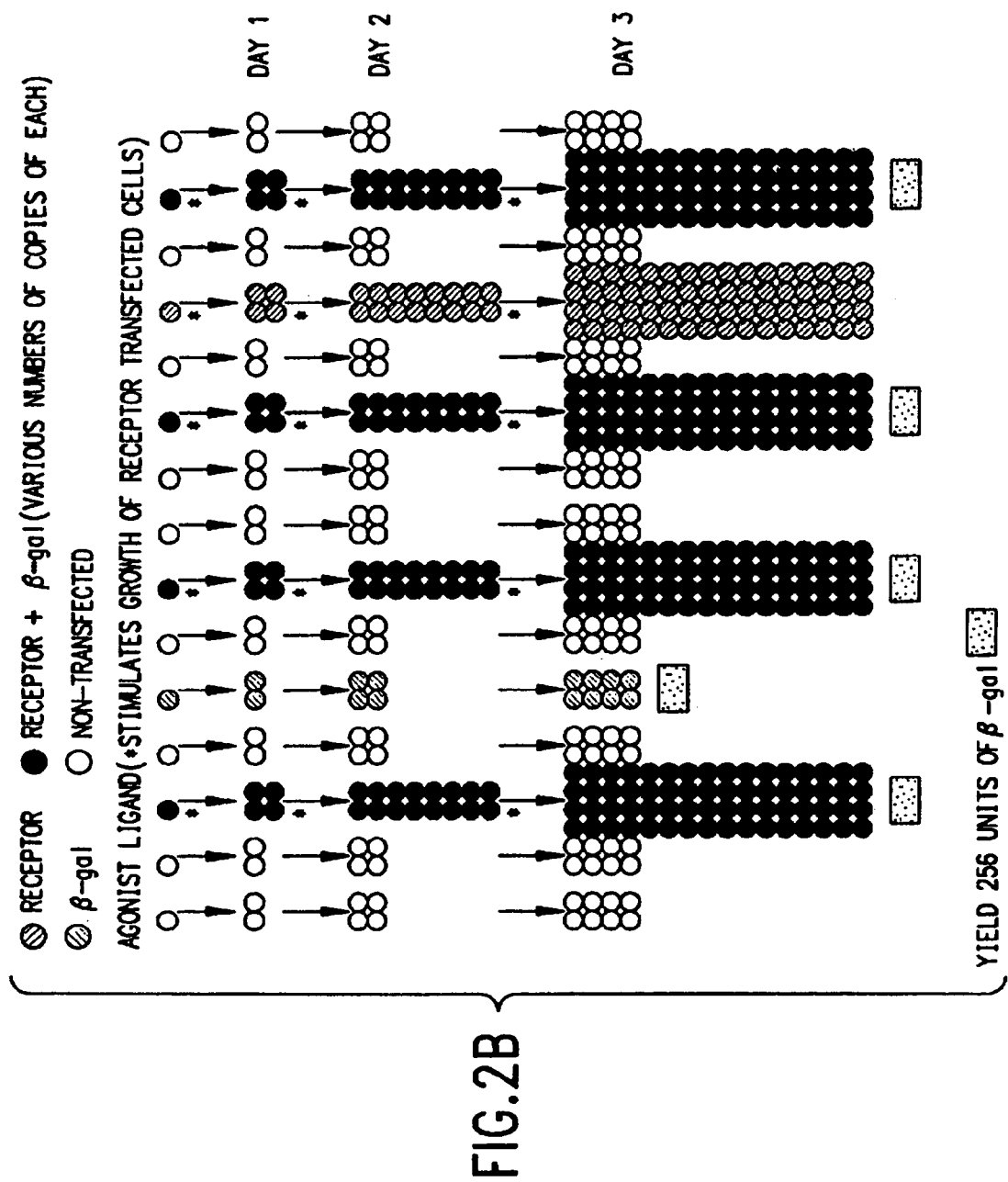

FIG. 2 is a schematic representation of a strategy for using cell growth as a convenient assay of ligand interaction with a single receptor. A high concentration of receptor DNA and a convenient marker DNA (eg. DNA coding for β-galactosidase) are used to transfect NIH 3T3 cells using calcium phosphate precipitation. Alternatively, the receptor and marker could be incorporated into the same plasmid. Using these conditions, a minority of cells would actually be transfected, and the majority of transfected cells will express both DNAs. In cultures that are grown in the absence of any ligand, all of the cells would have similar growth characteristics, and in theory the amount of marker found in the culture after a given time in culture would be proportional to the percentage of cells that were initially transfected with the marker. If the cells are incubated in the presence of a ligand that stimulates the receptor (agonist), the receptor-transfected cells will have a positive growth advantage relative to other cells in the culture. Since the majority of receptor-transfected cells also express the marker, then the amount of marker will be increased in the final cultures.

Multiple Receptor Format

In another embodiment of the present method, the cells are transfected with DNAs encoding two or more distinct receptors, each transfected cell expressing an individual receptor. This should be taken to mean that statistically each cell has been transfected with one individual receptor only. This may be obtained by using only small amounts of receptor DNA for transfection so that the DNA encoding any one particular receptor constitutes only a small percentage of the total DNA used for transfection, for instance by using carrier DNA or by transfecting the cells simultaneously with a number of different receptor DNAs. In the latter case, very few of the cells will be transfected with more than one receptor DNA although it cannot be excluded that other receptor DNAs may also be present in minor quantities in some of the cells. However, only the cells containing a receptor stimulated by the particular ligand added to the cells will be amplified according to the method (and thus become visible in the assay). As an alternive to this procedure, separate cell cultures may be transfected with each of the receptors and subsequently mixed before addition of the test substance(s).

Transfection procedures are otherwise as described above for the single receptor format. Likewise, the receptor types used for transfection are the same as indicated above. Because the strength of responses are related to signal transduction type, the best results would be obtained by testing receptors of the same class together, e.g. Gq-coupled receptors such as α1A, B and C adrenergic receptors, m1, m3 and m5 muscarinic receptors, S2 and 1c serotonin receptors; Gi-coupled receptors such as m2 and m4 muscarinic receptors, D2 and D4 dopamine receptors, 1e and 1d serotonin receptors; trk A, B and C receptors, EGF and PDGF receptors; adenosine receptors, α2 adrenergic receptor subtypes, somatostatin receptors, opiate μ and δ receptors; oncogenes such as ras, p53, neu oncogenes, or oncogenic forms of the trk, EGF, PDGF, etc., receptors.

Suitable markers are described above. However, it may be particularly advantageous to include different markers in the method of the invention such that cells expressing a given receptor also express a marker which is distinguishable from a marker expressed by cells transfected with another receptor (to make it easier to distinguish between the different receptors). To be distinguishable, enzymatic markers should not overlap in their substrate specificities (e.g. alkaline phosphatase and β-galactosidase). The substrates and detection mechanisms should therefore be selected for assays that can be distinguished (e.g. alkaline phosphatase to give a black reaction product and β-galactosidase to give a yellow reaction product). Alternatively, chromogenic and luminescent detection may be combined (e.g. β-galactosidase and firefly luciferase). In this case, the reactions may easily be distinguished because β-galactosidase yields a chromogenic product when reacted with o-nitrophenyl-β-D-galactopyranoside, while luciferase yields a luminescent product when reacted with luciferin. Luminescent reactions have the added advantage of yielding a labile product (light). Thus, several luminescent enzymatic reactions may be performed sequentially in the same reaction mixture.

In one particularly preferred embodiment of the multiple receptor format, the present method comprises (a) transfecting cells with DNAs encoding two or more distinct receptors, each transfected cell expressing an individual receptor, and with DNA encoding a marker enzyme, (b) dividing the transfected cells into several identical aliquots, (c) incubating each aliquot with one or more test substances for a period of time sufficient to distinguish between stimulated and non-stimulated receptors, (d) determining any change in cell growth by measuring marker enzyme activity in each aliquot, identifying active ligands by their ability to alter cell growth characteristics, and (e) identifying which receptor is activated by the ligand by subjecting each receptor to the method described above in steps (a)-(d) of the Single Receptor Format.

In another particularly preferred embodiment of the multiple receptor format, the present method comprises (a) transfecting cells with DNAs encoding two or more distinct receptors, each transfected cell expressing an individual receptor, and with DNA encoding a marker enzyme, (b) dividing the transfected cells into several identical aliquots, (c) incubating each aliquot with one or more test substances for a period of time sufficient to discriminate between stimulated and non-stimulated receptors, (d) determining any change in cell growth by measuring marker enzyme activity in each aliquot, identifying active ligands by their ability to alter cell growth characteristics, and (e) identifying which receptor is activated by the ligand by assaying the receptor DNA and/or mRNA by DNA amplification and/or hybridisation techniques.

In yet another particularly preferred embodiment of the multiple receptor format, the present method comprises (a) transfecting cells with DNAs encoding two or more distinct receptors, each transfected cell expressing an individual receptor, and with DNAs encoding two or more marker enzymes, such that cells expressing a given receptor express a marker which is distinguishable from a marker expressed by cells transfected with another receptor, (b) dividing the transfected cells into several identical aliquots, (c) incubating each aliquot with one or more test substances for a period of time sufficient to distinguish between stimulated and non-stimulated receptors, (d) determining any change in cell growth by measuring marker enzyme activity in each aliquot, identifying active ligands by their ability to alter cell growth characteristics, and (e) identifying which receptor is activated by the ligand by adding a substrate for each individual marker enzyme followed by assay.

These embodiments of the present invention are based on the principle that if instead of a series of mutant versions of a single receptor, multiple receptor types were transfected together and grown in the presence of a ligand, a large number of receptors and possibly also potential ligands could be tested simultaneouly, thus saving time in a drug screening programme. The receptor or receptors that the ligand is able to activate would lead to an amplification of cells that express that receptor, and thus the receptors that are activated by a given ligand could be identified in the culture, for instance by DNA amplification techniques.

Figure 10:
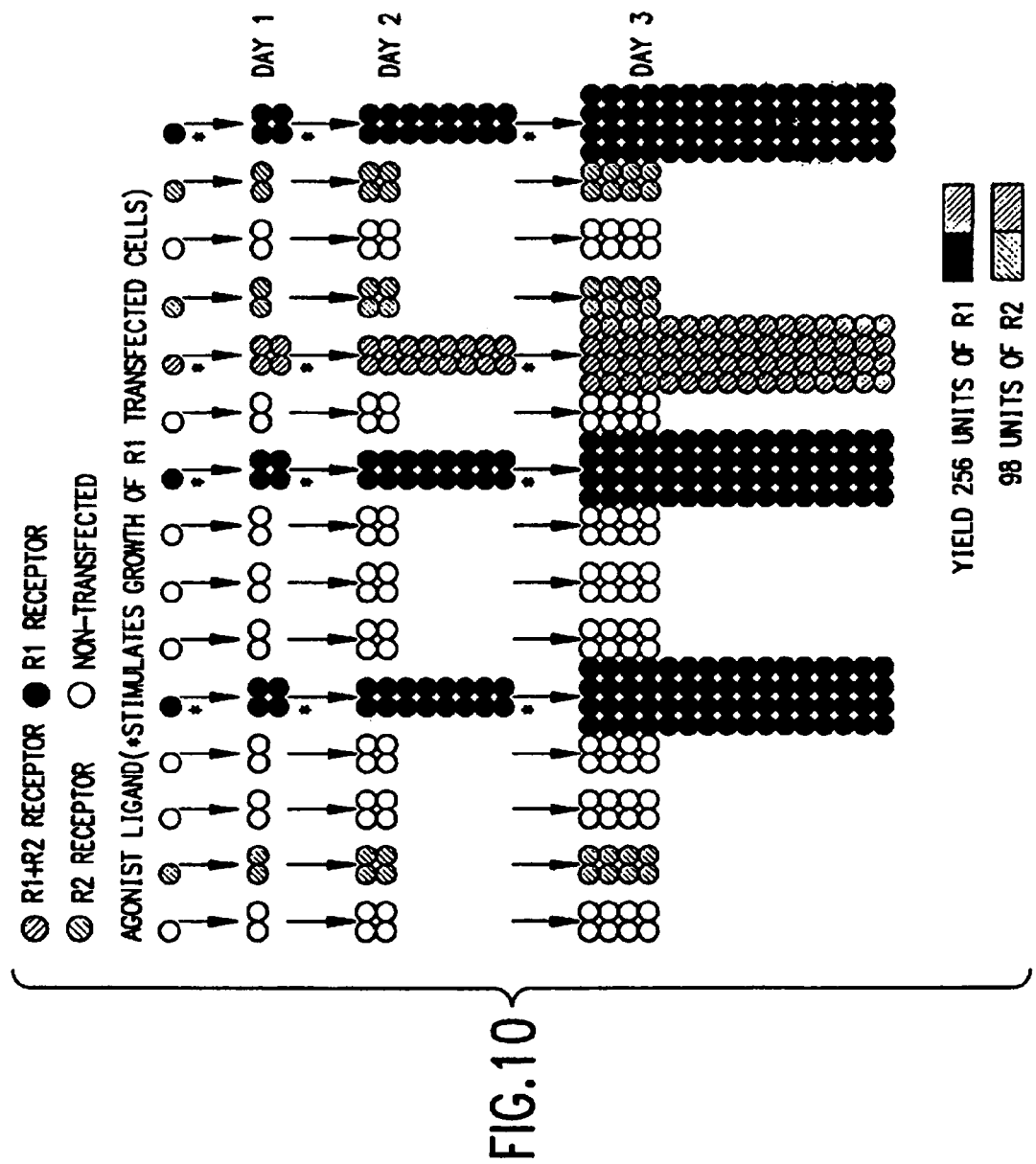
FIG. 10 is a schematic drawing of an example of the Multiple Receptor Format. In this example, a low concentration of two receptor DNA's (R1 and R2) are used for transfection. Under these conditions, very few of the cells will be simultaneously transfected with R1 and R2. Thus a R1 ligand will selectively amplify R1-expressing cells.

A number of configurations of the Multiple Receptor Format are technically feasible. FIG. 10 presents the general concept of the Multiple Receptor Format. Here two receptors are transfected into NIH 3T3 cells using low concentrations of receptor DNA. Under these conditions a minority of cells would be transfected, and those that are transfected will normally only express a single receptor. Rarely, both receptors will be expressed in a given cell. If the culture is grown in the presence of ligand with agonist activity against R1 then R1 transfected cells will be amplified in the culture. For the cells where R2 was also expressed with R1 then some R2 will also be amplified. The amount of receptor amplification could be determined by having distinguishable markers expressed on each of the receptor plasmids, or alternatively by detecting the receptor (SEQ ID NO:14) mRNA of DNA directly by means of DNA amplification techniques.

Figure 11:
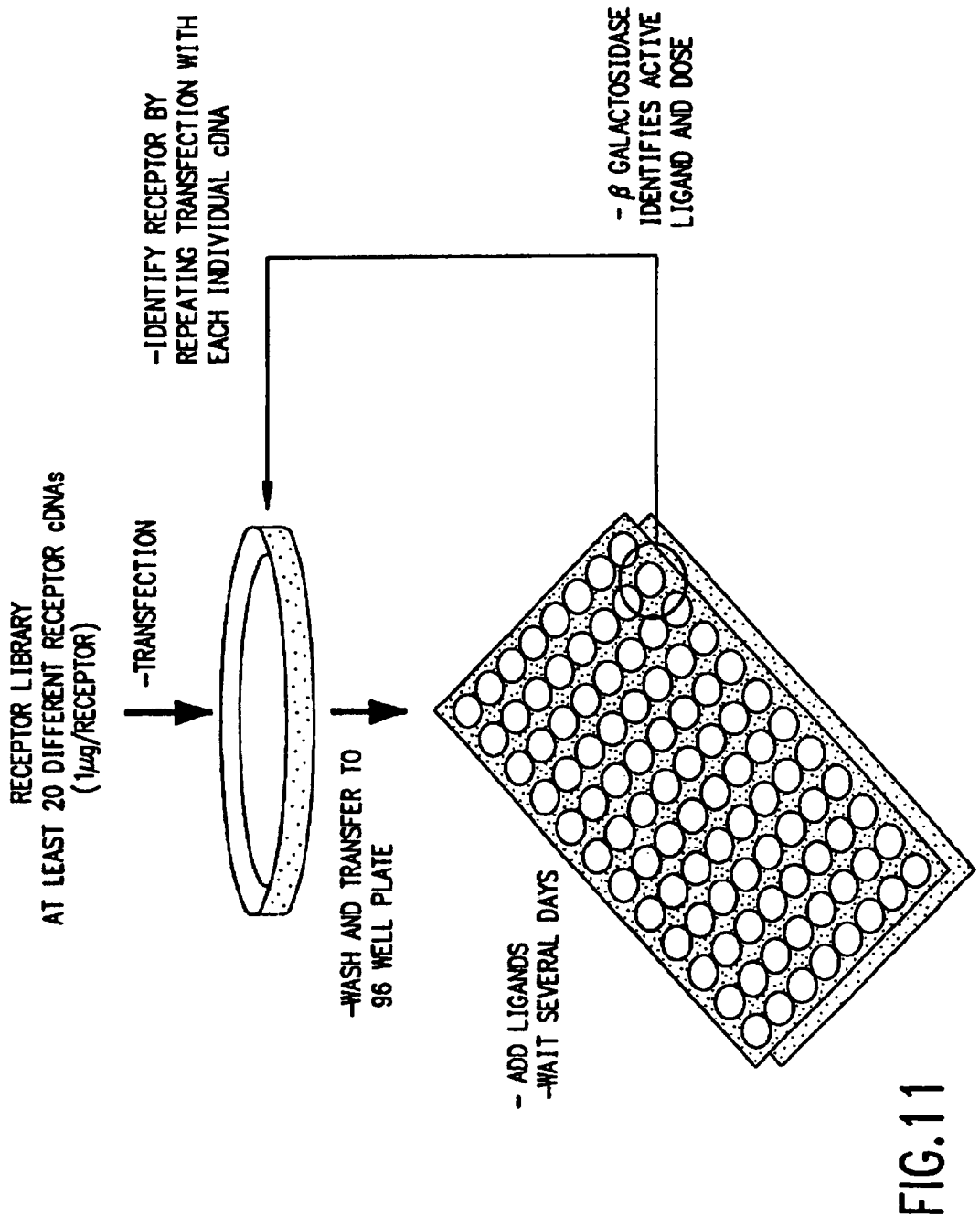
FIG. 11 is a schematic drawing of an embodiment of the Multiple Receptor Format where several receptors are assayed simultaneously using only β-gal assays.
Figure 14:
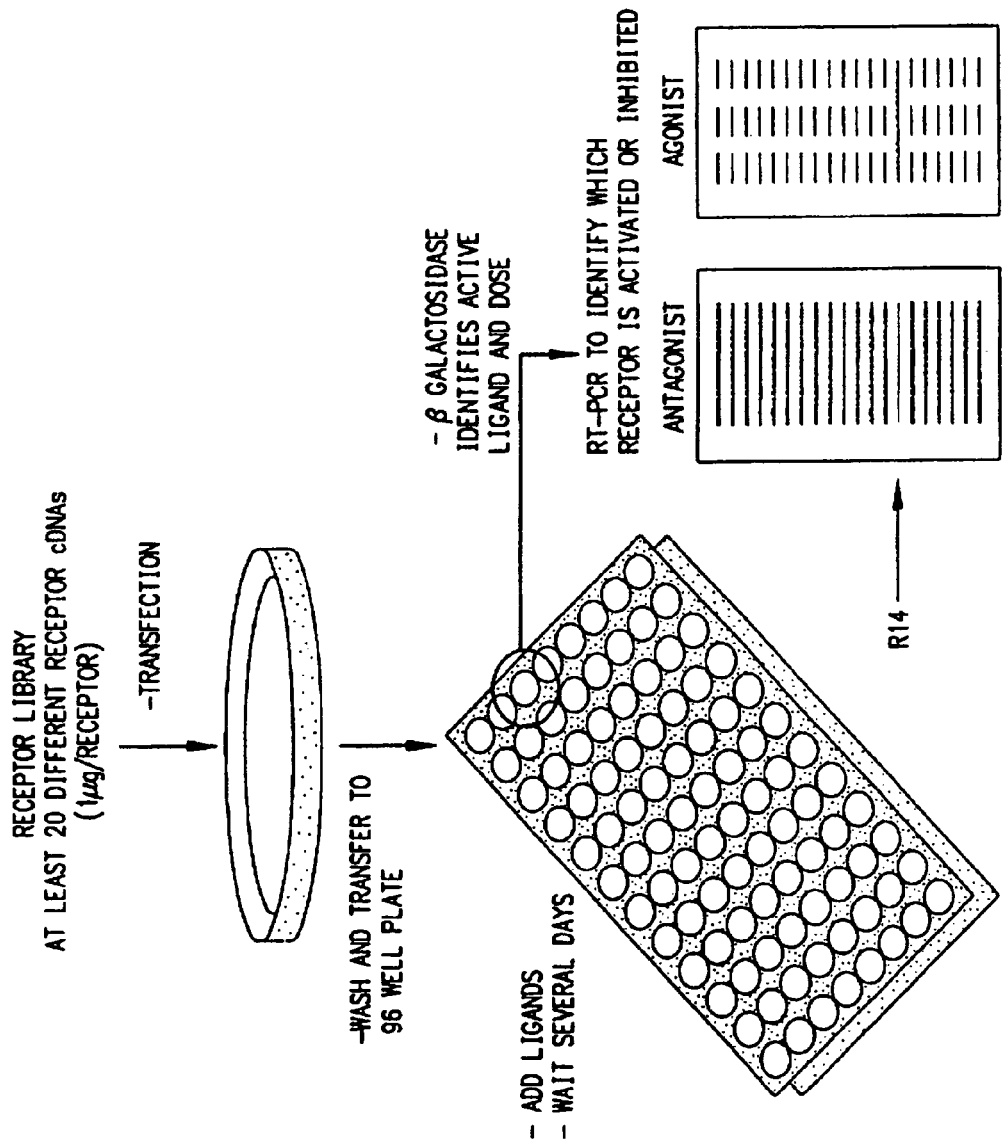
FIG. 14 is a schematic drawing of an embodiment of the Multiple Receptor Format where several receptors are assayed simultaneously using a combination of β-galactosidase and DNA amplification assays.

One configuration of the Multiple Receptor Format is illustrated in FIG. 11. Here multiple receptors are co-expressed with a single marker. Activation of one or more of the receptors will result in induction of the marker, and identify the test ligand as having activity. Which of the receptors was activated could then be determined by screening against each receptor in isolation. This approach should have utility in mass screening of compounds for ligand activity against multiple receptor targets. An alternative approach to identifying which receptor was activated would be to measure receptor mRNA and/or DNA by DNA amplification techniques as illustrated in FIG. 14. The latter approach is likely to have considerable utility in the analysis of ligands as either antagonist or as inhibitors of receptors that have intrinsic activity (e.g., oncogenes).

In one embodiment, a method of identifying a compound which acts as an inverse agonist of the 5-HT2A receptor comprises contacting a constitutively active 5-HT2A receptor with at least one test compound and determining any decrease in the level of basal activity of the 5-HT2A receptor so as to identify the test compound(s) which act as inverse agonists of the 5-HT2A receptor. This method may be used to identify compounds useful in the treatment of schizophrenia or psychosis.

In a preferred embodiment, a method of identifying a compound which acts as an inverse agonist of the serotonin 5-HT2A receptor comprises:

(a) culturing cells which express a constitutively active 5-HT2A receptor;

(b) incubating the cells with at least one test compound; and (c) determining any decrease in basal activity level of the 5-HT2A receptor so as to identify a test compound which is an inverse agonist of the 5-HT2A receptor.

Where a mutation in the gene encoding the 5-HT2A receptor is suspected of conferring constitutive activity on the receptor, a method of identifying a mutation in the 5-HT2A receptor gene comprises:

(a) extracting nucleic acid from a biological sample obtained from an individual having a disorder or condition putatively associated with constitutive activity of the 5-HT2A receptor;

(b) preparing cDNA from the extracted nucleic acid;

(c) selecting from the cDNA in step (b) cDNA encoding the 5-HT2A receptor;

(d) transfecting a cell with an expression vector comprising said selected cDNA;

(e) selecting a cell expressing constitutively active 5-HT2A receptor; and (f) sequencing the cDNA in said selected cell to detect the mutation(s).

The extracted nucleic acid is preferably RNA, from which cDNA may be prepared by reverse transcription. The cDNA which encodes the 5-HT2A receptor is preferably amplified using oligodeoxynucleotide probes specific to the 5-HT2A receptor gene (i.e., based on the known sequence of the gene).

The present invention also provides a method of diagnosing a disorder or condition, or a susceptibility to a disorder or condition, associated with constitutive activity of the 5-HT2A receptor. This method comprises:

(a) obtaining a biological sample from an individual putatively affected by or susceptible to a disorder or condition associated with constitutive activity of the 5-HT2A receptor;

(b) isolating from said biological sample a nucleic acid sequence encoding said receptor, or a portion of said nucleic acid sequence corresponding to the portion of the gene identified to include mutation(s) by the mutation identification method described above; and (c) detecting the presence or absence of the mutation(s) in said nucleic acid sequence or said portion thereof.

The presence of such mutations in the nucleic acid sequence may, for example, be detected by sequencing the nucleic acid sequence and comparing it with a sequence known or previously identified to contain mutation(s).

The present invention also provides a test kit for detecting mutation(s) in the gene encoding the 5-HT2A receptor, wherein the mutations give rise to constitutive activity of the 5-HT2A receptor. The test kit comprises a nucleic acid sequence corresponding to a portion of the gene identified by the mutation identification method described above to include at least one mutation.

The present invention also provides a method of decreasing the basal activity level of the 5-HT2A receptor in a subject in need thereof. This method comprises contacting a 5-HT2A receptor in said subject with an inverse agonist of the 5-HT2A receptor in an amount effective to substantially decrease the level of basal activity of said receptor. In a preferred embodiment, the inverse agonist is selective for the 5-HT2A receptor. In another preferred embodiment, the inverse agonist of the 5-HT2A receptor has little or substantially no anti-dopaminergic activity.

Transfection of cells in the present invention may be performed according to any of numerous methods known in the art. In general, DNA sequences encoding the 5HT2A receptor may be inserted into suitable cloning vectors which may conveniently be subjected to recombinant DNA procedures. These vectors may be autonomously replicating, i.e., vectors which exist as extrachromosomal entities, the replication of which are independent of chromosomal replication (e.g., plasmids). Alternatively, these vectors may be ones which, when introduced into a host cell, are integrated into the host cell genome and replicate together with the chromosome(s) into which they have been integrated.

The DNA sequences encoding the 5-HT2A receptor may suitably be derived from sample genomic DNA, or cDNA that has been reverse transcribed from sample RNA, in accordance with well-established molecular biological techniques (e.g., as described in Sambrook et al., Molecular Cloning: A Laboratory Manual, 2nd Ed., Cold Spring Harbor Laboratory, Cold Spring Harbor, N.Y., 1989).

When transfected, the DNA sequence encoding the 5-HT2A receptor should be operably connected to a suitable promoter sequence. The promoter may be any DNA sequence which shows transcriptional activity in the host cell of choice and may be derived from genes encoding proteins either homologous or heterologous to the host cell. An example of a suitable promoter is the SV40 promoter (Subramani et al., Mol. Cell Biol. 1, 1981, pp. 854-864).

The DNA sequence encoding the 5-HT2A receptor may also be operably connected to a suitable terminator, such as the human growth hormone terminator (Palmiter et al.). The vector may further comprise elements such as polyadenylation signals (e.g., from SV40 or the adenovirus 5 E1b region), transcriptional enhancer sequences (e.g., the SV40 enhancer) and translational enhancer sequences (e.g., those encoding adenovirus VA RNAs).

The vector may further comprise a DNA sequence enabling the vector to replicate in the host cell in question. An example of such a sequence (when the host cell is a mammalian cell) is the SV40 origin of replication.

The procedures used to ligate the DNA sequences encoding the 5-HT2A receptor, the promoter and the terminator, respectively, and the procedures used to insert them into suitable vectors containing the information necessary for replication, are well known to persons skilled in the art (see, e.g., Sambrook et al., supra).

Cells which may be used in the present method include any cells capable of mediating signal transduction via the 5-HT2A receptor, either via endogenous expression of this receptor (e.g., certain types of neuronal cells lines that natively express the 5-HT2A receptor), or following transfection of cells with plasmids containing the 5-HT2A receptor gene. Such cells are typically mammalian cells (or other eukaryotic cells, such as insect cells or *Xenopus* oocytes), because cells of lower life forms generally lack the appropriate signal transduction pathways for the present purpose. Examples of suitable cells include: the mouse fibroblast cell line NIH 3T3 (ATCC CRL 1658), which responds to transfected 5-HT2A receptors by stimulating growth (described herein); RAT 1 cells (Pace et al., Proc. Natl. Acad. Sci. USA 88, 1991, pp. 7031-7035); and pituitary cells (Vallar et al., Nature 330, 1987, pp. 556-558). Other useful mammalian cells for the present method include HEK 293 cells, CHO cells and COS cells.

Methods of transfecting mammalian cells and expressing DNA sequences introduced in the cells are described in, e.g., Kaufnan and Sharp, J. Mol. Biol. 159, 1982, pp. 601-621; Southern and Berg, J. Mol. Appl. Genet. 1, 1982, pp. 327-341; Loyter et al., Proc. Natl. Acad. Sci. USA 79, 1982, pp. 422-426; Wigler et al., Cell 14, 1978, p. 725; Corsaro and Pearson, Somatic Cell Genetics 7, 1981, p. 603; Graham and van der Eb, Virology 52, 1973, p. 456; Neumann et al., EMBO J. 1, 1982, pp. 841-845; and Wigler et al., Cell 11, 1977, pp. 223-232.

The screening assay used in the present method may include any functional assay that would reflect 5-HT2A receptor activity in, for instance, membrane preparations or living cells, mammalian and non-mammalian, in response to a ligand (agonist, antagonist and, inverse agonists) and, in particular, an assay suited for detecting constitutive activity of receptors. Examples of suitable assay systems include those using insect cells (such as cells of *Spodoptera frugiperda*, Sf9, transfected with baculoviris vector carrying the receptor gene (e.g., as described in A. J. Barr and D. R. Manning, J. Biol. Chem. 272, 1997, pp. 32979-32987; J. L. Hartman and J. K. Northup, J. Biol. Chem. 271, 1996, pp. 22591-22597; J. Labrecque et al., Mol. Pharmacol. 48, 1995, pp. 150-159)), or *Xenopus* oocytes expressing cloned receptors (e.g., as described in Y. G. Ni and R. Miledi, Proc. Natl. Acad. Sci. USA 94, 1997, pp. 2036-2040), or HEK293 cells transiently expressing cloned receptors (e.g., as described in M. Tiberi and M. Caron, J. Biol. Chem. 269, 1994, pp. 27925-27931), or CHO cells (e.g., as described in A. Newman-Tancredi et al., Neuropsychopharmacology 18, 1998, pp. 396-398). A preferred assay is the Receptor Selection and Amplification Technology (R-SAT) assay disclosed in U.S. Pat. No. 5,707,798, the disclosure of which is hereby incorporated by reference in its entirety.

Although the constitutive activity of the 5-HT2A receptor may, in certain assays, be detected in itself, it may be more suitable in other instances to overexpress the receptor to augment basal signaling and improve the sensitivity of detection of inverse agonism. Over-expressiona of receptors in cultured cells, as well as transgenic animals, has been shown to result in increased constitutive activity of the receptor (G. Milligan et al., TIPS 16, pp. 10-13; S. A. Akhter et al. J. Biol. Chem. 272(34), pp. 21253-21259). Over-expression may be experimentally accomplished by using an excess of plasmid DNA encoding receptors when transfecting cells as part of functional assays of cloned monoamine receptor subtypes. The excess of DNA may vary from one assay to the next but may, in the currently preferred assay, be approximately 10-fold in excess of that required to provide measurable signaling.

Attempts have been made to link neurotransmitter receptors to neuropsychiatric diseases, primarily by identifying polymorphisms in the receptor genes by methods including restriction fragment length polymorphism (RFLP), single strand conformational polymorphism (SSCP) and multipoint, parametric and non-parametric methods of linkage analysis. For example, the various dopamine receptors have been shown to possess multiple polymorphic variants in the human population (H. H. M. Van Tol et al., Nature 342, 1992, pp. 149-152; N. Craddock et al., Psychiat. Genet. 5, 1989, pp. 63-65). However, attempts at associating those polymorphisms with neuropsychiatric disease are unlikely to succeed because there is no credible evidence that the polymorphisms have functional significance. Therefore, the present method of identifying mutant receptors represents a substantial advantage in that it identifies only functionally altered mutants. These phenotypically distinct receptors are much more likely to be related to human disease.

Thus, the present diagnostic methods are amenable to screening human populations for mutant 5-HT2A receptor genes that create a constitutively active phenotype. As the human 5-HT2A receptor gene contains introns (A. G. Saltzman et al., supra), amplification of receptor DNA will typically be carried out by reverse transcriptase-based PCR (RT-PCR; e.g., as described in Elion, E. A., Current Protocols in Molecular Biology, 1998; F. M. Ausebel et al., EDS, pp. 3.17.1-3.17.10). This method creates a representative cDNA pool from an individual's RNA that is extracted from suitable samples (e.g., serum or brain tissue) and amplifies the receptor gene using oligonucleotide probes based on the known sequence of the gene. The resulting PCR products are then subcloned into mammalian expression vectors, and competent bacteria such as E. coli are subsequently transformed. Bacterial cultures are inoculated during transformation, thereby ensuring that the DNA isolated from this culture represents a mixture of plasmids that contains copies of both alleles of the amplified 5-HT2A receptor gene. Phenotypic cellular assays (including R-SAT), select for only those cells transfected with plasmids that encode functional receptors, as only these cells will transduce mitogenic signals and continue to grow. If the transfected receptor cDNA harbors a mutation that confers a constitutively active phenotype, this is detectable by the presence of higher levels of basal receptor activity measured in the assay and verified by incubation of these transfected cells with a known inverse agonist (e.g. as described in the Example below).

After a constitutively active 5-HT2A receptor has been identified in the assay, a formal characterization of the mutation responsible for this phenotype is carried out. For example, an aliquot of the original ligation reaction from all patients in whom a constitutively active receptor has been identified by screening is used to re-transform competent bacteria, and individual clones are selected. The individual clones are then grown in larger quantities and plasmid DNA is extracted according to any of various methods known in the art. Restriction enzyme digestions will identify 5-HT2A gene-containing constructs, and a number of these are then subjected to automated DNA sequencing.

Mutant 5-HT2A receptors, identified by the present method, may be included in a test kit for detecting mutation(s) in the gene encoding the 5-HT2A receptor. Such a test kit may conveniently comprise a nucleic acid sequence corresponding to a portion of the gene encoding the 5-HT2A receptor comprising at least one mutation identified by the present method to give rise to constitutive activity of the receptor.

A suitable in vivo experimental system for validation of both the physiological role of constitutively active 5-HT2A receptors, and the effects of selective 5-HT2A inverse agonists as therapeutic agents, is a transgenic animal model in which constitutive signaling through the 5-HT2A receptor has been achieved. Transgenic animals, preferably mice, may for instance be generated by two distinct approaches: 1) brain-specific over-expression of wild-type human 5-HT2A receptors; and 2) regulated expression of a constitutively active 5-HT2A receptor mutant. Both approaches rely upon standard molecular biological techniques known to those skilled in the art.

Briefly, the first approach involves subcloning of the wild type human 5-HT2A receptor gene into an appropriate transgenic vector, the expression of which is driven by a strong promoter (e.g., the CMV promoter). Brain-specific expression may be achieved by incorporating vector constructs comprising the human 5-HT2A receptor gene into the 5-HT2A genomic promoter region of the host animal by site-specific homologous recombination (K. Rajewsky et. al., J. Clin. Invest. 98(3), 1996, pp. 600-603). This is feasible, as both the human and mouse promoter regions for the 5-HT2A receptor gene have been cloned and characterized (Zhu, Q., Chen, K., and Shih, J. C., J. Neuroscience 15(7), 1995, pp. 4885-4895.). A transgenic animal may then be generated by injection of the vector construct into embryonic stem cells of the selected host animal (typically, a mouse) in accordance with standard procedures (M. R. Capecchi, Trends Genet. 5, 1989, pp. 70-76). This approach will result in regionally specific over-expression of the wild-type human 5-HT2A receptor in mouse brain.

The alternative approach requires the generation of a mutant human receptor which has a significantly higher basal activity than the wild-type gene. By applying standard PCR-based site-directed mutagenesis (e.g., as disclosed in E. S. Burstein et al., Biochem. Pharmacol. 51, 1996, pp. 539-544; and T. A. Spalding et al., J. Pharm. Exp. Ther. 275, 1995, pp. 1274-1279, for the muscarinic m5 receptor), it is possible to generate a receptor mutant that will exhibit increased constitutive activity. Using homologous recombination to incorporate a transgenic expression vector in which the mutant human gene is expressed from the native mouse promoter, without overexpression, would result in an animal with regional specific brain expression of an activated human 5-HT2A receptor mutant.

The present disclosure provides a series of human 5-HT2A receptor mutants that have increased constitutive activity compared to that observed in the wild type receptor, any of which are suitable for incorporation into a transgenic mouse model. Inverse agonists of the 5-HT2A receptor identified by the present methods may suitably be tested for activity in vivo in the transgenic mouse models described above, in which the effect of the compounds on locomotor activity, startle habituation and prepulse inhibition may conveniently be studied (T. A. Sipes and M. A. Geyer, Neuropharmacology, 33(3/4), pp. 441-448). Other animal models which may be used for this purpose include 5-HT agonist induced head twitches in mice or rats, substantially as disclosed by J. H. Kehne et al., supra, which may be reduced by administration of inverse agonists of the 5-HT2A receptor.

The present invention provides a method of ameliorating symptoms of schizophrenia or psychosis in a subject in need thereof, the method comprising administering to the subject a therapeutically effective amount of an inverse agonist of the 5-HT2A receptor.

Inverse agonists of the 5-HT2A receptor identified by the methods of the present invention may be formulated in pharmaceutical compositions comprising one or more inverse agonist compounds together with a pharmaceutically acceptable diluant or excipient. Such compositions may be formulated in an appropriate manner and in accordance with accepted practices such as those disclosed in Remington's Pharmaceutical Sciences, Gennaro, Ed., Mack Publishing Co., Easton Pa., 1990.

Particularly desirable inverse agonists of the 5-HT2A receptor will exhibit considerable selectivity for that receptor. Selectivity may, in the present context, be defined as an at least 10-fold higher affinity for the 5-HT2A receptor subtype than towards at least one, and preferably more than one, other neurotransmitter receptor tested. Examples of neurotransmitter receptors against which potentially selective inverse 5-HT2A agonists may suitably be tested include histamine, dopamine, muscarinic and adrenergic receptors, as well as the other existing serotonin receptor subtypes. 5-HT2A receptor inverse agonists may be effective in the treatment of a number of neuropsychiatric diseases and disorders such as psychosis or schizophrenia without the attendant undesirable extrapyramidal side effects previously observed with non-selective compounds, notably most classical antipsychotic drugs. It is currently believed that favorable therapeutic properties will be found in selective inverse 5-HT2A agonists that have little or substantially no anti-dopaminergic activity, in particular as antagonists of the dopamine D2 receptor, as such activity is assumed to give rise to many of these extrapyramidal side effects. To identify compounds that have the desired selectivity for 5-HT2A, the present assay method should also include cells expressing at least one other neurotransmitter receptor and preferably includes cells expressing a number of different neurotransmitter receptors.

Advantageously, inverse agonist compounds may be administered in a single daily dose, or the total daily dosage may be administered in divided doses two, three or four times daily. Furthermore, compounds of the present invention may be administered in intranasal form via topical use of suitable intranasal vehicles, or via transdermal routes using those forms of transdermal skin patches well known to persons skilled in the art.

The dosage regimen for 5-HT2A inverse agonist compounds will be selected in accordance with a variety of factors. These include type, species, age, weight, sex and medical condition of the patient; the severity of the condition to be treated; the route of administration; the renal and hepatic function of the patient; and the particular compound employed. A physician of ordinary skill can readily determine and prescribe the effective amount of the drug required to prevent, counter or arrest the progress of the disease or disorder which is being treated.

The daily dosage may be varied over a wide range from about 0.01 to about 100 mg per adult human per day. An effective amount is ordinarily supplied at a dosage level of about 0.0001 mg/kg to about 25 mg/kg body weight per day. Preferably, the range is from about 0.001 to about 10 mg/kg of body weight per day, and especially from about 0.001 mg/kg to about 1 mg/kg of body weight per day. The compounds may be administered on a regimen of 1 to 4 times per day.

Inverse agonist compounds may be used alone at appropriate dosages defined by routine testing in order to obtain optimal pharmacological effect on the serotonin 5-HT2A receptor, while minimizing any potential toxic or otherwise unwanted effects. In addition, it is believed that 5-HT2A selective inverse agonists may be used as adjunctive therapy with known antipsychotic drugs to reduce the dosage required of these traditional drugs, and thereby reduce their extrapyramidal side effects.

The present invention is further illustrated in the following examples which are not to be regarded as limiting in any way to the scope of the invention as claimed.

EXAMPLES

A General Protocol for the Single Receptor Format

Cultures of NIH 3T3 cells (available from the American Type Culture Collection, as ATCC CRL 1658) were prepared to 50-60% confluence. On day one cells were trypsinized, spun down and plated at $1 \times 10^6$ cells/10 cm plate in 10 ml Dulbecco's Modified Eagle's Medium (DMEM), 10% calf serum (yield 3-4 10 cm plates from one 175 cm$^2$ flask). On day 2, cells were transfected using the calcium phosphate precipitation procedure of Wigler et al. Cell 11: 223-232 (1977). For each plate 5 µg receptor DNA, 5 µg β-gal DNA (β-gal, pSV-β-galactosidase, Promega), 20 µg salmon sperm DNA, 62.5 µl 2.0M CaCl$_2$, were brought to 0.5 ml with H$_2$O. The DNA solution was added dropwise to 0.5 ml 2× HEPES-buffered saline (280 mM NaCl, 10 mM KCl, 1.5 mM NaHPO$_4$-2H$_2$O, 12 mM dextrose, 50 mM N-(2-hydroxyethyl)piperazine-N'-(2-ethanesulfonic acid) (HEPES), pH 7.05) while gently mixing with air bubbles. On day three plates were washed with HANK's balanced saline solution (HBSS) and 10 ml DMEM+10% calf serum was added. On day four the cells were trypsinized, spun down and resuspended in 10 ml (DMEM+10% calf serum). 100 µl of the suspension was added to each well of a 96 well plate. A 2× concentration of the test compound in 100 µl DMEM (10% calf serum) was added to each well. Cells were incubated with test substances for three to five days without changing media. A modified method of Lim and Chae, Biotechniques 7:576-579 (1989) was used to assay β-gal. On the day of β-gal assay, the media were aspirated and the wells rinsed with 100 µl phosphate-buffered saline (PBS). 200 µl of PBS with 3.5 mM o-nitrophenyl-β-D-galactopyranoside and 0.5% Nonidet P-40 (Sigma) was added to each well and incubated for 4 hrs at room temperature. β-gal responses were linear for several hrs. The absorbance of each well was determined by means of a plate reader (BioTec) set to .about.405 nm.

Example 1

β-galactosidase Activity in Cells Transfected with the trk A Receptor

Figure 3A:
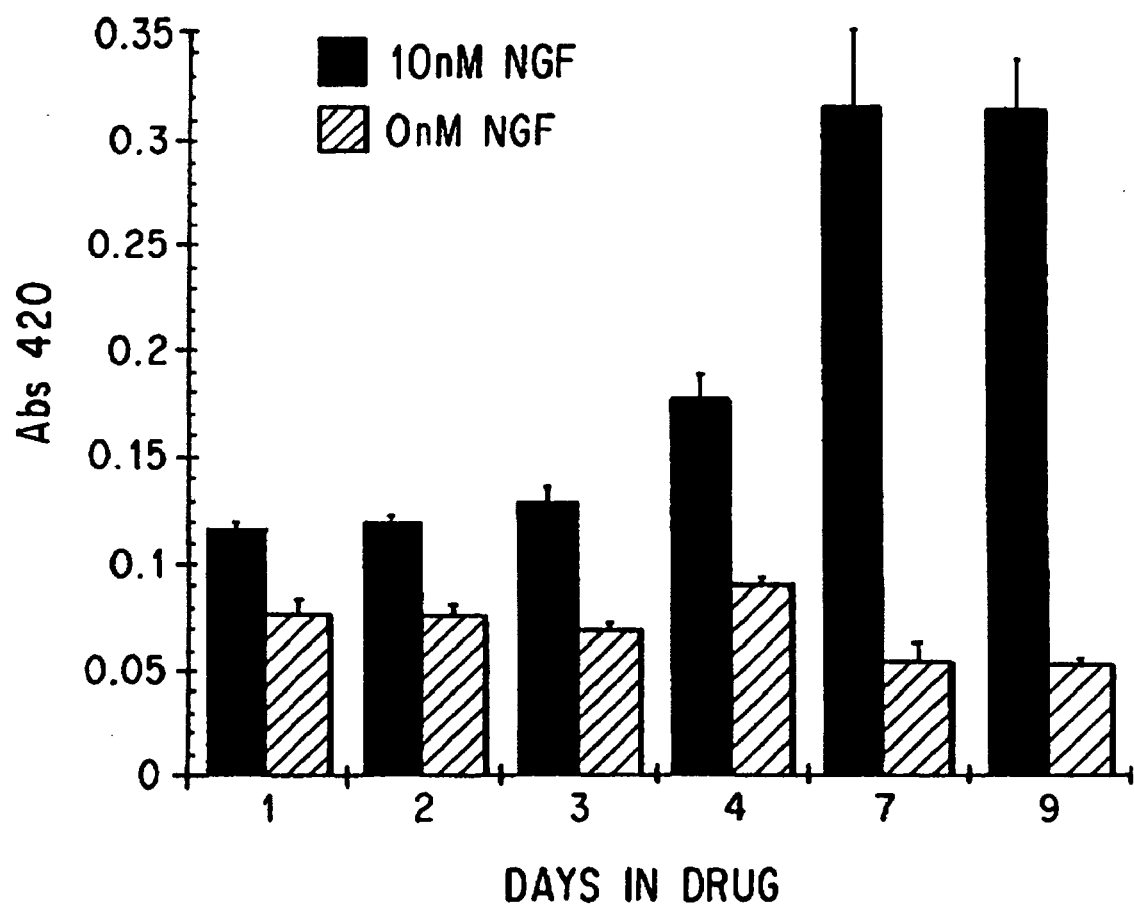
FIG. 3A illustrates the time-course of human nerve growth factor (NGF) stimulation of β-galactosidase activity in cells transfected with the human trk A receptor. Illustrated is a bar graph of the absorbance at 420 vs. days of incubation in the presence or absence of 10 nM NGF.

Nerve growth factor (NGF) is an agonist for the trk A receptor. NGF-stimulated trk A receptors activate tyrosine phosphorylation, and induce foci in NIH 3T3 cells. FIG. 3*a* illustrates data from an experiment where trk A receptor-transfected cells were grown in the presence or absence of NGF following the general procedure described above. A 10 cm plate of NIH 3T3 cells were transfected with 5 µg of trk A receptor DNA (cloned substantially as described by Kaplan et al., Science 252, 1991, p. 554, and Martin-Zanca et al., Mol.

Figure 3B:
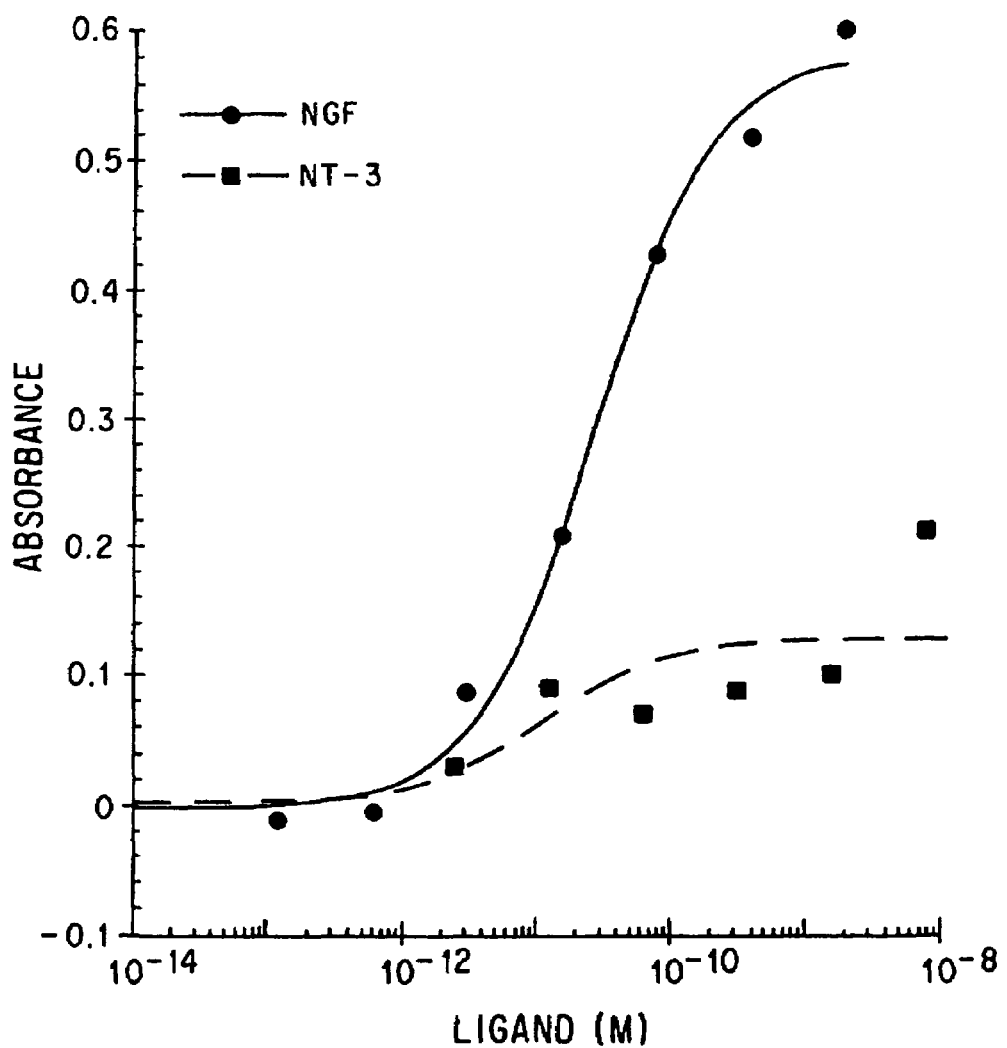
FIG. 3B illustrates the dose-response relationship of NGF and NT3 after three days of treatment.

Cell. Biol. 4, 1989, p. 24) and 5 μg of β-gal DNA. The cells were washed after 24 hrs, and after 48 hrs the cells were transferred to 96 wells of a microtiter plate and grown in the presence or absence of NGF for the indicated number of days. β-gal activity was induced by NGF, with a marked induction observed within three days. The data shown in FIG. 3A and FIG. 3B were means of triplicate determinations (each from separate wells) ±SD. FIG. 3b illustrates the NGF dose-response relationship for inducing β-gal after three days of NGF treatment. The NGF $ED_{50}$ of this response was similar to that observed of endogenous NGF receptor induced neurite outgrowth in PC 12 cells (Cordon-Cardo et al., Cell 66:173-183 (1991); Chao et al., Neuron 9:583-593 (1992)).

Also illustrated is the dose-response relationships of the related neutrotrophic factor NT3. Not shown is the fact that NGF was not able to induce amplification responses in cells transfected with the trk C receptor subtype, consistent with the known selectivity of neutrotrophin receptors (see also table 2).

Example 2

β-galactosidase Activity in Cells Transfected with Muscarinic Receptor Subtypes m1, m2, m3, m4 and m5

Muscarinic acetylcholine receptors that stimulate phospholipase c (m1, m3, m5) are able to stimulate cellular growth and induce foci in NIH 3T3 cells, only when the transfected receptors are activated by ligands that have agonist activity. In monoclonal lines isolated from NIH 3T3 cells transfected with these receptors, the agonist dose-response relationships for stimulation of phospholipase c, stimulation of mitogenesis and foci are identical, and these responses are blocked by the muscarinic receptor antagonist atropine. The m2 and m4 muscarinic receptors do not strongly stimulate phospholipase c in NIH 3T3 cells, nor do they induce foci. These data indicate that ligand-induced changes in cellular growth can be used as an assay of the pharmacology of some muscarinic receptor subtypes (Gutkind et al., PNAS 88, 4703 (1991); Stephens et al., Oncogene 8, 19-26 (1993)).

Figure 1B:
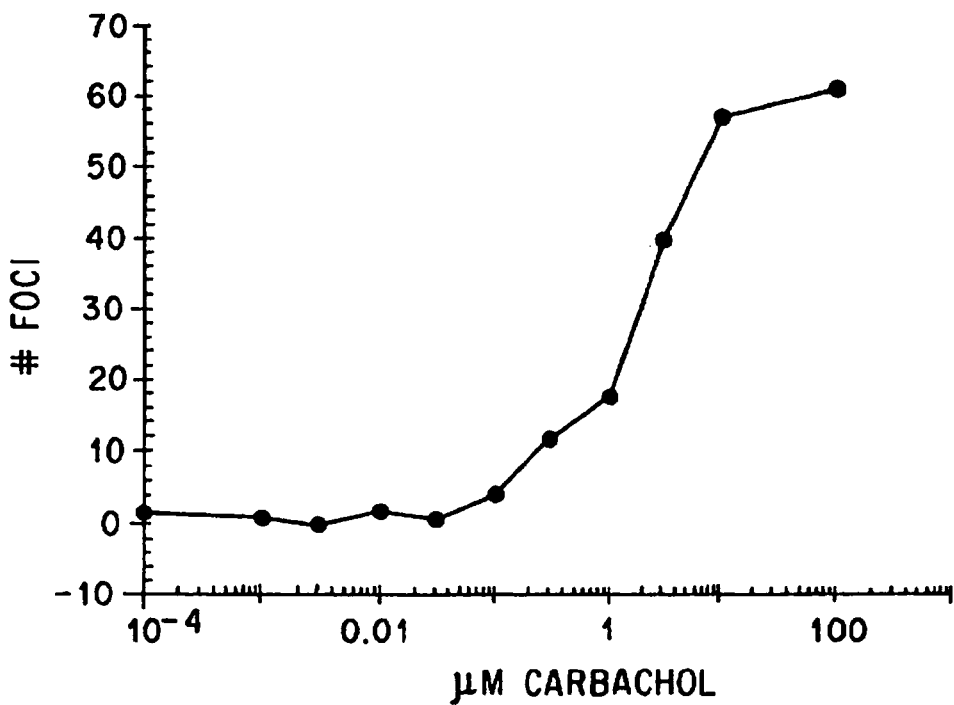
FIG. 1B is a plot of the number of foci vs. concentration of carbachol. Cells were stained and foci counted 2 weeks after carbachol treatment. Experiments were performed in 10 cm plates, and carbachol (100 μM) was applied 2 days after transfection, and was changed every 3-4 days.

The dose-response relationship of m5 DNA for inducing foci in NIH 3T3 cells is illustrated in FIG. 1a. These data indicate that the focus response requires low concentrations of DNA (.about. 1 ng) and is linear over a wide range of DNA concentrations (1 ng to at least 1000 ng). For 100 ng of m5 DNA, the dose-response relationship of carbachol for inducing foci is illustrated in FIG. 1b. Using the calcium phosphate precipitation conditions described above under the general protocol, a minority of cells in each culture are actually transfected with DNA. These data indicate that under conditions where low concentrations of DNA have been used to transfect a minority of cells within a culture, robust ligand-dependent responses are observed.

Muscarinic receptor subtypes, like many other receptors, are able to selectively interact with functionally distinct G-proteins. For example, m1, m3 and m5 receptors selectively stimulate pholipidase c by coupling with the G-protein Gq, and m2 and m4 selectively inhibit adenylyl cyclase by coupling with the G-protein Gi. m2 and m4 also selectively couple with the G-protein Go (Jones et al., in Molecular Biology of G-protein-coupled receptors, M Brann ed. Birhauser Boston. pp 170-197 (1992)). One strategy for altering the functional phenotype of a receptor is to express the receptor with a mutant G-protein. For example, if the receptor-coupling selectivity of Gq were changed to that of Gi, then m2 and m4 receptors would be able to activate such a mutant Gq. It has recently been shown that the carboxy-terminus of G-proteins directs their selectivity for different receptors. In our studies, we tested a chimera between Gq and the carboxy-terminal five amino acids of Gi (Gq-i5) or Go (Gq-i5 and Gq-o5 constructs are described in Conklin et al., Nature 363, 1993, p. 274).

Figure 4:
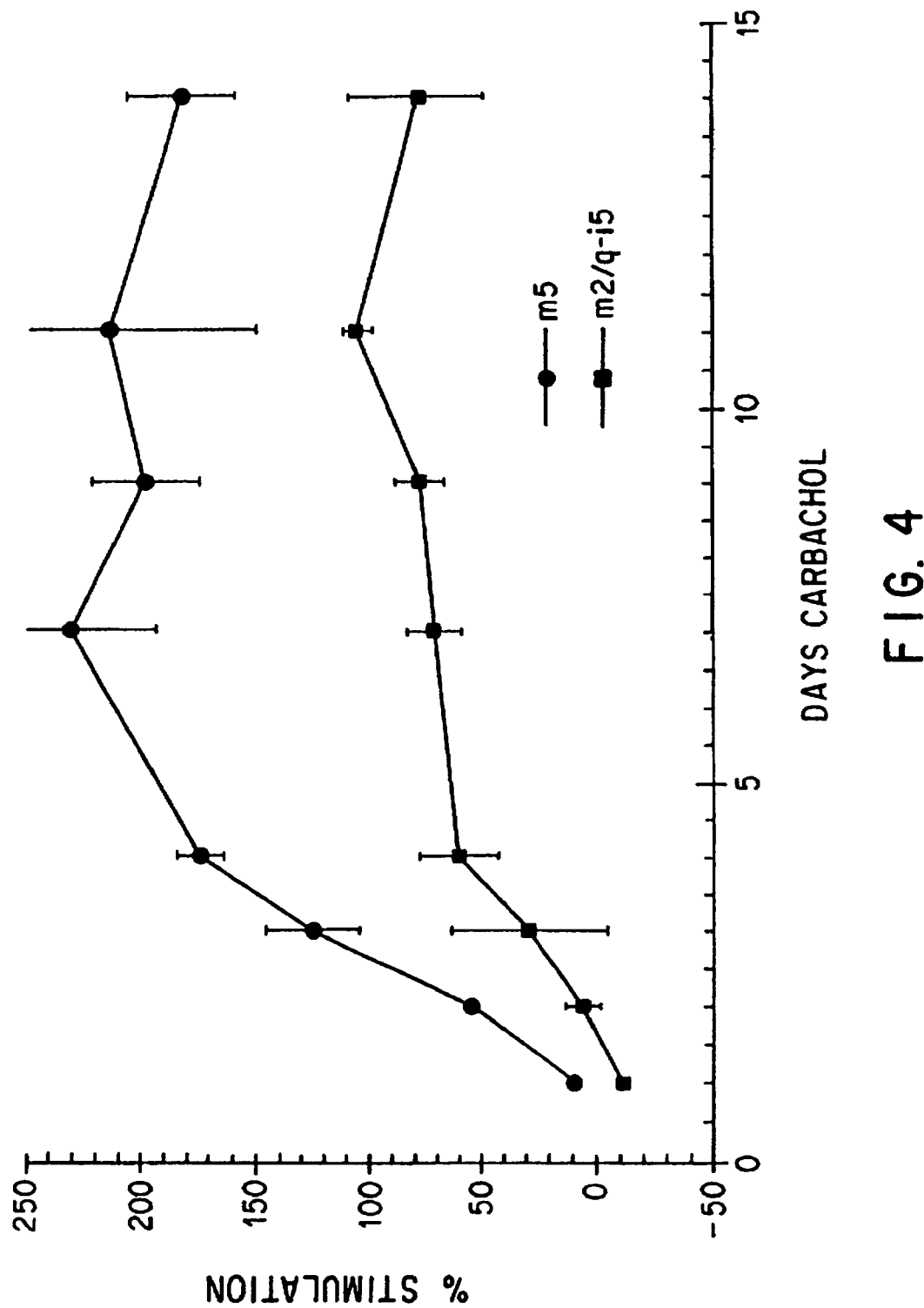
FIG. 4 illustrates the time-course of carbachol stimulation of β-galactosidase in cells tranfected with m5 and m2 muscarinic receptors.

The time-course of carbachol induction of β-galactosidase activity was investigated in NIH 3T3 cells (FIG. 4) transfected with m5 and m2 muscarinic receptors. Either 5 μg of human m5 muscarinic receptor DNA and 5 μg of a control plasmid DNA, or 5 μg of human m2 muscarinic receptor DNA and 5 μg of Gq-i5 DNA (m2/Gq-i5), were combined with 5 μg of β-galactosidase DNA to transfect 10 cm plates. After 48 hrs, the cells were transferred to wells of a 96 well plate for immediate treatment with carbachol. Carbachol treatment was continued for the indicated number of days, and media and carbachol were changed every three days.

In the case of the m2 receptor, the G-i5 chimera was co-expressed with with the receptor (5 μg of receptor and 5 μg of G-protein). In the absence of expressed G-protein, m2 receptors have no effect on α-galactosidase levels. For both the m2/q-i5 and m5 transfected cultures, carbachol was able to significantly induce β-galactosidase levels, and this effect reached a plateau at about five days of drug treatment. The abilities of Gq-i5 and Gq-o5 to mediate β-galactosidase responses were compared to stimulation of m4 receptors by carbachol. The ED50's of carbachol for m4/q-i5 was 0.037±0.046 and for m4/q-o5 was 0.032±0.047, and both combinations yielded similar maximal responses. These data indicate that m4 receptors couple with similar efficiencies to q-i5 and q-o5.

Based on the above time-courses and experiments where cell densities were optimized to yield maximal β-galactosidase signals, the general protocol for the Single Receptor Format described above was applied. The m1-m5 muscarinic receptors were cloned substantially as described by Bonner et al., Science 237, 1987, p. 527, and Bonner et al., Neuron 1, 1988, p. 403. For each of the m1, m3 and m5 muscarinic receptors, NIH 3T3 cells were transfected with 5 μg of receptor DNA and 5 μg of β-galactosidase DNA. For each of the m2 and m4 muscarinic receptors, NIH 3T3 cells were transfected with 5 μg of receptor DNA, 5 μg of Gq-i5 DNA, and 5 μg of β-galactosidase DNA. Data for the m1, m3 and m5 muscarinic receptors were collected 5 days after carbachol treatment, and data for the m2 and m4 muscarinic receptors were collected 4 days after carbachol treatment. No media changes were performed. Data were means from three-four independent wells, read directly from the original wells 4 hrs after addition of substrate and detergent. Lines are computer generated fits of the data to an equation for a single mass-action site of action.

Figure 6A:
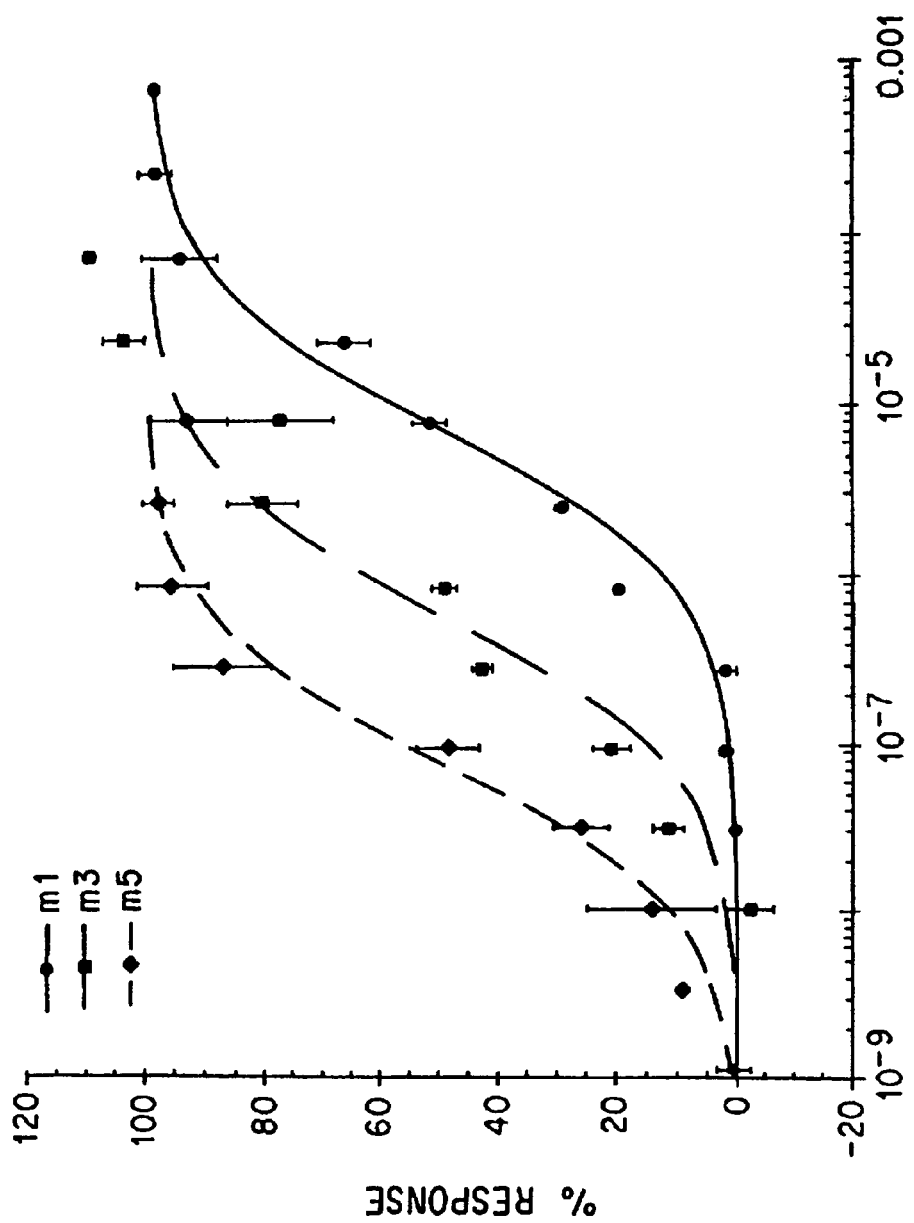
FIG. 6A illustrates the dose-response relationships of m1, m3 and m5 muscarinic receptors.
Figure 6B:
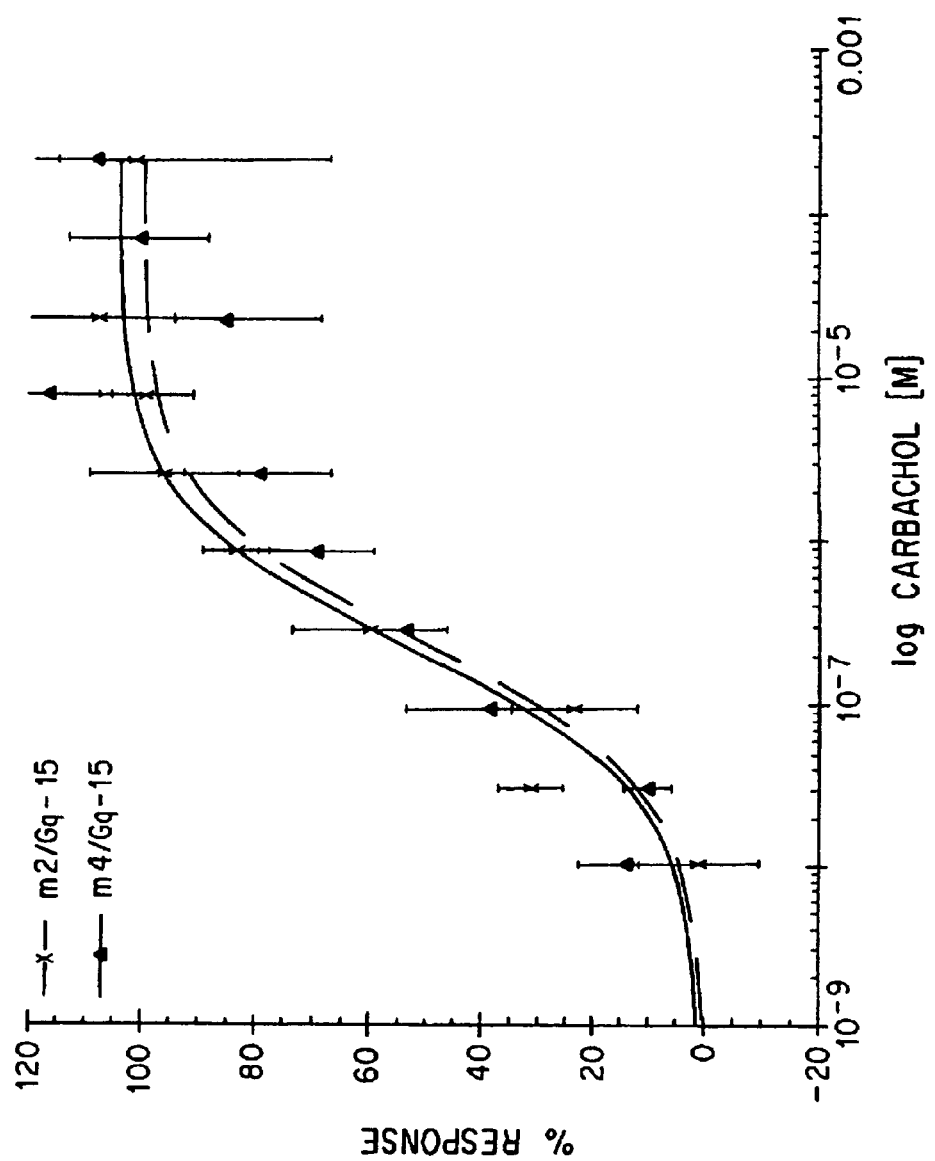
FIG. 6B illustrates the dose-response relationships of m2 and m4 muscarinic receptors.

The carbachol dose-response relationships of m1, m3 and m5 transfected cells was investigated (FIG. 6A). Similar experiments were performed with m2 and m4 receptors co-transfected with Gq-i5 (FIG. 6B). As illustrated, the general protocol permitted precise determinations of the $ED_{50}$'s of carbachol for these five receptors. These values are in good agreement with ealier measurements using foci induction (Gutkind et al., Proc. Natl. Acad. Sci. USA 88, 4703 (1991)), mitogenesis (Stephens et al. Oncogene 8:19-26 (1993)), second messenger and physiological responses (Jones et al. Mol. Pharm. 40:242-247 1991)). Also illustrated is a fit of the data to an equation for a single mass-action site of action. As indicated, all of the receptors obeyed this receptor mass-action relationship. Table 1 illustrates the pharmacologies of several muscarinic agonists and antagonists for the m1-m5 receptors evaluated using this assay. All of the antagonist data was in good agreement with parameters that have been previously evaluated using binding assays, with the exception that most antagonist have lower potency in these functional assays than in binding assays (reviewed in Jones et al. in Molecular Biology of G-Protein Coupled Receptors, op. cit.). Also, illustrated is the ability of the assay to discriminate between the responses of full and partial agonists. Partial agonist are often difficult to differentiate from full agonists in functional assays. Difficulties are often due to ceiling effects and receptor spareness. In fact, assays rarely combine a high sensitivity to weak partial agonists with an ability to discriminate full and partial agonists.

Example 4

Stimulation of Different Receptors

Receptors belonging to several functional categories have successfully been assayed using the general protocol for the Single Receptor Format described above. The results are shown in Table 2 below. These data indicate that a wide range of receptors and related molecules can be assayed by our amplification assays. Illustrated are examples of receptors for a diversity of transmitters including monoamines, amino acids, peptides and large hormones (muscarinic receptors,

TABLE 1

Pharmacology of muscarinic acetylcholine receptors

| agonist | m1 | m2 | m3 | m4 | m5 |
|---|---|---|---|---|---|
| A. Pharmacology of Muscarinic Agonists - $EC_{50}$ [μM] (% Max) | | | | | |
| arecoline | 3.2 ± 0.7 | 0.025 ± 0.001 | 0.34 ± 0.11 | 0.13 ± 0.05 | 0.60 ± 0.05 |
|  | (86 ± 3) | (105 ± 0) | (66 ± 9) | (72 ± 3) | (77 ± 2) |
| carbachol | 6.5 ± 0.6 | 0.10 ± 0.04 | 1.4 ± 0.7 | 0.27 ± 0.07 | 0.11 ± 0.05 |
|  | (100) | (100) | (100) | (100) | (100) |
| McN A-434 | 1.1 ± 0.2 | 1.5 ± 0.6 | 2.2 ± 0.0 | 0.12 ± 0.02 | 1.0 ± 0.3 |
|  | (43 ± 2) | (108 ± 7) | (38 ± 2) | (84 ± 3) | (57 ± 4) |
| muscarine | 2.4 ± 0.8 | 0.06 ± 0.02 | 0.56 ± 0.25 | 0.32 ± 0.15 | 0.39 ± 0.18 |
|  | (84 ± 4) | (76 ± 1) | (84 ± 6) | (69 ± 2) | (86 ± 0) |
| oxotremorine | 0.39 ± 0.13 | 0.019 ± 0.010 | 0.21 ± 0.06 | 0.033 ± 0.014 | 0.055 ± 0.001 |
|  | (75 ± 10) | (100 ± 5) | (66 ± 5) | (102 ± 3) | (74 ± 2) |
| pilocarpine | 274 ± 30 | 25 ± 1 | 35 ± 3 | 60 ± 16 | 27 ± 10 |
|  | (79 ± 5) | (107 ± 4) | (54 ± 7) | (71 ± 8) | (71 ± 4) |
| B. Pharmacology of Muscarinic Antagonists -negative log $K_i$ [M] | | | | | |
| atropine | 9.0 ± 0.1 | 8.3 ± 0.3 | 8.9 ± 0.2 | 9.1 ± 0.0 | 9.1 ± 0.0 |
| pirenzepine | 7.7 ± 0.0 | 6.2 ± 0.0 | 6.6 ± 0.2 | 7.3 ± 0.2 | 6.9 ± 0.0 |
| 4-DAMP | 8.6 ± 0.0 | 7.6 ± 0.2 | 8.7 ± 0.3 | 9.1 ± 0.1 | 9.0 ± 0.2 |
| p-F-HHSiD | 6.6 ± 0.2 | 6.3 ± 0.1 | 7.5 ± 0.1 | 7.3 ± 0.1 | 7.1 ± 0.2 |
| methocrtramine | 6.3 ± 0.1 | 7.6 ± 0.1 | <6.0 | 6.4 ± 0.1 | <6.0 |

Dose-response relationships of muscarinic agonists and antagonists at the five cloned human muscarinic receptor subtypes. NIH 3T3 cells were cotransfected with a muscarinic receptor and galactosidase cDNAs. The m2 and m4 were also cotransfected with Gqi5 cDNA. Amplification assays were performed using the Single Receptor Format. Data represent the mean (±SE) of 2-4 experiments.
A. Agonist Pharmacology. Individual $EC_{50}$ and maximal responses were derived by nonlinear regression of data from 8-10 concentrations of the indicated ligands, with 3-4 replicates per concentration. Maximum responses are indicated as a % of carbachol responses. Maximum responses for carbachol were defined using 200 μM (m1), 10 μM (m2, m4), 100 μM (m3) and 5 μM (m5).
B. Antagonist Pharmacology. Individual $IC_{50}$ values were derived by nonlinear regression of data from 8-10 concentration of the indicated ligands, with 3-4 replicates per concentration. $IC_{50}$ values were converted to $K_i$ values using the ChengPrusoff equation.
Antagonists were evaluated using carbachol at 50 μM (m1), 5 μM (m2, m4), 10 μM (m3) and 1 μM (m5).

Example 3

Luciferase Activity in Cells Transfected with the m5 and m2 (Gq-i5) Muscarinic Receptors Following the general protocol described above, amplification of the m5 muscarinic receptor and the m2 muscarinic receptor (co-transfection with Gq-i5) was determined using firefly luciferase (luc, pGL2-control vector, Promega) as a marker instead of β-galactosidase. Receptor, marker, and G-protein DNA concentrations were identical to those described for the β-galactosidase experiments in Example 2. The ED50's of carbachol were 0.22±0.1 μM for m5 and 0.14±0.11 μM for m2/q-i5 for inducing activity of firefly lucifierase. Firefly luciferase was assayed as recommended by the manufacturer (Promega). The data obtained indicate that, like β-galactosidase, firefly luciferase can serve as a sensitive marker of muscarinic receptor activation by a ligand.

Bonner et al., Science 237: 527, 1987; Bonner et al., Neuron 1: 403, 1988; dopamine D2 receptor, Stormann et al., mol. pharm. 37: 1, 1990; tachykinin receptor, Takeda et al., BBRC 179: 1232, 1991; Huang et al., BBRC 184: 966, 1992; Gerard et al., JBC 265: 20455, 1990; α1 adrenergic receptors, Cottecchia et al., PNAS 85: 7159, 1988; Lomasney et al., JBC 266: 6365, 1991; α2 adrenergic receptors, Regan et al., PNAS 85: 6301, 1988; Lomashey et al., PNAS 87: 5094, 1990; endothelin receptors, Arai et al., Nature 348: 730, 1990; Sakurai et al., Nature 348: 732, 1990; P53, Baker et al., Science 249: 912, 1990; G-protein mutants, Voyno-Yasenetskaya et al., JBC 269: 4721. A diversity of signal transduction classes are also illustrated: G-protein coupled receptors, tyrosine kinase linked receptors, G-proteins and oncogenes. In a few of these cases, focus assays have been used to assay ligand interaction with the illustrated receptors. In many cases, it has been shown that focus assays do not yield measurable responses (e.g., m2 and m4 muscarinic receptors with Gq-i5). A detailed analysis of pharmacology of a adrenergic receptors is also presented in Table 3.

TABLE 2

Receptors Assayed by Amplification

| Receptor | Ligand EC$_{50}$ nM | | | R$_{max}$ | Trans. Class |
|---|---|---|---|---|---|
| Adrenergic | Phenylephrine | UK 14,304 | Epinephrine | | |
| alpha 1A | 460 ± 30 | | | +++ | Gq |
| alpha 1B | 110 ± 20 | | | +++ | Gq |
| alpha 2 C10 | | 200 | 430 | +++ | Gq/Gi |
| alpha 2 C2 | | 690 | 1,700 | +++ | Gq/Gi |
| alpha 2 C4 | | 780 | 50 | ++ | Gq/Gi |
| Dopamine | Quinpirole | | | | |
| D2 | 0.5 ± 0.4 | | | ++ | Gi* |
| Endothelin | ET-1 | ET-2 | ET-3 | | |
| ET$_A$ | 0.079 ± 0.048 | 16 ± 4.1 | 2.1 ± 1.2 | +++ | Gq |
| ET$_B$ | 0.24 ± 0.2 | 17.6 ± 8.5 | 0.14 ± 0.07 | +++ | Gq |
| Glutamate | Quisqualate | | | | |
| Metabatropic | 2,400 ± 1,400 | | | + | Gq |
| Insulin | Insulin | | | | |
| | 0.08 ± 0.08 | | | + | TK |
| Muscarinic | carbachol | Oxotremorine | muscarine | | |
| m1 | 6,500 ± 600 | 390 ± 130 | 2,400 ± 800 | +++ | Gq |
| m2 | 100 ± 40 | 19 ± 10 | 60 + 20 | ++ | Gi* |
| m3 | 1,400 ± 700 | 210 ± 60 | 560 ± 250 | +++ | Gq |
| m4 | 270 ± 70 | 33 ± 14 | 320 ± 150 | ++ | Gi* |
| m5 | 110 ± 50 | 55 ± 1 | 390 + 180 | +++ | Gq |
| Neurotrophin | NGF | NT3 | | | |
| trk A | 1.2 ± 0.6 ng/ml | >1000 ng/ml | | ++++ | TK |
| trk C | | 2.4 ± 1.1 ng/ml | | ++++ | TK |
| Prostanoid | Fluprostenol | MB28767 | | | |
| FP | 2 ± 1 | | | +++ | Gq |
| EP3 | | 270 ± 190 | | ++ | Gi |
| Tachykinin | substance P | neurokinin A | neurokinin B | | |
| NK1 | 7 ± 3 | 14 ± 5 | 99 ± 50 | +++ | TK |
| NK2 | 65 ± 6.5 | 21 ± 6 | 1.3 ± 0.7 | +++ | TK |
| NK3 | 164 ± 59 | 11 ± 2 | 100 ± 20 | +++ | TK |
| Mutant/Activated | | | | | |
| v-ras | | | | ++++ | |
| p53-H175 | | | | +++ | |
| p53-W248 | | | | +++ | |
| G-12-229L | | | | +++ | |
| G-q-183C | | | | ++ | |
| m5-164 | | | | +++ | Gq |
| G-protein | | | | | |
| G-q | | | | +++ | |
| G-12 | | | | +++ | |

Receptors and other proteins that induce amplification responses in NIH 3T3 cells. All clones were tested using the single receptor format.
Ligands were tested using 7-9 doses in duplicate.
R$_{max}$ indicates the maximum response that was observed with each clone in arbitrary units relative to the other clones (++++ highest, + lowest).
The known signal transduction classes of receptors are indicated (TK = tyrosine kinase). Some receptors (*) required the coexpression of the Gprotein Gqi5 to mediate a response.
In the case of the mutantactivated clones (oncogenes in some cases), the indicated amino acid substitutions caused the protein to induce significant amplification responses in the absence of added ligand.
For the indicated wildtype Gproteins, the Gproteins could be assayed when coexpressed with a receptor (R). Gproteins are named by the nomenclature of Conklin et al. (Nature 363: 274-276; 1993). m5-164 refers to the constitutively active m5 receptor described in FIG. 13

TABLE 3

Agonist Pharmacology of Adrenergic Receptors - EC$_{50}$ nM/Max Response

| Agonist | a2-C2 | a2-C4 | a2-C10 |
|---|---|---|---|
| Epinephrine | 1,700/++ | 50/+ | 430/++ |
| Norepinephrine | 7,200/++ | 2/+ | — |
| Clonidine | ± | >10,000/++ | — |
| p-I-Clonidine | 50/+ | — | — |
| p-NH2-Clonidine | 400/+ | ± | ± |
| BHT 920 | >10,000/+++ | >10,000/+++ | >10,000/+++ |
| BHT 933 | >10,000/+++ | ND | >10,000/++ |
| Guanfacine | 2,500/++ | ± | 4,600/++ |
| Prazocin | 8,700/++ | >10,000/++ | ± |
| Oxymetazoline | 220/+++ | >10,000/+ | 4,600/++ |
| Rilmenidine | ± | 480/+ | ± |
| Dexmedetomidine | 2/+++ | ± | ± |
| Moxonidine | 1,500/++ | 2,000/+ | 4,400/+++ |

TABLE 3-continued

Agonist Pharmacology of Adrenergic
Receptors - $EC_{50}$ nM/Max Response

| Agonist | a2-C2 | a2-C4 | a2-C10 |
|---|---|---|---|
| Isoproterenol | ± | >10,000/+ | — |
| UK 14,304 | 690/++ | 780/+ | 200/+++ |

Agonist Pharmacology of cloned a2 adrenergic receptors. Doseresponse relationships of adrenergic agonists at three cloned human a2 adrenergic receptor subtypes. NIH 3T3 cells were cotransfected with adrenergic receptor and galactosidase cDNAs. Amplification assays were performed using the single receptor format. Data represent the mean of 2-experiments. Individual $EC_{50}$ and maximal responses were derived by nonlinear regression of data from 8-10 concentrations of the indicated ligands, with 3-4 replicates per concentration. Maximum responses are indicated relative to other ligands at a given receptor (++++ highest, + lowest). Overall the C2 and C10 mediated more robustresponses than C4.
(ND) not determined,
(±) a very small response was observed, but reliable values could not be calculated.

Example 5

Random Mutagenesis of the m5 Muscarinic Receptor

Figure 7:
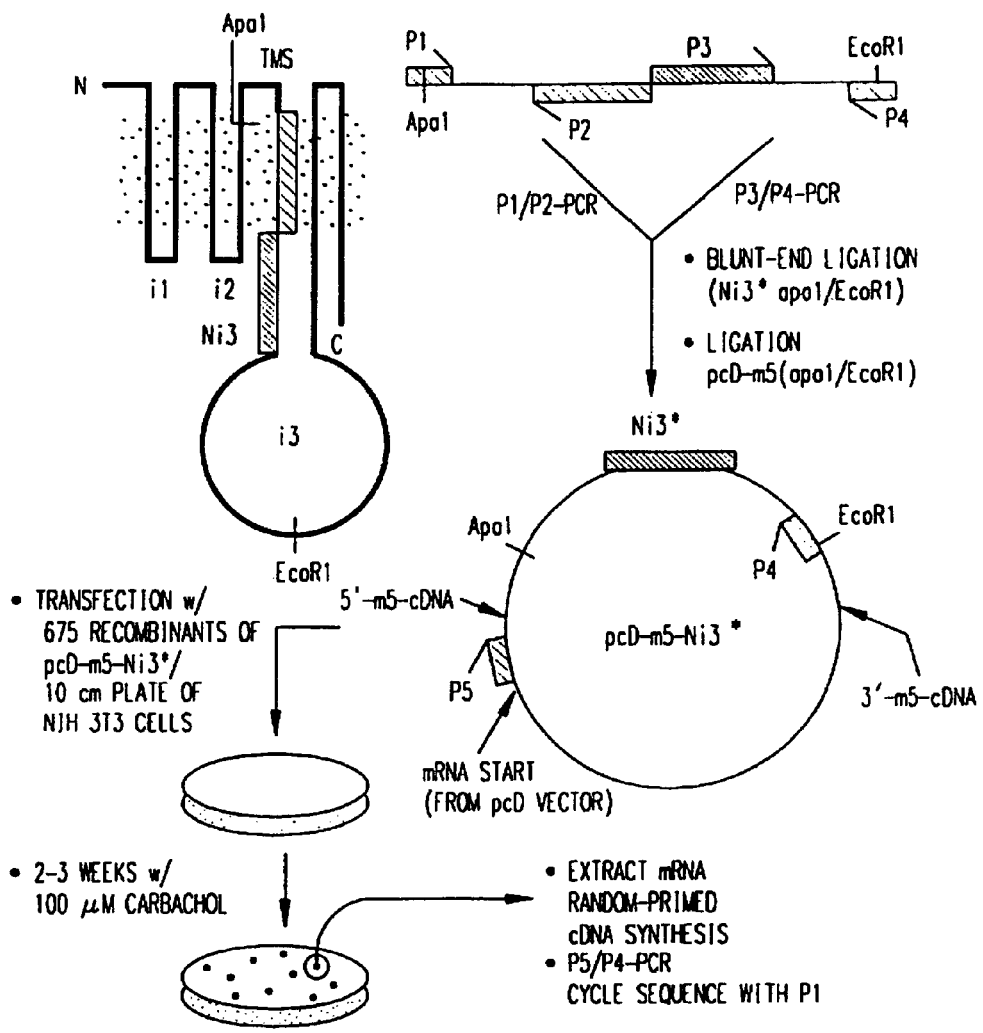
FIG. 7 is a schematic drawing showing a strategy for random-saturation mutagenesis of the m5 muscarinic acetylcholine receptor.

To illustrate the utility of the Multiple Receptor Format, the m5 receptor was subjected to random mutagenesis over the N-terminal 20 amino acids of the third intracellular loop (N-i3), adjacent to the fifth transmembrane domain (TM5), region of the receptor that is involved in coupling to G-proteins. Two PCR products were prepared such that the reverse primer (P2) for the first product comprised the entire TM5 domain and the forward primer (P3) for the second product comprised the entire N-i3 domain To incorporate mutations, an equimolar mixture of the four bases were substituted at a 15% rate for wild-type nucleotides during synthesis of the P3 primer. The outer primers (P1 and P4) contain Apa1 and EcoR1 restriction sites for subsequent cloning. The two PCR products were treated with T4 DNA polymerase to create blunt ends, ligated to yield concatamers, and restricted with Apa1 and EcoR1 to release the randomly-mutated (*) Ni3*Apa1/EcoR1 inserts. Inserts were ligated into a Apa1/EcoR1 fragment of the pcD-m5 yielding a population of mutant m5 receptor cDNA (pcD-m5-Ni3*). The overall cloning strategy is shown in FIG. 7. A cDNA library of receptors, each with a different set of random mutations, was used to transfect NIH 3T3 cells. Transfections were performed with 450 ng of library cDNA (675 recombinants) per 10 cm plate. The NIH 3T3 cells were grown in the presence of 100 μM carbachol until foci were formed. After 2-3 weeks, macroscopically visible foci are removed from the plate, total RNA was extracted, and cDNA synthesized using random-hexamers as primers. These cDNA templates were used to amplify 1.6 kb fragments using P4 and P5 as PCR primers. P5 is complementary to a plasmid DNA sequence that is transcribed but is upstream of the m5 receptor cDNA. Thus, endogenous genomic sequences could not be amplified. The PCR products were directly sequenced using Taq polymerase in a cycle-sequencing protocol using P1 as a primer.

Figure 9:
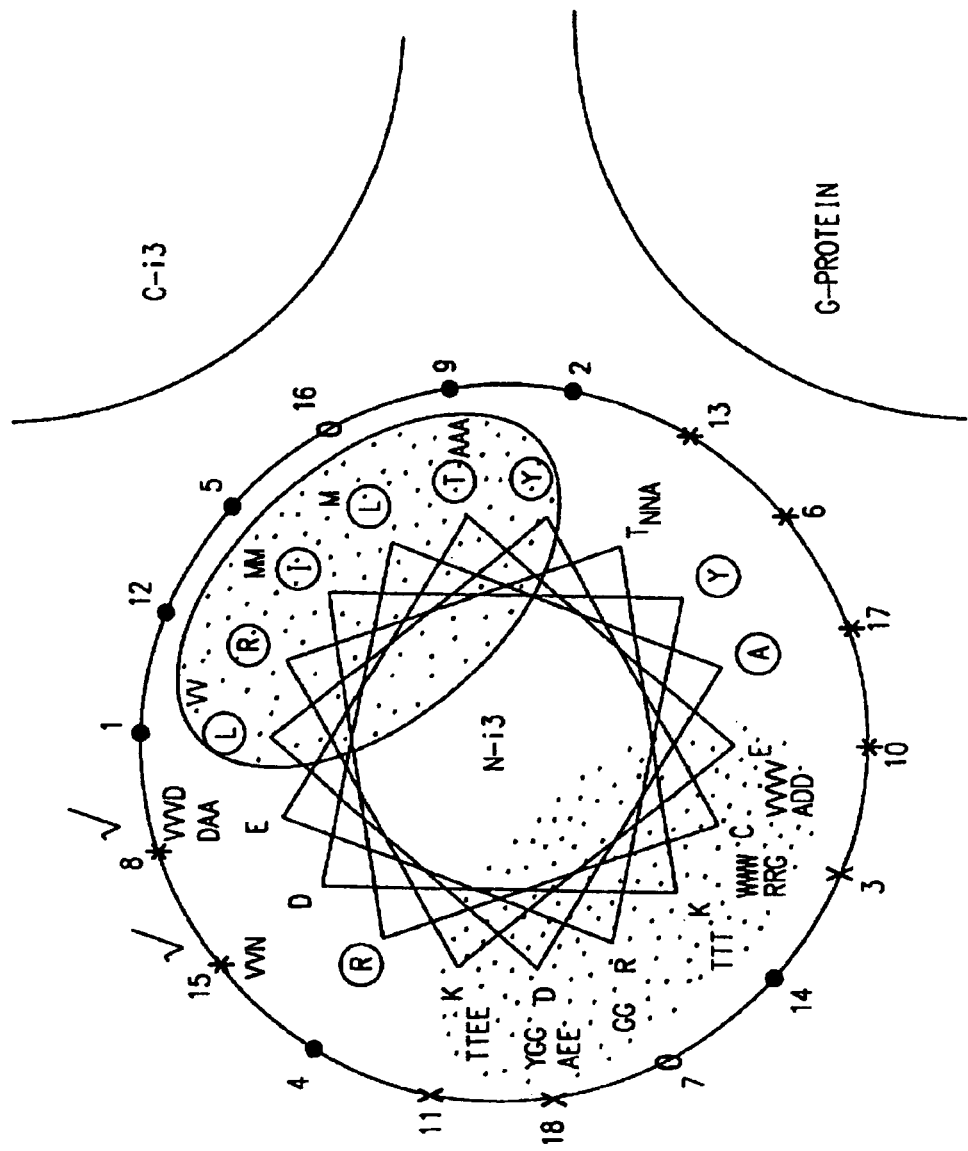
FIG. 9 is a schematic drawing showing a helical representation of the mutated domain of the m5 muscarinic receptor (SEQ ID NO:1). The domain is viewed from the intracellular space. C-i3 represents the C-terminal region of the i3 loop. Amino acid substitutions (from FIG. 8) are indicated by small letters. Positions where only conserved substitutions were isolated are circled. The large outlined and shaded oval encompasses the amino acid positions in which only conserved substitutions were observed. This is predicted to be the functionally critical face of the helix. The large shaded oval encompasses amino acids positions where nonconserved substitutions were observed at every position. This is predicted to be a functionally noncritical face of the helix. The large outer circle indicates the numbering of the amino acids starting at TM5. Classification of the amino acids with respect to homologies with the other muscarinic receptors are indicated on this circle using symbols that are defined in FIG. 8. Checks indicate positions in the m1 muscarinic receptor (SEQ ID NO:12) that tolerate radical substitutions as judged by site-directed mutagenesis.

As illustrated in FIGS. 8 and 9, many different mutant receptors were identified in foci. These data allowed predictions concerning the likely structure of the region of the muscarinic receptor that is involved in G-protein-coupling. On a technical level these data indicate that when modest concentrations of receptor DNA are used, a single plasmid DNA is able to tranfect a NIH 3T3 cell and allow the ligand carbachol to stimulate growth of the cell resulting in a foci, and that the mutant receptor that induced the foci could be identified by DNA amplification procedures.

Example 6

Figure 5:
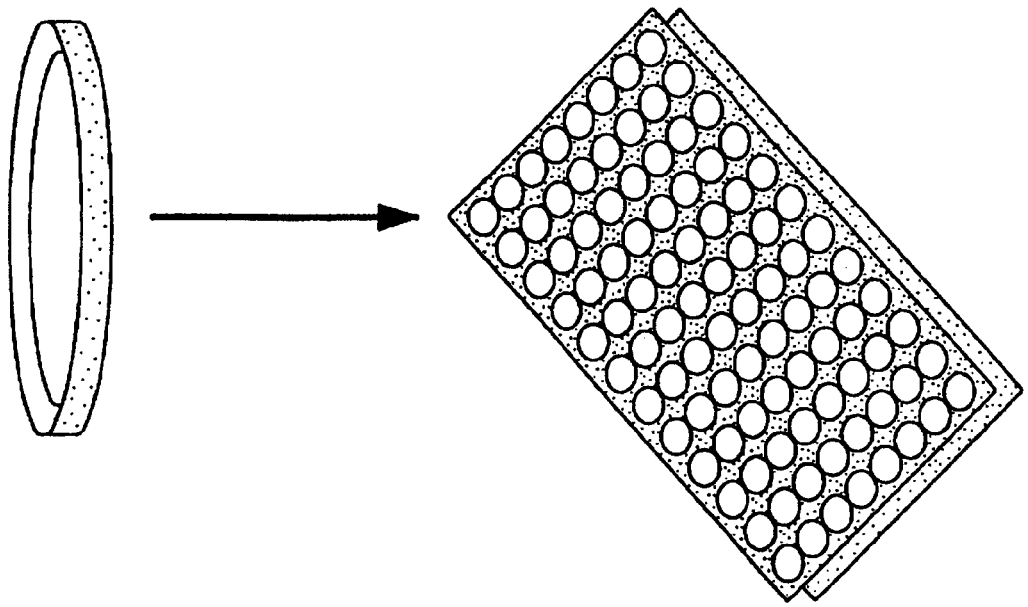
FIG. 5 is a schematic drawing showing an example protocol that can be used to assay receptors in a Single Receptor Format.
Figure 13:
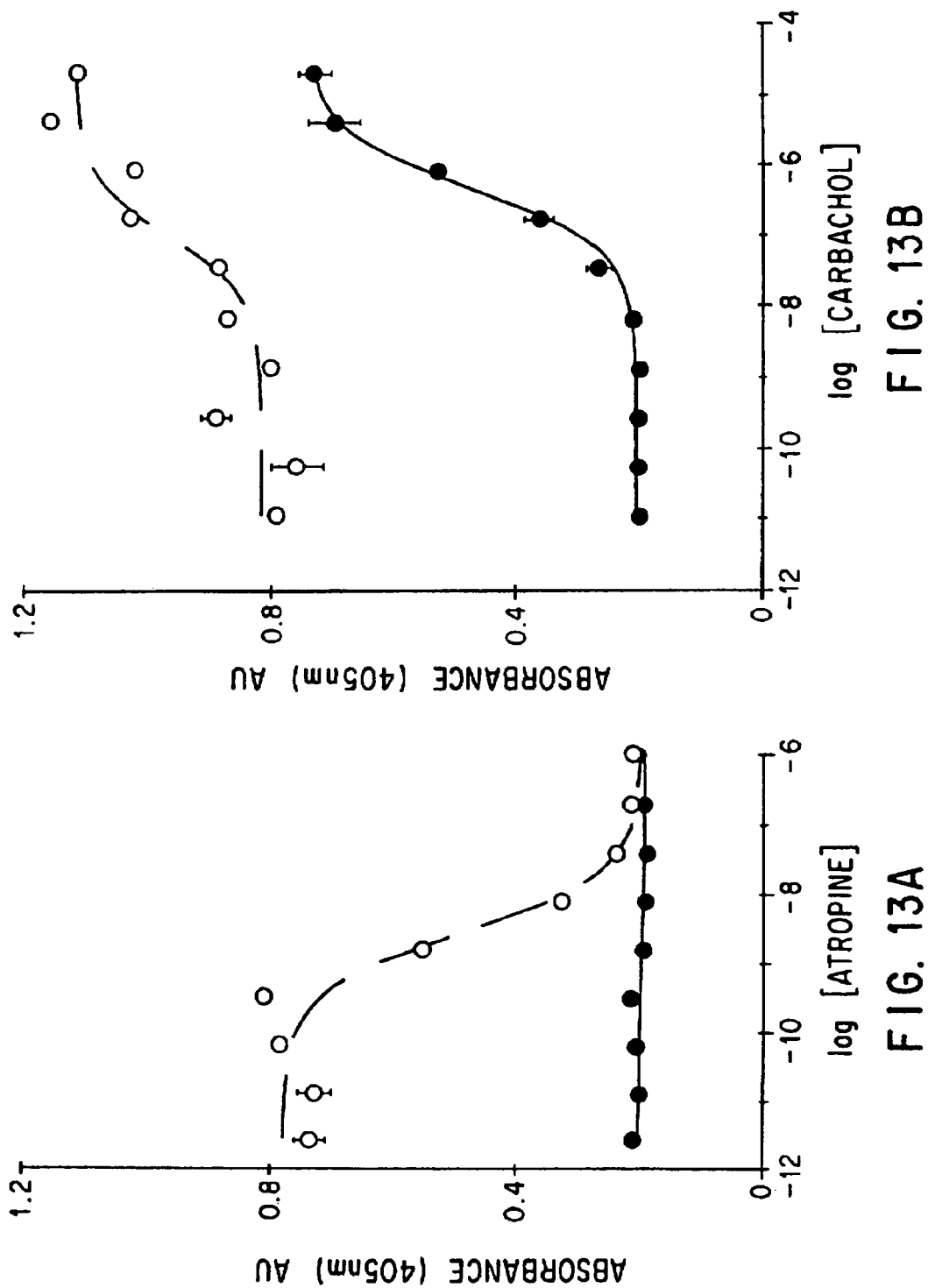
FIG. 13 illustrates the agonist and antagonist phenotypes of a mutant m5 receptor. Ten cm plates of NIH 3T3 cells were transfected with 1.5 μg of wild-type m5 (•) or m5-160 mutant receptor (°), and 3 μg of β-gal cDNA. Assays were performed as described in FIG. 5 after incubation in the indicated ligands for four days.

Random Mutagenesis of the m5 Muscarinic Receptor Assayed by Amplification of β-Galactosidase Using random mutagenesis strategies analogous to that described in FIG. 7, we have introduced mutations into regions of the m5 receptor thought to be involved in ligand binding and G-protein coupling. To assay these mutants a small scale plasmid preparation is made for each clone. This is performed using mini Qiagen anion exchange columns. These DNA preparations are used in transfections and assays in modifications of the Single Receptor Format. Modifications involve a proportional scale down in NIH 3T3 cell numbers and DNA amounts from those used for 10 cm plates, to amounts appropriate for individual wells of 6 well or 24 well plates. In the case of transfections performed in 24 well plates, β-gal assays are performed directly in the wells used for transfection without an intermediate transfer step (e.g., the 10 cm plate to 96 well plate transfer of the standard Single Receptor Format, FIG. 5). Using these procedures we have screened several hundred clones for a variety of functional phenotypes. To identify mutant receptors that retain the ability to respond to agonist, we screen with high concentrations of agonist. To identify mutants that have elevated activity in the absence of ligand, we screen mutants in the absence of agonist and/or in the presence of antagonist. One clone that was isolated by this procedure is illustrated in FIG. 13. Relative to wild-type, this clone has a significantly elevated response in the absence of ligand, and this basal response is blocked by antagonists. These data indicate the utility of amplification assays for the identification of receptors with mutant phenotypes.

Example 7

Multiplex Receptor Format

Figure 15A:
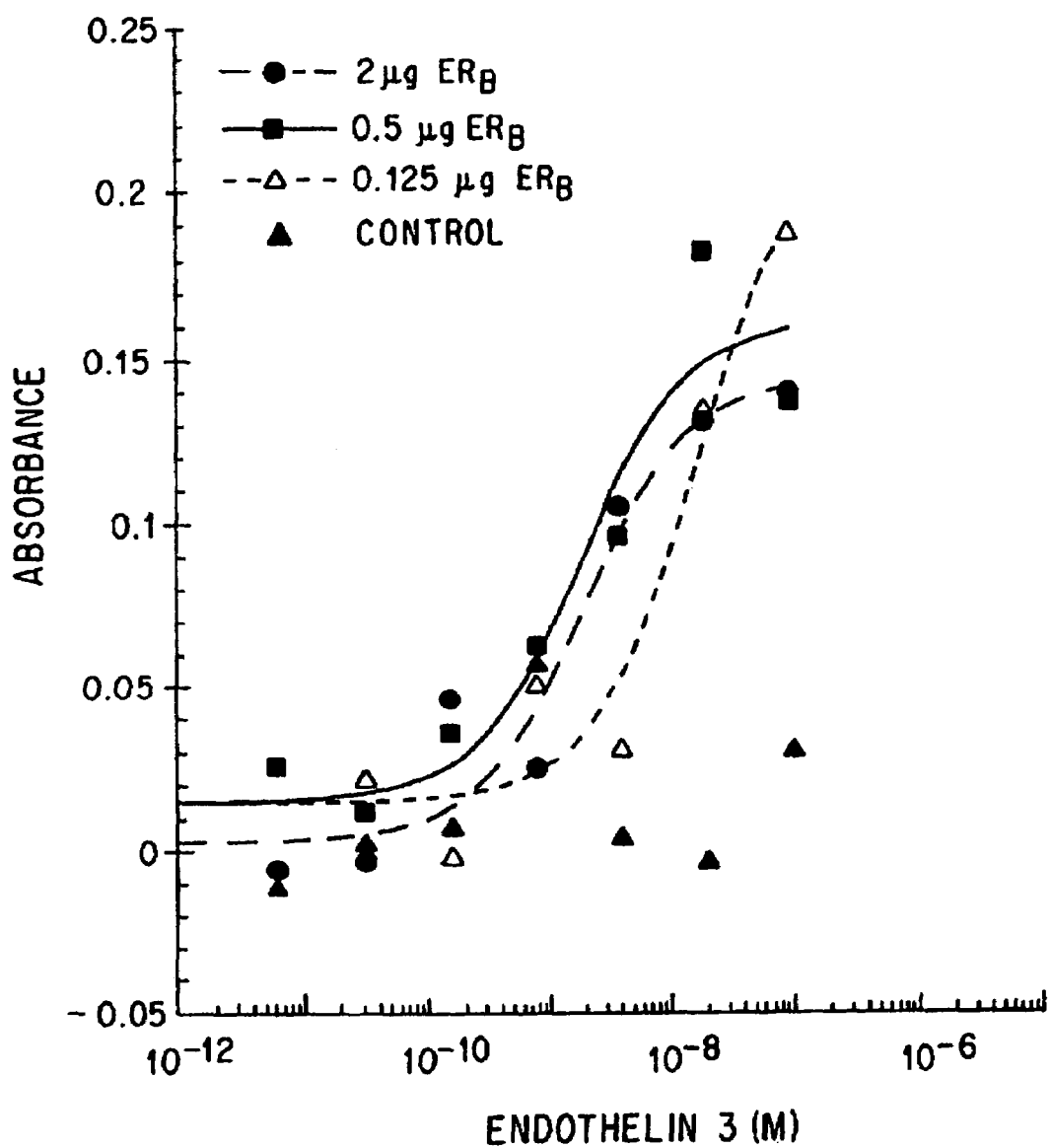
FIG. 15 illustrates the ligand and receptor cDNA dose/response relationships of the FP prostanoid and ERB endothelin receptors. Ten cm plates of NIH 3T3 cells were transfected with the indicated concentrations of receptor cDNA. Cells were incubated in wells of a 96 well plate for 4 days with the indicated concentration of ligands. All of the transfections also contained 2.5 μg of the D2 receptor and 2.5 μg of the β-gal cDNAs.
Figure 15B:
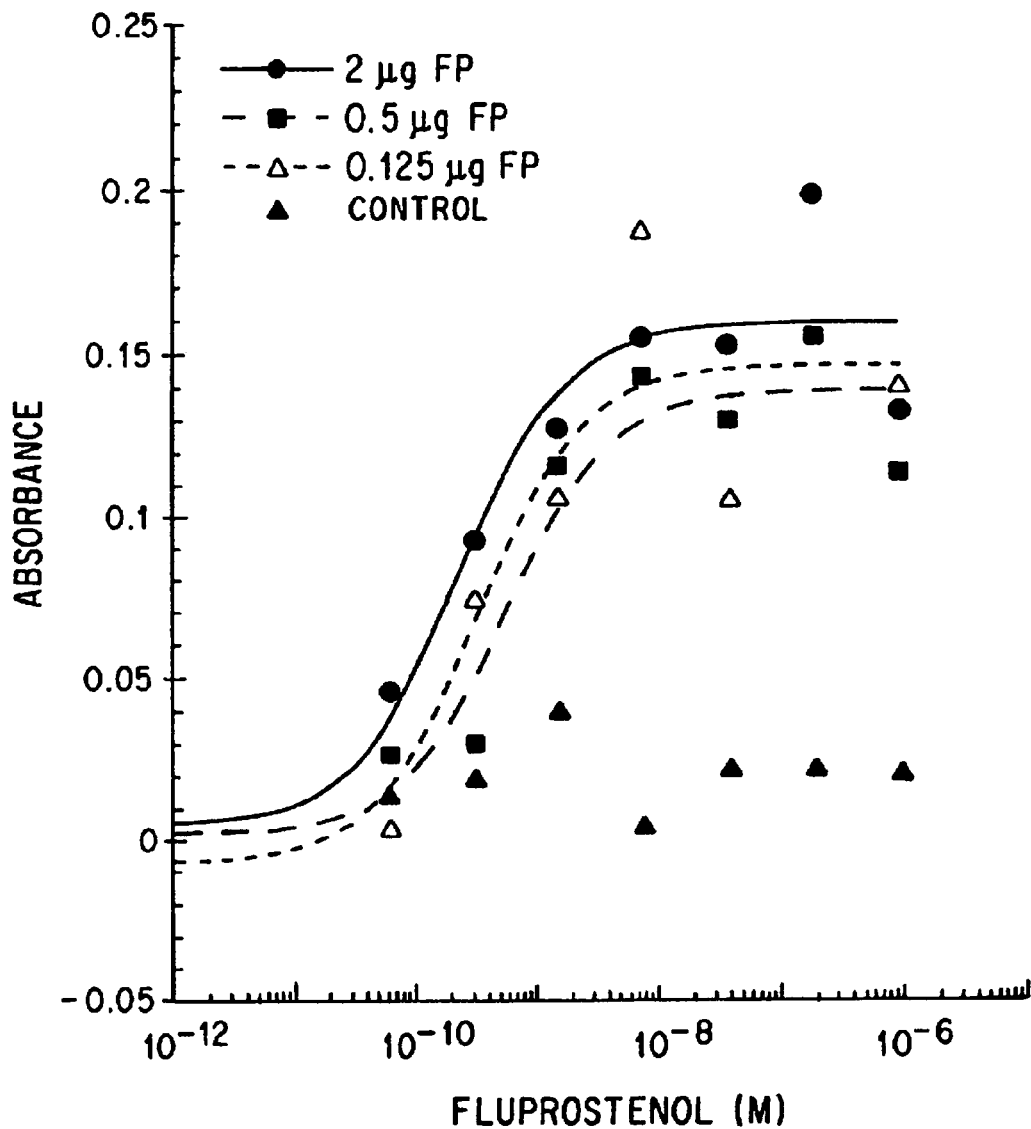
Figure 16:
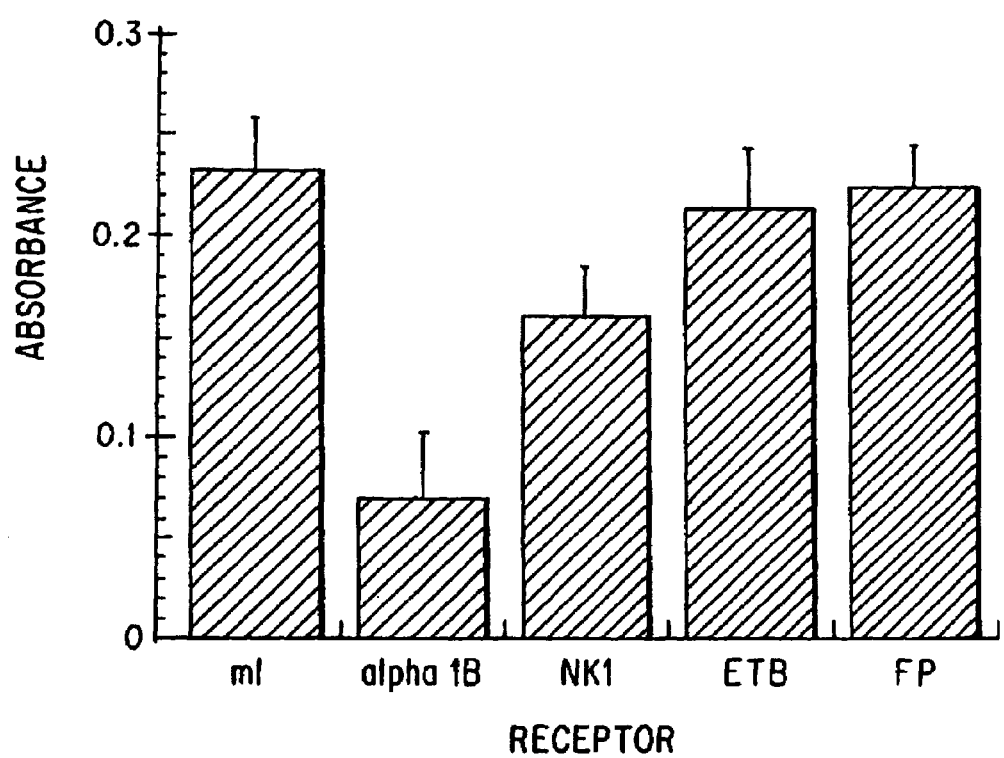
FIG. 16 illustrates the maximal ligand-induced responses of the indicated receptors, as assayed using cotransfected cultures using a Multiple Receptor Format similar to that described in FIG. 11. Ten cm plates of NIH 3T3 cells were transfected with 0.5 μg of each of the five test DNAs, 2.5 μg of D2 receptor cDNA, and 2.5 μg of β-gal cDNA. Seven doses of agonist ligands selective for each of the receptors were tested (m1/carbachol: α1B/phenylephrine. NK1/substance P: ETB/endothelin-3: FP/fluprostenol). Cells were incubated in wells of a 96 well plate for 4 days with each ligand. Maximal responses were calculated by fitting the data to a model of a single mass-action site. Separate experiments demonstrated that each of these ligands were unable to induce responses in the absence of its indicated target receptor.

One configuration of the Multiplex Receptor Format is illustrated in FIG. 11. In this example, several receptors cDNAs are cotmsfected with β-gal cDNA into a culture of NIH 3T3 cells. After addition of ligands an effective ligand/receptor interaction is identified by a positive β-gal response. Data supporting the feasibility of this approach is illustrated in FIG. 15. In these examples, no signal is lost when endothelin and prostenoid receptor DNA is substantially reduced in concentration. Empirical data using multiple receptors is illustrated in FIG. 16. In this example, ligand responses to muscarinic, adrenergic, neurokinin, endothelin and prostenoid receptor activation were assayed in cotransfected cultures. In this experiment an excess of inactive receptor DNA was used to simulate a 10 fold multiplexed assay (10 receptors assayed simultaneously).

Example 8

Disease Gene Assay and Identification

Figure 12:
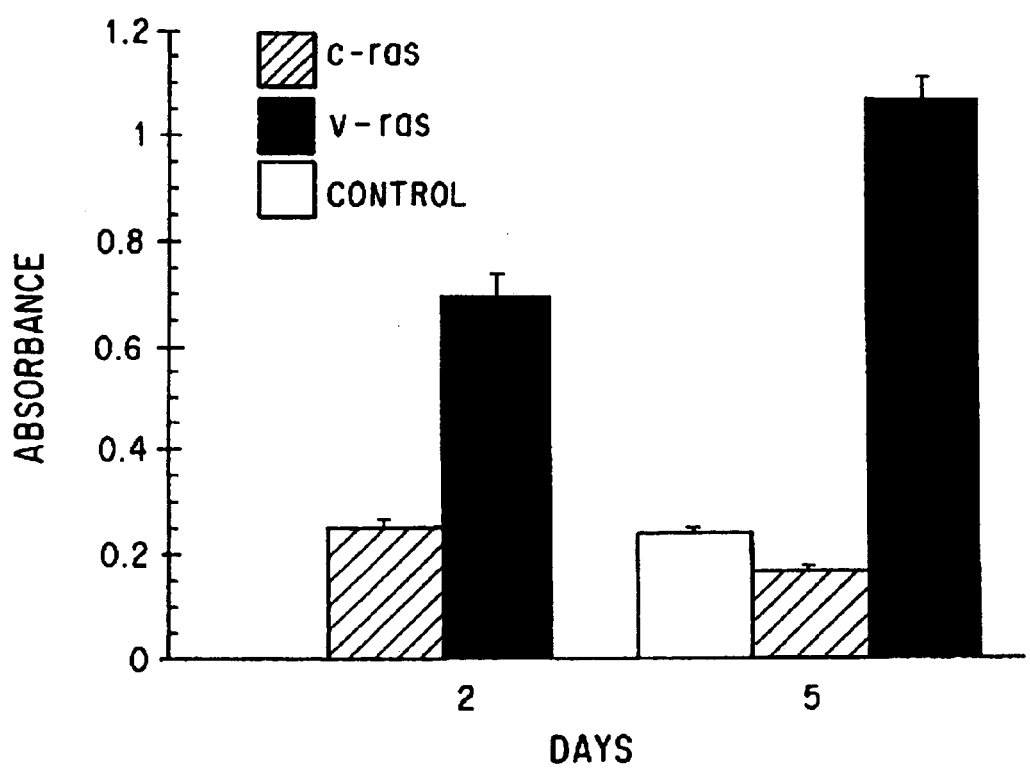
FIG. 12 illustrates the responses of cells to the oncogene V-ras. Six well plates of NIH 3T3 cells were transfected with 1 μg of V-ras or n-ras and 1 μg of 6-gal cDNA. Assays were performed using the Standard Single Receptor format as described in FIG. 5. Controls were performed using m5 receptor transfected cells without an activating ligand.

Many diseases are caused by mutations in receptors and/or associated signal transducing proteins. The best characterized examples are the oncogenes, but other examples include genes associated with retinitis pigmentosa, color blindness and insulin dependent or independent diabetes. Other examples will be well known to those skilled in the art. Among the best characterized oncogenes are mutant forms of the small G-protein ras. As illustrated in FIG. 12, mutant ras (v-ras), but not wild-rype ras (c-ras), is able to mediate significant responses in amplification assays. As summarized in Table 2, other oncogenes such as mutant forms of p53 and the G-protein G12 are able to mediate amplification responses. Also as noted in Example 6, a mutant form of the m5 receptor that is active in the absence of agonist was identified by amplification assays. Together these data indicate that amplification assays is a powerful approach to both the assay and idenfication of disease genes. The procedure for disease gene identification is as follows. 1) The coding region of a receptor suspected in a given disease is amplified by PCR. Amplifications can be performed using individuals or populations of individuals with disease. 2) The receptor is tested by amplification assays for activity in the absence of ligand, and/or inappropriate ligand sensitivity. By "inappropriate ligand sensitivity" is meant that a mutant form can be expected to respond to ligand at a lower concentration than the wild-type form. In addition, mutant forms' elevated activity will also be blocked by antagonist as shown, for example, in FIG. 13. Assays can be performed one at a time as in Example 6, or several patient DNAs could be tested simultaneously using the Multiplexed assays described in Example 7.

Example 9

Assay of Chimeric Receptors

Figure 17:
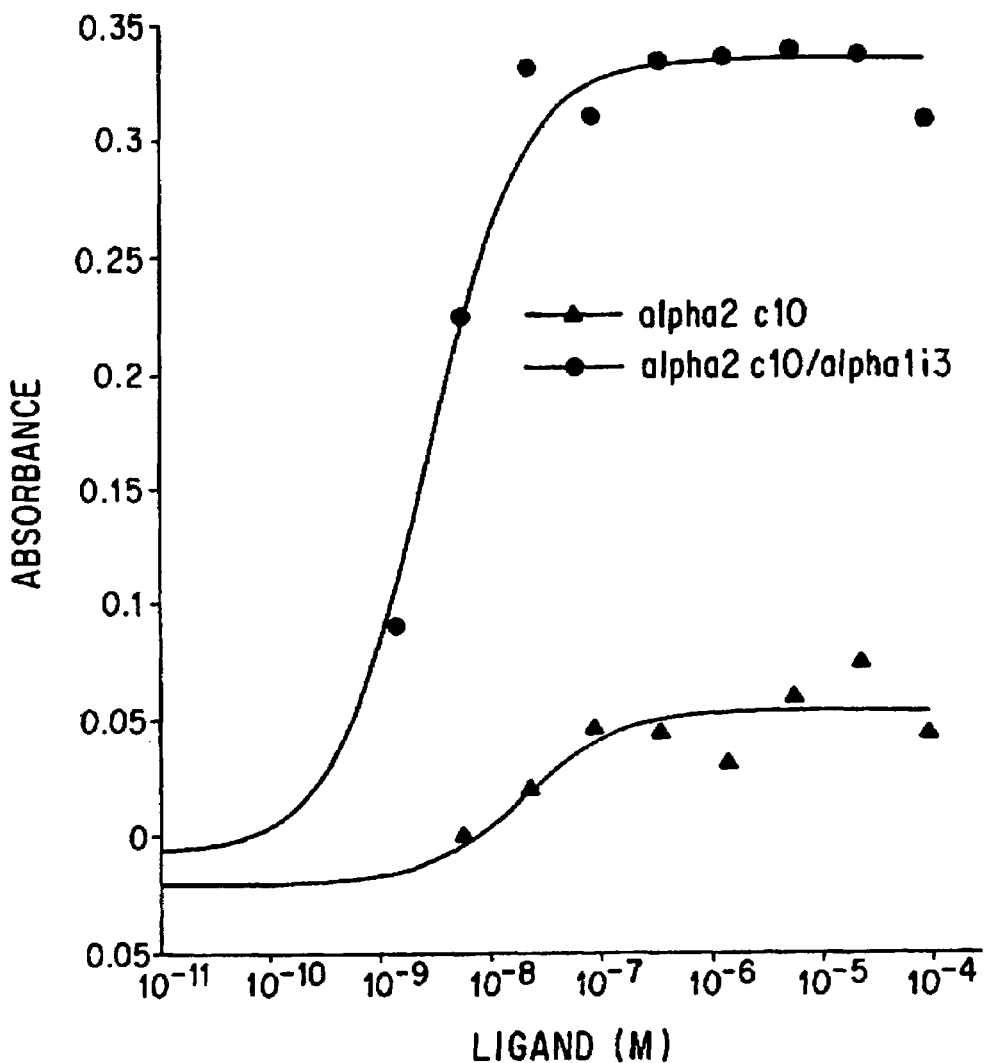
FIG. 17 illustrates the dose-response of wild-type and chimeric α2 adrenergic receptors for the agonist UK 14,304. The indicated doses of agonist were assayed using the Single Receptor Format. Five μg of receptor DNA and 5 μg of β-gal DNA were used for 10 cm plates. Receptors were incubated with agonist for five days. Data are the means of triplicate determinations. The lines are fits of the data to a single mass-action site of action by nonlinear regression. A chimeric construct of α2c10 was prepared using PCR and standing cloning techniques. Specifically, the entire i3 loop of the α2c10 was replaced with the majority of the corresponding α1Ai3 loop. β-galactosidase was assayed after incubation in ONPG for 24 hours with absorbance read at 420 in the spectrophotometer.
Figure 18:
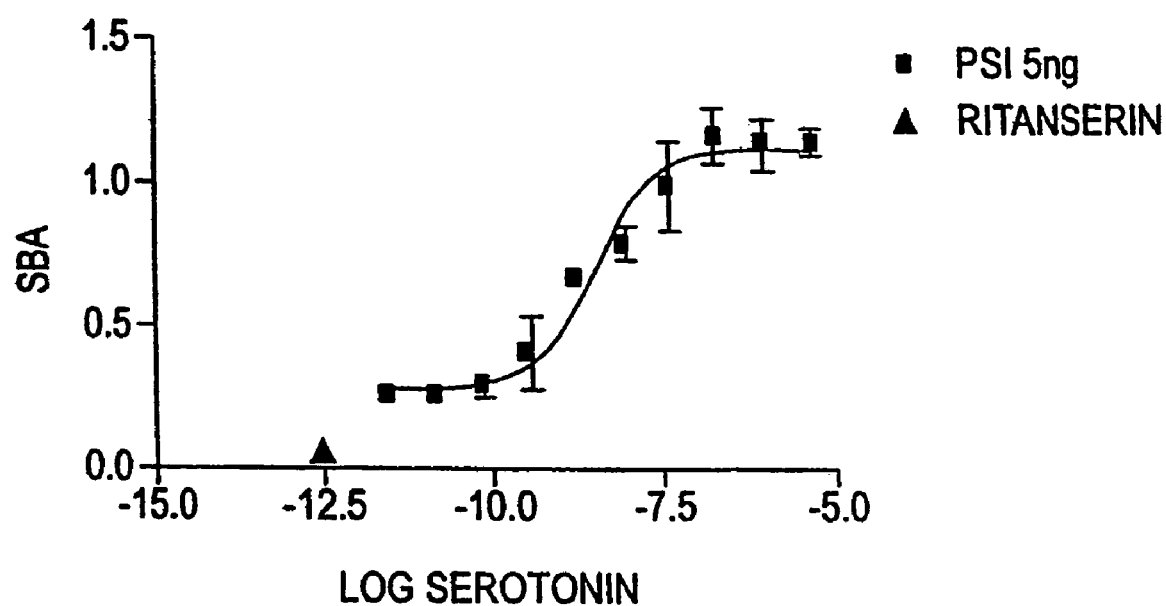
FIG. 18 shows the dose response relationship for serotonin at the 5-HT2A receptor as observed in R-SAT assays. Responses are plotted as the change in absorbance measured at 420 nm. Ten serial 1:5 dilutions of serotonin starting from 5 µM were tested. The squares depict the response of the 5-HT2A using the PSI.RTM. expression vector at a DNA concentration of 5 ng per well. The triangle depicts the response to 1 µM ritanserin. Data are from duplicate determinations at each drug concentration, where the error bars denote the standard error of the mean. The $EC_{50}$ for serotonin is 7 nM. Note the elevated basal activity of this receptor as documented by the inhibition below baseline seen with the inverse agonist ritanserin.
Figure 19:
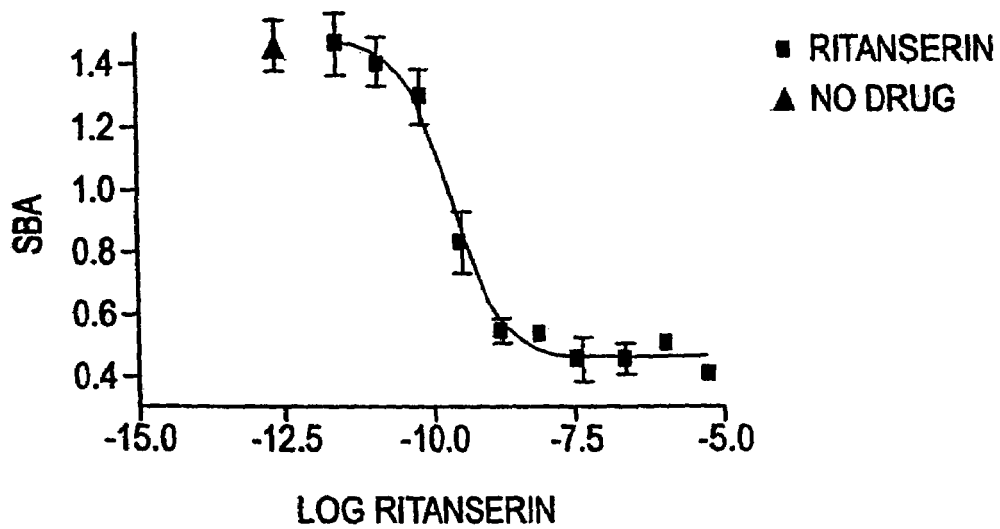
FIG. 19 shows the dose response relationship at the 5-HT2A receptor for the inverse agonist ritanserin as determined using R-SAT analysis. Responses are plotted as the change in absorbance measured at 420 nm. Ten serial 1:5 dilutions of drug starting from 5 µM were tested. The squares depict the data obtained for ritanserin, while the triangle denotes the basal, no drug, response. Data are from duplicate determinations at each drug concentration, where the error bars denote the standard error of the mean. The $EC_{50}$ for ritanserin is 140 pM. Ritanserin displays high affinity negative intrinsic activity at the 5-HT2A receptor.
Figure 20A:
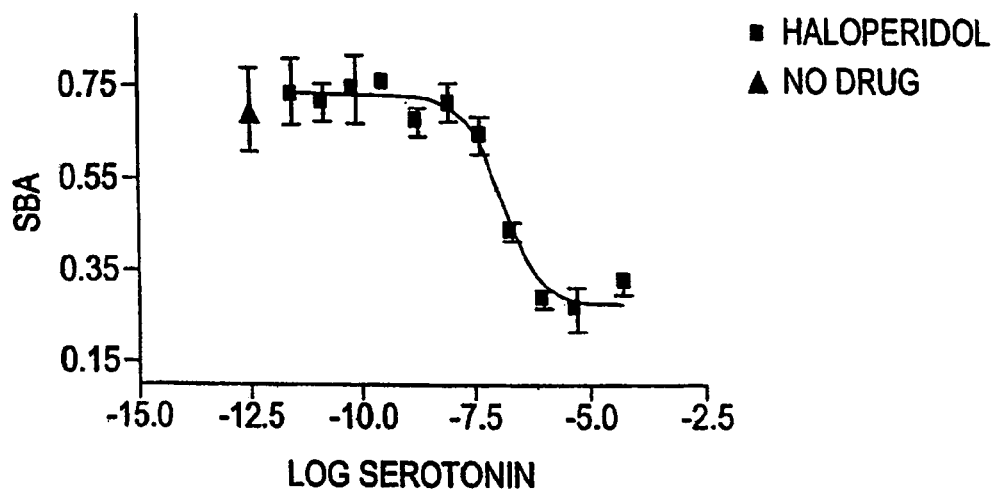
FIG. 20 shows the dose response relationship for two representative antipsychotics as inverse agonists of the 5-HT2A receptor as determined by R-SAT analysis. Responses are plotted as the change in absorbance measured at 420 nm. Ten serial 1:5 dilutions of drug starting from 5 µM were tested. The squares depict the data obtained for haloperidol in (A), and risperidone in (B), while the triangles denote the basal, no drug, response. Data are from duplicate determinations at each drug concentration, where the error bars denote the standard error of the mean. The $EC_{50}$ values are 120 nM for haloperidol and 1 µM for risperidone, respectively.
Figure 20B:
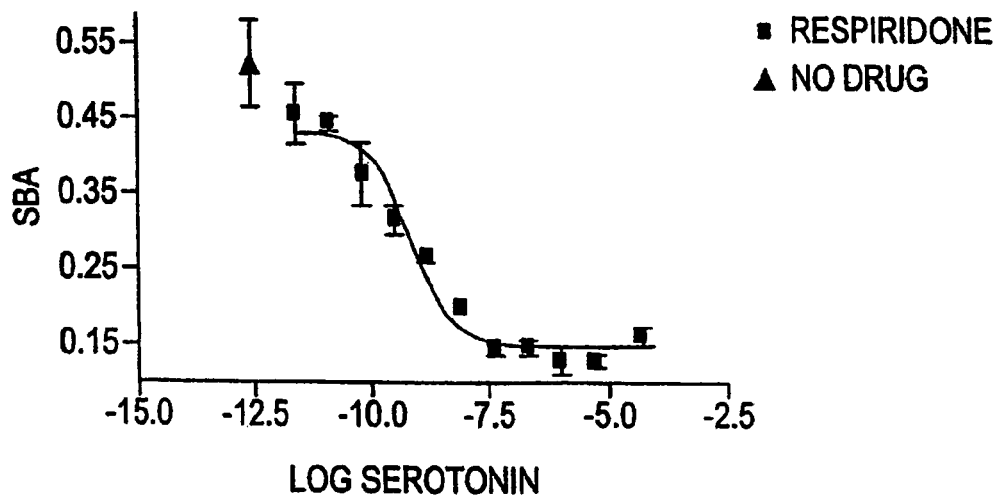

Many receptors that do not mediate robust responses in amplification assays can be engineered to mediate responses by changing their selectivity for signal transduction pathways. As illustrated in FIG. 17, the ability of α2 adrenergic receptors to mediate functional responses can be greatly amplified by inserting the third loop of the α1 receptor. α1 receptors efficiently couple to Gq, while α2 receptors more efficiently couple to Gi. As suggested by this data and others, the third loop is thought to be the primary determinant of coupling selectivity.

Example 10

Pharmacological Phenotype of the 5-HT2A Receptor

The functional receptor assay, Receptor Selection and Amplification Technology (R-SAT), as described herein, was used to investigate the pharmacological phenotype of the 5-HT2A receptor. The 5-HT2A receptor gene was amplified by nested PCR from brain cDNA using the-following oligodeoxynucleotides based on published sequences: 5'#1: 5'-agctccgggagaacagcatgta-3'; 5'#2: (SEQ ID NO:14) 5'-gagtgtggatccatcaaggtgaatggtgagcag-3' (SEQ ID NO:15); 3'#1: 5'-caatgaacagcatagcagcaa-3' (SEQ ID NO:16); 3'#2: 5'-ggtttcctctagaaaatagaagttaatttagatt-3' (SEQ ID NO:17) (Saltzman et. al., Biochem. Biophys. Res. Comm. 181(3), 1991, pp. 1469-1478).

The cDNA was obtained by reverse transcription of total RNA isolated from human brain tissue in accordance with standard techniques (see, Sambrook et al, supra). The human brain tissue was obtained from a 100-year old female free of neuropsychiatric disease. The PCR product was subdloned onto the TOPO PCR 2.1.RTM. vector (Invitrogen, Inc.) in accordance with the manufacturer's protocol. A Bam-H1 (blunted with T4 polymerase)-Not-1 DNA fragment containing the gene was subcloned into the mammalian expression vector PSI.RTM. (Promega, Inc.) for heterologous expression in R-SAT.

Varying doses of 5-HT2A receptor plasmid DNA were transfected into NIH 3T3 cells (at 70% confluence) using the transfection reagent Superfect.RTM. (Qiagen, Inc.). 5-HT2A receptor DNA transfection mixtures (per well of a 96-well cell culture dish) were composed of from 5 to 50 ng/well of receptor DNA, 25 ng/well of β-galactosidase plasmid DNA (in the PSI.RTM. vector), 50 μL of DMEM, and 15 μL of Superfect.RTM. This mixture was then augmented with additional DMEM (with 10% calf serum and 1% penicillin/streptomycin/glutamine) sufficient to incubate each well with 50 μL of the transfection mixture. Cells were transfected for 12 to 16 hours at 37° C. in a humidified environment supplemented with 5% $CO_2$, after which time the media was replaced by DMEM with 2% cyto-SF3 (Kemp Biotechnologies, Inc.) containing variable amounts of the compounds being tested.

Cells were grown in a humidified environment at 37° C. with 5% $CO_2$ for five days prior to visualization of β-galactosidase activity by replacing the media with the β-galactosidase substrate o-nitrophenyl-β-D-galactopyranoside (substantially as described in U.S. Pat. No. 5,707,798). All data were obtained by measuring the change in absorbance at 420 nm using an automated plate reader (BioTek EL 310). $EC_{50}$ values were calculated using the equation: $r=A+B(x/(x+c))$, where A=minimum response, B=maximum response minus minimum response, $c=EC_{50}$, r=response, and x=concentration of ligand. Curves were generated by least-squares fit using the program KaleidaGraph.RTM. (Abelbeck Software).

Since constitutive activity may be erroneously measured if experiments are conducted in the presence of minute amounts of agonist, a number of control experiments were performed to rule out the possibility that serotonin was present in the media. Firstly, only synthetic sera were used (cyto-SF3), because bovine calf serum may contain various monoamines or related receptor agonists. Second, experiments in which the amount of synthetic sera was about 2-5 times that routinely used did not result in a measurable increase in constitutive activity (data not shown). In addition, using other serotonin receptor subtypes in which constitutive activity has been measured (5-HT2B) revealed compounds that are neutral antagonists and others that are inverse agonists, arguing that competition for endogenous serotonin is not occurring (otherwise, all compounds would appear to be inverse agonists).

The results of this analysis of the 5-HT2A receptor are presented in FIG. 1, as a representative pharmacological profile as determined by R-SAT.

Based on the results obtained in this analysis, it was concluded that 1) the 5-HT2A receptor is functionally active in R-SAT, and that the data obtained are in agreement with previously published binding assays (C. A. Stockmneier et al., J. Pharm Exper. Ther. 266(3), 1993, pp. 1374-1384).

2) expression of 5-HT2A receptors using the PSI.RTM. vector results in the detection of constitutive activity. Under these experimental conditions, ritanserin inhibits receptor signaling below baseline (no drug) values, i.e. it is an inverse agonist (note ritanserin values in FIG. 1).

3) increasing the amount of DNA used for transfection increased the basal activity of the 5-HT2A receptor (5% constitutive activity at 5 ng/well vs. 11% constitutive activity at 50 ng/well; data not shown).

Upon detecting constitutive signaling with the 5-HT2A receptor, high DNA concentrations were subsequently used to augment basal responses and facilitate pharmacological analysis of inverse agonists. All subsequent studies utilized 50 ng/well of 5-HT2A receptor DNA. FIG. 2 shows the dose response relationship for ritanserin as a representative 5-HT2A receptor inverse agonist.

R-SAT was configured to assay simultaneously for compounds that exhibit both agonism and inverse agonism at this receptor subtype. Multiple 96-well plates of NIH 3T3 cells were transfected with 50 ng/well of 5-HT2A receptor DNA and screened against a 640-compound library of medically relevant drugs (RBI Inc, Natick, Mass.). All compounds were screened at concentrations of 300-500 nM, serotonin (1 µM) was used as a reference agonist, and ritanserin (1 µM) was used as a reference inverse agonist. The results of this screen for inverse agonism (for compounds with greater than 40% inhibition) at the 5-HT2A receptor are shown in Table 4 below.

TABLE 4

Screen for Inverse Agonism at 5-HT2A Receptors

| % INHIBITION | COMPOUND |
|---|---|
| 96 | TRIFLUPERIDOL |
| 92 | PIRENPIRONE |
| 90 | RITANSERIN |
| 87 | RISPERIDONE |
| 84 | BUTACLAMOL |
| 82 | SPIPERONE |
| 82 | KETANSERIN |
| 79 | MIANSERIN |
| 79 | METHIOTHEPIN |
| 77 | LOXAPINE |
| 76 | OCTOCLOTHEPIN |
| 75 | Mdl 26,630 3HCl |
| 75 | TRIFLOUPERAZINE |
| 75 | CINANSERIN |
| 74 | Dag kinase inhibitor |
| 69 | JL-18 (CLOZAPINE) |
| 68 | AMOXAPINE |
| 66 | CYPROHEPTADINE |
| 65 | CHLORPROMAZINE |
| 62 | METERGOLINE |
| 61 | FLUPHENAZINE |
| 57 | FLUSPIRILINE |
| 56 | THIORIDAZINE |
| 53 | Benztropine |
| 53 | 5-hydroxy-Ltryptophan |
| 52 | Promethazine |
| 52 | CLOZAPINE |
| 51 | Physostigmine |
| 45 | CIS-FLUPENTIXOL |
| 42 | PIMOZIDE |

In Table 4, all data are derived from the mean of duplicate determinations for each test compound, and are presented as a percentage inhibition referenced to ritanserin (90-100%). The data include all compounds detected in the screen that displayed a greater than 40% inhibition from basal, no drug, levels. All compounds that are known serotonergic drugs are italicized, and all drugs with known anti-psychotic activity are presented in bold.

The results of this screen are significant in that:

1) The screen identified nearly every antipsychotic drug in the compound library (18/19 at 30% inhibition or greater), documenting that these drugs are actually inverse agonists (not antagonists) at this receptor subtype.

2) There is selectivity to this interaction, as multiple classes of other neuropsychiatric agents (e.g., antidepressants and anticonvulsants) represented in the library are not inverse agonists at this receptor subtype.

3) The R-SAT technology is amenable to screening compounds for inverse agonism at the 5-HT2A receptor.

4) The R-SAT technology is amenable to screening individuals for constitutively activating mutations of the 5-HT2A receptor in an analogous manner to that presented above.

Having discovered that antipsychotics are inverse agonists of the 5-HT2A receptor, a detailed pharmacological analysis of many of these agents was performed to establish their potency and efficacy. FIG. 3 shows the dose response curves for two known antipsychotics, the typical agent haloperidol, and the atypical agent risperidone. Table 5 is a compilation of this detailed pharmacological analysis presented as negative log $EC_{50}$ values.

TABLE 5

Potency of Antipsychotics as Inverse Agonists at the 5-HT2A Receptor

| DRUG | Negative Log $EC_{50}$ |
|---|---|
| Sertindole | 10.12 ± 0.18 |
| Tefludazine | 9.02 ± 0.21 |
| Risperidone | 8.81 ± 0.05 |
| Spiperone | 8.70 ± 0.07 |
| Pimozide | 8.65 ± 0.04 |
| Amoxapine | 8.64 ± 0.13 |
| Loxapine | 8.49 ± 0.07 |
| Butaclamol | 8.49 ± 0.19 |
| Fluspirilene | 8.49 ± 0.14 |
| Clozapine | 8.17 ± 0.19 |
| Olanzapine | 8.17 ± 0.07 |
| JL-18 | 8.11 ± 0.13 |
| Cis-Flupentixol | 8.04 ± 0.10 |
| Fluphenazine | 7.85 ± 0.10 |
| Chlorpromazine | 7.70 ± 0.11 |
| Triflouperidol | 7.59 ± 0.09 |
| Thioridazine | 7.02 ± 0.18 |
| Triflouperazine | 6.76 ± 0.19 |
| Trans-Flupentixol | 6.77 ± 0.21 |
| Haloperidol | 6.79 ± 0.03 |
| Thiothixene | 6.43 ± 0.11 |
| Sulpiride | No Effect |
| Remoxipride | Agonist |
| Molindone | Agonist |

Table 5 above provides the molar negative log $EC_{50}$s for inhibition of constitutive activity derived from the mean of three separate dose response experiments (±standard error). Antipsychotics that are generally considered atypical are highlighted in bold.

These data allow one to draw the following conclusions regarding antipsychotics as inverse agonists of the 5-HT2A receptor:

1) Nearly all antipsychotics tested are potent inverse agonists of the 5-HT2A receptor. No similar activity of these drugs as inverse agonists at other potentially relevant monoamine receptors (5-HT1A, 5-HT1B, 5-HT2C, Dopamine D1, D2, D3, and D5, α-1B adrenergic, and muscarinic m5 receptors) has been noted (T. A. Spalding et al., supra; Nilsson, C. L., supra; Hall, D. A. and Strange, P. G., supra, E. L. Barker et al., supra; A. Newman-Tancredi et al., Brit. Jour. of Pharm. 120, pp. 737-739; P. A. Pauwels and F. C. Colpaert, Biochem. Pharm. 50(10), pp. 1651-1658; and D. R. Thomas et al., J. of Receptor and Signal Transduction Research 15(1-4), pp. 199-211). The correlation between this singular molecular pharmacological mechanism and efficacy of a drug as an antipsychotic suggests that this is a fundamental mechanism of action of this class of drug.

2) The atypical antipsychotic agents are amongst the most potent of 5-HT2A receptor inverse agonists; thus, potent and selective 5-HT2A inverse agonism should be a property of novel antipsychotic drugs with improved clinical profiles.

3) Since antipsychotics as a class possess the intrinsic activity to reduce constitutive signal transduction mediated by the 5-HT2A receptors, any condition that favors increased basal activity of this receptor may be contributory to, or causative of, psychosis and/or schizophrenia.

It is apparent that the singular molecular property of inverse agonism at the 5-HT2A receptor is common to nearly all compounds with efficacy as an antipsychotic. To further support the uniqueness of this correlation, a large series of antipsychotics were pharmacologically profiled against the human 5-HT2C receptor. This receptor was chosen because: 1) it is genetically and pharmacologically related to the 5-HT2A receptor, 2) the receptor RNA and protein are expressed in human brain regions critical to higher cognitive functioning, and 3) some evidence exists to support the notion that antagonism of this receptor is relevant to the mechanism of action of antipsychotic drugs. The wild type human 5-HT2C receptor was PCR-cloned from human cortical cDNA by standard molecular biological techniques familiar to those skilled in the art. The receptor construct was subdloned into the PSI.RTM. mammalian expression vector, and verified by DNA sequencing. Transfection of 50 ng per well of receptor DNA (identical to the amount used for 5-HT2A assays) revealed readily measurable constitutive activity. Thirty-six antipsychotics were pharmacologically assayed against the 5-HT2C receptor as both agonists and inverse agonists. Table 6 reports the negative log $EC_{50}$ for these compounds as inverse agonists at both the 5-HT2A and 5-HT2C receptors.

TABLE 6

Potency of Antipsychotics as Inverse Agonists at 5-HT2A and 5-HT2C Receptors

| DRUG | 5-HT2A Receptor Negative Log $EC_{50}$ | 5-HT2C Receptor Negative Log $EC_{50}$ |
|---|---|---|
| Sertindole | 10.12 ±− 0.18 | 7.64 ± 0.42 |
| Octoclothepin | 9.74 ± 0.98 | 8.52 ± 0.56 |
| Tefludazine | 9.02 ± 0.21 | 8.28 ± 0.49 |
| Respiridone | 8.81 ± 0.05 | <5.0 |
| Tiospirone | 8.74 ± 0.67 | 6.29 ± 0.53 |
| Spiperone | 8.70 ± 0.07 | No Intrinsic Activity |
| Pimozide | 8.65 ± 0.04 | No Intrinsic Activity |
| Amoxapine | 8.64 ± 0.13 | 6.92 ± 0.34 |
| Clothiapine | 8.55 ± 1.09 | 6.32 ± 0.57 |
| Butaclamol | 8.49 ± 0.19 | No Intrinsic Activity |
| Loxapine | 8.49 ± 0.07 | 6.30 ± 0.32 |
| Fluspirilene | 8.19 ± 0.14 | No Intrinsic Activity |
| Clozapine | 8.17 ± 0.19 | 6.60 ± 0.64 |
| Olanzapine | 8.17 ± 0.07 | 6.36 ± 0.47 |
| JL-18 | 8.11 ± 0.13 | 6.09 ± 0.45 |
| Cis-Flupentixol | 8.04 ± 0.10 | No Intrinsic Activity |
| Fluphenazine | 7.85 ± 0.10 | <5.0 |
| Amperozide | 7.80 ± 0.82 | No Intrinsic Activity |
| Chlorproethizene | 7.70 ± 0.33 | <5.0 |
| Chlorpromazine | 7.70 ± 0.11 | No Intrinsic Activity |
| Triflouperidol | 7.59 ± 0.09 | <5.0 |
| Perlapine | 7.52 ± 0.49 | 5.89 ± 1.17 |
| Promazine | 7.10 ± 1.27 | Agonist |
| Moperone | 7.03 ± 0.59 | No Intrinsic Activity |
| Thioridazine | 7.02 ± 0.18 | No Intrinsic Activity |
| Mesioridazine | 7.00 ± 0.30 | No Intrinsic Activity |
| Melperone | 6.96 ± 0.56 | No Intrinsic Activity |
| Haloperidol | 6.79 ± 0.03 | No Intrinsic Activity |
| Trans-Flupentixol | 6.77 ± 0.21 | 5.55 ± 0.37 |
| Triflouperazine | 6.76 ± 0.19 | No Intrinsic Activity |
| Bromperidol | 6.66 ± 0.76 | No Intrinsic Activity |
| Prothypendyl | 6.60 ± 0.44 | Agonist |
| Quietapine | 6.57 ± 0.80 | No Intrinsic Activity |
| Thiothixene | 6.43 ± 0.11 | No Intrinsic Activity |
| Sulpiride | No Intrinsic Activity | No Intrinsic Activity |
| Remoxipride | Agonist | No Intrinsic Activity |
| Molindone | Agonist | No Intrinsic Activity |

The following conclusions can be drawn from this data:

1) The correlation between inverse agonism and efficacy as an antipsychotic is apparent at the 5-HT2A receptor (33 of 36 compounds), but does not exist at the 5-HT2C receptor (12 of 36 compounds).

2) High potency inverse agonism at the 5-HT2A receptor is a property that many of the "atypical" antipsychotics share, yet no such correlation between compounds with improved clinical characteristics ("atypicals") and 5-HT2C receptor intrinsic activity can be drawn.

To identify novel compounds as potential antipsychotic drugs, the 5-HT2A inverse agonist R-SAT assay was formatted to conduct high-throughput screening of large libraries of organic compounds. For these purposes, the constitutive basal response of the 5-HT2A receptor was augmented by the addition of the a subunit of the heterotrimeric G-protein Gq into the transfection mixtures. Gq is the signaling molecule utilized by the 5-HT2A receptor to functionally signal in cells, and coexpressing Gq with other GPCR's has been previously shown to constitutively activate receptors in this class (Burstein, E. S., et al., FEBS Lett. 363, 1995, pp. 261-263).

The 5-HT2A inverse agonist assay was used to screen 135,000 organic compounds for 5-HT2A inverse agonist activity. The compounds examined were from a library of structurally diverse organic molecules with an average molecular weight of 350 daltons. The compounds were dissolved in DMSO and plated onto microtiter plates with one compound in each well and either 96 or 384 compounds on each plate. The compounds were diluted to a concentration. of 3000 nM, incubated in the presence of transfected cells for a period of five days, after which time β-galactosidase activity was measured to determine the functional response of potential inverse agonists. These compounds were also screened against the muscarinic m5 receptor, in an analogous fashion, to provide a measure of selectivity for the active compounds.

Of the 135,000 compounds tested in this manner, 511 were identified that repressed the 5-HT2A basal activity in replicate samples greater than 50% of that observed with the control inverse agonist, 100 nM ritanserin. Of the 511 compounds that repressed 5-HT2A constitutive activity greater than 50% at 3000 nM, 322 compounds repressed significantly at 300 nM as well. Of these, 252 compounds displayed greater than 10-fold selectivity for 5-HT2A inverse agonism compared to inverse agonism at the muscarinic m5 receptor.

Of the 252 5-HT2A selective compounds, 111 are related in structure to the known antipsychotic haloperidol, and 64 compounds are structurally related to the tricyclic antidepressants compounds with known antipsychotic activity. Examples of these are the compound AC121394 in the haloperidol class, and compound AC116399 in the tricyclic class (see FIG. 4). The successful screening of compounds with 5-HT2A inverse activity that are related in structure to known antipsychotics is a direct demonstration that one can identify compounds with potentially improved antipsychotic activity.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The disclosures of all references cited herein are incorporated by reference in their entireties.

What is claimed is:

1. A method of determining whether a substance is a ligand of a constitutively active wild-type 5HT2A receptor, wherein said 5HT2A receptor has a basal response, said method comprising:

obtaining a test cell culture which comprises a first population of cells and a second population of cells, wherein DNA coding for said 5HT2A receptor and also DNA encoding a marker indicative of the extent of cellular proliferation has been introduced into said first population of cells such that the amount of said marker produced by said first population of cells is influenced by the degree to which said 5HT2A receptor is active, and wherein the amount of marker produced by said second population of cells is not influenced by the degree to which said 5HT2A receptor is active or wherein said second population of cells does not comprise DNA coding for said marker;

contacting said test cell culture with a test substance which is a potential ligand of said 5HT2A receptor;

obtaining a control cell culture, said control cell culture comprising cells comprising said DNA coding for said 5HT2A receptor and said DNA coding for said marker, wherein said control cell culture has not been contacted with said test substance;

determining whether the extent of proliferation of said first population of cells in said test cell culture is significantly greater or significantly less than the extent of proliferation of said cells in said control cell culture by comparing the amount of marker activity produced by said first population of cells in said test culture to the amount of marker activity produced by said cells in said control culture, wherein said test substance is an agonist of said 5HT2A receptor if the extent of proliferation of said first population of cells in said test culture is significantly greater than the extent of proliferation of said cells in said control culture and wherein said test substance is an antagonist or inverse agonist of said 5HT2A receptor if the extent of proliferation of said first population of cells in said test culture is significantly less than the extent of proliferation of said cells in said control culture.

2. The method of claim 1, wherein said determining step is performed by measuring the amount of said marker produced by said test culture at a time after contacting said test cell culture with said test substance which is prior to the time at which foci resulting from the proliferation of said first population of cells would be visible and by measuring the amount of said marker produced by said control cell culture at the same time as the amount of said marker in said test culture was measured.

3. The method of claim 1, wherein said determining step is performed within two weeks of the day that said test cell culture was contacted with said substance.

4. The method of claim 1, wherein said determining step is performed within 4 days of the day that said test cell culture was contacted with said substance.

5. The method of claim 1, further comprising contacting said test cell culture and said control cell culture with a substance known to be an agonist of said 5HT2A receptor.

6. The method of claim 1, further comprising contacting said test cell culture and said cell control culture with a substance known to be an antagonist of said 5HT2A receptor.

7. The method of claim 1, wherein said test cell culture and said control cell culture are obtained by introducing said DNA coding for said 5HT2A receptor and said DNA coding for said marker into a starting cell culture and dividing said starting cell culture into multiple aliquots.

8. The method of claim 1, wherein said determining step comprises determining whether said substance inhibits said basal receptor response, wherein said substance is an inverse agonist of said 5HT2A receptor if said substance inhibits said basal receptor response of said 5HT2A receptor.

9. The method of claim 1, wherein said second population of cells comprises cells selected from the group consisting of:
   (a) cells which do not comprise DNA coding for said marker;
   (b) cells which do not comprise DNA coding for said 5HT2A receptor;
   (c) cells which comprise DNA coding for said 5HT2A receptor but not DNA coding for said marker;
   (d) cells which comprise DNA coding for said marker but not DNA coding for said 5HT2A receptor; and
   (e) a combination of two or more of the cells recited in (a)-(d).

10. The method of claim 1, wherein said method is a high throughput screening assay.

11. The method of claim 1, wherein said method comprises determining whether said test compound is an inverse agonist of said 5HT2A receptor.

12. The method of claim 1, wherein DNA coding for an α subunit of a Gq protein has been introduced into said first population of cells and into said control culture.

13. A method of determining whether a substance is a ligand of a constitutively active wild-type 5HT2A receptor, wherein said 5HT2A receptor has a basal response, said method comprising,
   obtaining a test cell culture which comprises a first population of cells and a second population of cells, wherein DNA coding for said 5HT2A receptor and also DNA encoding a marker indicative of the extent of cellular proliferation has been introduced into said first population of cells such that the amount of said marker produced by said first population of cells is influenced by the degree to which said 5HT2A receptor is active, and wherein the amount of said marker produced by said second population of cells is not influenced by the degree to which said 5HT2A receptor is active or wherein said second population of cells does not comprise DNA coding for said marker;
   contacting said test cell culture with a test substance which is a potential ligand of said 5HT2A receptor; and
   determining whether the test substance confers a competitive advantage or a competitive disadvantage on the cells in said first population of said test culture relative to the cells in said second population of said test culture by measuring the amount of said marker produced by said test culture.

14. The method of claim 13, wherein said determining step is performed by measuring the amount of said marker produced by said test culture at a time after contacting said test cell culture with said test substance which is prior to the time at which foci resulting from the proliferation of said first population of cells would be visible.

15. The method of claim 13, wherein said determining step is performed within two weeks of the day that said test cell culture was contacted with said substance.

16. The method of claim 13, wherein said determining step is performed within 4 days of the day that said test cell culture was contacted with said substance.

17. The method of claim 13, further comprising contacting said test cell culture with a substance known to be an agonist of said 5HT2A receptor.

18. The method of claim 13, further comprising contacting said test cell culture with a substance known to be an antagonist of said 5HT2A receptor.

19. The method of claim 13, wherein said determining step comprises determining whether said substance inhibits said basal receptor response, wherein said substance is an inverse agonist of said 5HT2A receptor if said substance inhibits said basal receptor response of said 5HT2A receptor.

20. The method of claim 13, wherein said second population of cells comprises cells selected from the group consisting of
   (a) cells which do not comprise DNA coding for said marker;
   (b) cells which,do not comprise DNA coding for said 5HT2A receptor;
   (c) cells which comprise DNA coding for said receptor but not DNA coding for said marker;
   (d) cells which comprise DNA coding for said marker but not DNA coding for said 5HT2A receptor; and
   (e) a combination of two or more of the cells recited in (a)-(d).

21. The method of claim 13, wherein said method is a high throughput screening assay.

22. The method of claim 13, wherein said method comprises determining whether said test compound is an inverse agonist of said 5HT2A receptor.

23. The method of claim 13, wherein DNA coding for an α subunit of a Gq protein has been introduced into said first population of cells.

24. The method of claim 13, wherein 5-50 ng of DNA coding for said 5HT2A receptor has been introduced into said first population of cells.

25. A method of determining whether a substance is a ligand of a constitutively active wild-type 5HT2A receptor, wherein said 5HT2A receptor has a basal receptor response, said method comprising:
   obtaining a test cell culture which comprises a first population of cells and a second population of cells, wherein DNA coding for said 5HT2A receptor and also DNA encoding a marker indicative of the extent of cellular proliferation has been introduced into said first population of cells such that the amount of said marker produced by said first population of cells is influenced by the degree to which said 5HT2A receptor is active, wherein the transcription of said DNA coding for said marker is not under the control of said 5HT2A receptor, and wherein the amount of marker in said second population of cells is not influenced by the degree to which said 5HT2A receptor is active or wherein said second population of cells does not comprise said DNA coding for said marker;
   contacting said test cell culture with a test substance which is a potential ligand of said 5HT2A receptor;
   obtaining a control cell culture, said control cell culture comprising cells comprising said DNA coding for said 5HT2A receptor and said DNA coding for said marker, wherein said control cell culture has not been contacted with said test substance;

determining whether the extent of proliferation of said first population of cells in said test cell culture is significantly greater or significantly less than the extent of proliferation of said cells in said control cell culture by comparing the amount of marker activity produced by said first population of cells in said test culture to the amount of marker activity produced by said cells in said control culture, wherein said test substance is an agonist of said 5HT2A receptor if the extent of proliferation of said first population of cells in said test culture is significantly greater than the extent of proliferation of said cells in said control culture and wherein said test substance is an antagonist or inverse agonist of said 5HT2A receptor if the extent of proliferation of said first population of cells in said test culture is significantly less than the extent of proliferation of said cells in said control culture.

26. The method of claim 25, wherein said determining step comprises determining whether said substance inhibits said basal receptor response, wherein said substance is an inverse agonist of said 5HT2A receptor if said substance inhibits said basal receptor response of said 5HT2A receptor.

27. The method of claim 25, wherein said second population of cells comprises cells selected from the group consisting of:
(a) cells which do not comprise DNA coding for said marker;
(b) cells which do not comprise DNA coding for said 5HT2A receptor;
(c) cells which comprise DNA coding for said receptor but not DNA coding for said marker;
(d) cells which comprise DNA coding for said marker but not DNA coding for said 5HT2A receptor; and
(e) a combination of two or more of the cells recited in (a)-(d).

28. The method of claim 25, wherein said method is a high throughput screening assay.

29. The method of claim 25, wherein said method comprises determining whether said test compound is an inverse agonist of said 5HT2A receptor.

30. The method of claim 25, wherein DNA coding for an α subunit of a Gq protein has been introduced into said first population of cells and into said control culture.

31. The method of claim 25, wherein 5-50 ng of DNA coding for said 5HT2A receptor has been introduced into said first population of cells.

32. A method of determining whether a substance is a ligand of a constitutively active wild-type 5HT2A receptor, wherein said 5HT2A receptor has a basal response, said method comprising:
obtaining a test cell culture which comprises a first population of cells and a second population of cells, wherein DNA coding for a plurality of receptors and also DNA encoding a marker indicative of the extent of cellular proliferation has been introduced into said first population of cells such that the amount of said marker produced by said first population of cells is influenced by the degree to which said plurality of receptors are active, and wherein the amount of said marker produced by said second population of cells is not influenced by the degree to which said plurality of receptors are active or wherein said second population of cells does not comprise said DNA coding for said marker, wherein at least one of said plurality of receptors is a constitutively active wild-type 5HT2A receptor, wherein said 5HT2A receptor has a basal or constitutive receptor response;
contacting said test cell culture with a test substance which is a potential ligand of said 5HT2A receptor;
obtaining a control cell culture, said control cell culture comprising cells comprising said DNA coding for said plurality of receptors and said DNA coding for said marker, wherein said control cell culture has not been contacted with said test substance and wherein at least one of said plurality of receptors is a constitutive active wild type 5HT2A receptor;
determining whether the extent of proliferation of cells in said first population of cells in said test cell culture is significantly greater or significantly less than the extent of proliferation of said cells in said control cell culture by comparing the amount of marker activity produced by said first population of cells in said test culture to the amount of marker activity produced by said cells in said control culture, wherein said test substance is an agonist of said 5HT2A receptor if the extent of proliferation of cells in said first population of cells in said test culture which comprise DNA coding for said 5HT2A receptor is significantly greater than the extent of proliferation of said cells in said control culture which comprise DNA coding for said 5HT2A receptor and wherein said test substance is an antagonist or inverse agonist of said 5HT2A receptor if the extent of proliferation of cells in said first population of cells in said test culture which comprise DNA coding for said 5HT2A receptor is significantly less than the extent of proliferation of cells in said control culture which comprise DNA coding for said 5HT2A receptor.

33. The method of claim 32, wherein DNA encoding a plurality of markers has been introduced into said cells comprising said DNA coding for said plurality of receptors such that cells comprising DNA encoding a given receptor comprise DNA encoding a different marker than cells comprising DNA encoding the other receptors.

34. The method of claim 32, wherein said determining step is performed by measuring the amount of said marker produced by said test culture at a time after contacting said test cell culture with said test substance which is prior to the time at which foci resulting from the proliferation of said first population of cells would be visible and by measuring the amount of said marker produced by said control cell culture at the same time as the amount of said marker in said test culture was measured.

35. The method of claim 32, wherein said determining step is performed within two weeks of the day that said test cell culture was contacted with said substance.

36. The method of claim 32, wherein said determining step is performed within 4 days of the day that said test cell culture was contacted with said substance.

37. The method of claim 32, further comprising contacting said test cell culture and said control cell culture with a substance known to be an agonist of said 5HT2A receptor.

38. The method of claim 32, further comprising contacting said test cell culture and said cell control culture with a substance known to be an antagonist of said 5HT2A receptor.

39. The method of claim 32, wherein said test cell culture and said control cell culture are obtained by introducing DNA coding for said plurality of receptors and DNA coding for said marker into a starting cell culture and dividing said starting cell culture into multiple aliquots.

40. The method of claim 32, wherein said determining step comprises determining whether said substance inhibits said basal receptor response of said 5HT2A receptor, wherein said substance is an inverse agonist of said 5HT2A receptor if said substance inhibits said basal receptor response of said 5HT2A receptor.

41. The method of claim 32, wherein said second population of cells comprises cells selected from the group consisting of:
(a) cells which do not comprise DNA coding for said marker;
(b) cells which do not comprise DNA encoding any of said plurality of receptors;
(c) cells which comprise DNA encoding at least one of said plurality of receptors but not DNA coding for said marker;
(d) cells which comprise DNA coding for said marker but not DNA encoding any of said plurality of receptors; and
(e) a combination of two or more of the cells recited in (a)-(d).

42. The method of claim 32, wherein said method is a high throughput screening assay.

43. The method of claim 32, wherein said method comprises determining whether said test compound is an inverse agonist of said 5HT2A receptor.

44. The method of claim 32, wherein DNA coding for an α subunit of a Gq protein has been introduced into said first population of cells and into said control culture.

45. The method of claim 32, wherein 5-50 ng of DNA coding for said 5HT2A receptor has been introduced into said first population of cells.

46. A method of determining whether a substance is a ligand of a constitutively active wild-type 5HT2A receptor, wherein said 5HT2A receptor has a basal response, said method comprising,
obtaining a test cell culture which comprises a first population of cells and a second population of cells, wherein DNA coding for a plurality of receptors and also DNA encoding a marker indicative of the extent of cellular proliferation has been introduced into said first population of cells such that the amount of said marker produced by said first population of cells is influenced by the degree to which said plurality of receptors are active, and wherein the amount of said marker in said second population of cells is not influenced by the degree to which said plurality of receptors are active or wherein said second population of cells does not comprise said DNA coding for said marker wherein at least one of said plurality of receptors is a constitutively active wild-type 5HT2A receptor, wherein said 5HT2A receptor has a basal response;
contacting said test cell culture with a test substance which is a potential ligand of said 5HT2A receptor; and
determining whether the test substance confers a competitive advantage or a competitive disadvantage on cells in said first population of said test culture which express said 5HT2A receptor relative to the cells in said second population of said test culture which comprise said 5HT2A receptor by measuring the amount of said marker produced by said test culture.

47. The method of claim 46, wherein DNA encoding a plurality of markers has been introduced into said cells comprising said DNA coding for said plurality of receptors such that cells comprising DNA encoding a given receptor comprise DNA encoding a different marker than cells comprising DNA encoding the other receptors.

48. The method of claim 46, wherein said determining step is performed by measuring the amount of said marker produced by said test culture at a time after contacting said test cell culture with said test substance which is prior to the time at which foci resulting from the proliferation of said first population of cells would be visible.

49. The method of claim 46, wherein said determining step is performed within two weeks of the day that said test cell culture was contacted with said substance.

50. The method of claim 46, wherein said determining step is performed within 4 days of the day that said test cell culture was contacted with said substance.

51. The method of claim 46, further comprising contacting said test cell culture with a substance known to be an agonist of said 5HT2A receptor.

52. The method of claim 46, further comprising contacting said test cell culture with a substance known to be an antagonist of said 5HT2A receptor.

53. The method of claim 46, wherein said determining step comprises determining whether said substance inhibits said basal receptor response of said 5HT2A receptor wherein said substance is an inverse agonist of said 5HT2A receptor if said substance inhibits said basal receptor response of said 5HT2A receptor.

54. The method of claim 46, wherein said second population of cells comprises cells selected from the group consisting of:
(a) cells which do not comprise DNA coding for said marker;
(b) cells which do not comprise DNA encoding any of said plurality of receptors;
(c) cells which comprise DNA encoding at least one of said plurality of receptors but not DNA coding for said marker;
(d) cells which comprise DNA coding for said marker but not DNA encoding any of said plurality of receptors; and
(e) a combination of two or more of the cells recited in (a)-(d).

55. The method of claim 46, wherein said method is a high throughput screening assay.

56. The method of claim 46, wherein said method comprises determining whether said test compound is an inverse agonist of said 5HT2A receptor.

57. The method of claim 46, wherein DNA coding for an α subunit of a Gq protein has been introduced into said first population of cells.

58. The method of claim 46, wherein 5-50 ng of DNA coding for said 5HT2A receptor has been introduced into said first population of cells.

59. A method of determining whether a substance is a ligand of a constitutively active wild-type 5HT2A receptor, wherein said 5HT2A receptor has a basal response, said method comprising:
obtaining a test cell culture which comprises a first population of cells and a second population of cells, wherein DNA coding for a plurality of receptors and also DNA encoding a marker indicative of the extent of cellular proliferation has been introduced into said first population of cells such that the amount of said marker produced by said first population of cells is influenced by the degree to which said plurality of receptors are active, wherein the transcription of said DNA coding for said marker is not under the control of any of said plurality of receptors, and wherein the amount of said marker produced by said second population of cells is not influenced by the degree to which said plurality of receptors are active or wherein said second population of cells does not comprise said DNA coding for said marker, wherein at least one of said plurality of receptors is a 5HT2A receptor;
contacting said test cell culture with a test substance which is a potential ligand of said 5HT2A receptor;

obtaining a control cell culture, said control cell culture comprising cells comprising said DNA coding for said plurality of receptors and said DNA coding for said marker, wherein said control cell culture has not been contacted with said test substance and wherein at least one of said plurality of receptors is a constitutively active wild type 5HT2A receptor;

determining whether the extent of proliferation of said first population of cells in said test cell culture is significantly greater or significantly less than the extent of proliferation of said cells in said control cell culture by comparing the amount of marker activity produced by said first population of cells in said test culture which comprise DNA coding for said 5HT2A receptor to the amount of marker activity produced by said cells in said control culture which comprise DNA coding for said 5HT2A receptor, wherein said test substance is an agonist of said 5HT2A receptor if the extent of proliferation of said first population of cells in said test culture which comprise DNA coding for said 5HT2A receptor is significantly greater than the extent of proliferation of said cells in said control culture which comprise DNA coding for said 5HT2A receptor and wherein said test substance is an antagonist or inverse agonist of said 5HT2A receptor if the extent of proliferation of said first population of cells in said test culture which comprise DNA coding for said 5HT2A receptor is significantly less than the extent of proliferation of said cells in said control culture which comprise DNA coding for said 5HT2A receptor.

60. The method of claim 59, wherein said determining step comprises determining whether said substance inhibits said basal receptor response of said 5HT2A receptor, wherein said substance is an inverse agonist of said 5HT2A receptor if said substance inhibits said basal receptor response of said 5HT2A receptor.

61. The method of claim 59, wherein said second population of cells comprises cells selected from the group consisting of:
(a) cells which do not comprise DNA coding for said marker;
(b) cells which do not comprise DNA encoding any of said plurality of receptors;
(c) cells which comprise DNA encoding at least one of said plurality of receptors but not DNA coding for said marker;
(d) cells which comprise DNA coding for said marker but not DNA encoding any of said plurality of receptors; and
(e) a combination of two or more of the cells recited in (a)-(d).

62. The method of claim 59, wherein said method is a high throughput screening assay.

63. The method of claim 59, wherein said method comprises determining whether said test compound is an inverse agonist of said 5HT2A receptor.

64. The method of claim 59, wherein DNA coding for an α subunit of a Gq protein has been introduced into said first population of cells and into said control culture.

65. The method of claim 59, wherein 5-50 ng of DNA coding for said 5HT2A receptor has been introduced into said first population of cells.

* * * * *

UNITED STATES PATENT AND TRADEMARK OFFICE
CERTIFICATE OF CORRECTION

| | | |
|---|---|---|
| PATENT NO. | : 7,425,420 B2 | Page 1 of 2 |
| APPLICATION NO. | : 11/083173 | |
| DATED | : September 16, 2008 | |
| INVENTOR(S) | : Mark R. Brann | |

It is certified that error appears in the above-identified patent and that said Letters Patent is hereby corrected as shown below:

Title Page on Item (56), Page 2, Column 2, Line 25, under Other Publications, before "Neurobiology" please insert --Molecular--.

On Column 2, Line 52, please change "hexosamimidase" to --hexosaminidase--.

On Column 5, Line 19 (Approx.), please change "5HT2A" to --5-HT2A--.

On Column 5, Line 55, please change "$O_2$" to --$\beta_2$--.

On Column 16, Line 15, please change "6-gal" to --$\delta$-gal--.

On Column 17, Line 66, please change "adeno-virus" to --adenovirus--.

On Column 18, Line 5, please change "5 E1b" to --5 Elb--.

On Column 25, line 38, please change "5HT2A" to --5-HT2A--.

On Column 25, Line 67, please change "5 E1b" to --5 Elb--.

On Column 32, Line 21, please change "$\alpha$-galactosidase" to --$\beta$-galactosidase--.

On Column 37, Line 13, please change "of2" to --of 2--.

On Column 37, Line 18, please change "robustresponses" to --robust responses--.

On Column 38, line 46, please change "cotmsfected" to --cotransfected--.

On Column 44, Line 46, please change "a" to --$\alpha$--.

Signed and Sealed this

Fourth Day of May, 2010

David J. Kappos
*Director of the United States Patent and Trademark Office*

On Column 54, Line 20, In Claim 20, after "of" please insert --:--.

On Column 54, Line 23, In Claim 20, please change "which,do" to --which do--.

SEQUENCE LISTING

```
<160> NUMBER OF SEQ ID NOS: 17

<210> SEQ ID NO 1
<211> LENGTH: 20
<212> TYPE: PRT
<213> ORGANISM: Homo sapiens
<220> FEATURE:
<223> OTHER INFORMATION: Portion of wild type M5 receptor

<400> SEQUENCE: 1

Leu Tyr Cys Arg Ile Tyr Arg Glu Thr Glu Lys Arg Thr Lys Asp Leu
1               5                   10                  15

Ala Asp Leu Gln
            20

<210> SEQ ID NO 2
<211> LENGTH: 20
<212> TYPE: PRT
<213> ORGANISM: Artificial Sequence
<220> FEATURE:
<223> OTHER INFORMATION: Portion of mutated M5 receptor

<400> SEQUENCE: 2

Val Tyr Cys Arg Ile Tyr Arg Glu Thr Ala Lys Arg Thr Lys Asp Leu
1               5                   10                  15

Ala Tyr Leu Gln
            20

<210> SEQ ID NO 3
<211> LENGTH: 20
<212> TYPE: PRT
<213> ORGANISM: Artificial Sequence
<220> FEATURE:
<223> OTHER INFORMATION: Portion of mutated M5 receptor

<400> SEQUENCE: 3

Leu Tyr Cys Arg Ile Tyr Arg Glu Thr Glu Glu Arg Ala Lys Asp Leu
1               5                   10                  15

Ala Glu Leu Gln
            20

<210> SEQ ID NO 4
<211> LENGTH: 20
<212> TYPE: PRT
<213> ORGANISM: Artificial Sequence
<220> FEATURE:
<223> OTHER INFORMATION: Portion of mutated M5 receptor
```

```
<400> SEQUENCE: 4

Leu Tyr Cys Arg Ile Tyr Arg Val Ala Glu Lys Arg Thr Lys Val Met
1               5                   10                  15

Ala Asp Leu Gln
            20

<210> SEQ ID NO 5
<211> LENGTH: 20
<212> TYPE: PRT
<213> ORGANISM: Artificial Sequence
<220> FEATURE:
<223> OTHER INFORMATION: Portion of mutated M5 receptor

<400> SEQUENCE: 5

Leu Tyr Cys Arg Ile Tyr Arg Ala Thr Glu Lys Arg Thr Lys Asp Leu
1               5                   10                  15

Ala Asp Leu Gln
            20

<210> SEQ ID NO 6
<211> LENGTH: 20
<212> TYPE: PRT
<213> ORGANISM: Artificial Sequence
<220> FEATURE:
<223> OTHER INFORMATION: Portion of mutated M5 receptor

<400> SEQUENCE: 6

Leu Tyr Cys Arg Ile Tyr Arg Glu Thr Glu Lys Arg Thr Lys Asp Leu
1               5                   10                  15

Ala Asp Leu Leu
            20

<210> SEQ ID NO 7
<211> LENGTH: 20
<212> TYPE: PRT
<213> ORGANISM: Artificial Sequence
<220> FEATURE:
<223> OTHER INFORMATION: Portion of mutated M5 receptor

<400> SEQUENCE: 7

Leu Tyr Gly Arg Ile Tyr Arg Glu Thr Val Glu Arg Thr Lys Asn Leu
1               5                   10                  15

Ala Asp Leu Gln
            20

<210> SEQ ID NO 8
<211> LENGTH: 20
<212> TYPE: PRT
<213> ORGANISM: Artificial Sequence
<220> FEATURE:
<223> OTHER INFORMATION: Portion of mutated M5 receptor

<400> SEQUENCE: 8

Leu Tyr Trp Arg Ile Tyr Arg Glu Thr Glu Lys Arg Thr Lys Asp Leu
1               5                   10                  15

Ala Ala Leu Gln
            20

<210> SEQ ID NO 9
<211> LENGTH: 20
<212> TYPE: PRT
<213> ORGANISM: Artificial Sequence
<220> FEATURE:
```

<223> OTHER INFORMATION: Portion of mutated M5 receptor

<400> SEQUENCE: 9

Leu Tyr Trp Arg Ile Tyr Arg Glu Thr Val Lys Arg Thr Lys Asp Leu
1               5                   10                  15

Ala Asp Leu Gln
            20

<210> SEQ ID NO 10
<211> LENGTH: 20
<212> TYPE: PRT
<213> ORGANISM: Artificial Sequence
<220> FEATURE:
<223> OTHER INFORMATION: Portion of mutated M4 receptor

<400> SEQUENCE: 10

Leu Tyr Ile His Ile Ser Leu Ala Ser Arg Ser Arg Val His Lys His
1               5                   10                  15

Arg Pro Glu Gly
            20

<210> SEQ ID NO 11
<211> LENGTH: 20
<212> TYPE: PRT
<213> ORGANISM: Homo sapiens
<220> FEATURE:
<223> OTHER INFORMATION: Portion of wild type M2 receptor

<400> SEQUENCE: 11

Leu Tyr Trp His Ile Ser Arg Ala Ser Lys Ser Arg Ile Lys Lys Asp
1               5                   10                  15

Lys Lys Glu Pro
            20

<210> SEQ ID NO 12
<211> LENGTH: 20
<212> TYPE: PRT
<213> ORGANISM: Homo sapiens
<220> FEATURE:
<223> OTHER INFORMATION: Portion of wild type M1 receptor

<400> SEQUENCE: 12

Leu Tyr Trp Arg Ile Tyr Arg Glu Thr Glu Asn Arg Ala Arg Glu Leu
1               5                   10                  15

Ala Ala Leu Gln
            20

<210> SEQ ID NO 13
<211> LENGTH: 20
<212> TYPE: PRT
<213> ORGANISM: Homo sapiens
<220> FEATURE:
<223> OTHER INFORMATION: Portion of wild type M3 receptor

<400> SEQUENCE: 13

Leu Tyr Trp Arg Ile Tyr Lys Glu Thr Glu Lys Arg Thr Lys Glu Leu
1               5                   10                  15

Ala Gly Leu Gln
            20

<210> SEQ ID NO 14
<211> LENGTH: 22
<212> TYPE: DNA
<213> ORGANISM: Artificial Sequence -continued

```
<220> FEATURE:
<223> OTHER INFORMATION: PCR Primer

<400> SEQUENCE: 14
agctccggga gaacagcatg ta                                                  22

<210> SEQ ID NO 15
<211> LENGTH: 33
<212> TYPE: DNA
<213> ORGANISM: Artificial Sequence
<220> FEATURE:
<223> OTHER INFORMATION: PCR Primer

<400> SEQUENCE: 15
gagtgtggat ccatcaaggt gaatggtgag cag                                      33

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
caatgaacag catagcagca a                                                   21

<210> SEQ ID NO 17
<211> LENGTH: 34
<212> TYPE: DNA
<213> ORGANISM: Artificial Sequence
<220> FEATURE:
<223> OTHER INFORMATION: PCR Primer

<400> SEQUENCE: 17
ggtttcctct agaaaataga agttaattta gatt                                     34
```